United States Patent
Ono et al.

(10) Patent No.: US 11,702,641 B2
(45) Date of Patent: Jul. 18, 2023

(54) STEVIOL GLYCOSIDE HEXOSE TRANSFERASE AND GENE CODING FOR SAME

(71) Applicant: SUNTORY HOLDINGS LIMITED, Osaka (JP)

(72) Inventors: Eiichiro Ono, Kyoto (JP); Misa Ochiai, Kyoto (JP); Kazunari Iwaki, Kyoto (JP); Tadayoshi Hirai, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 506 days.

(21) Appl. No.: 16/473,819

(22) PCT Filed: Dec. 26, 2017

(86) PCT No.: PCT/JP2017/046804
§ 371 (c)(1),
(2) Date: Jun. 26, 2019

(87) PCT Pub. No.: WO2018/124141
PCT Pub. Date: Jul. 5, 2018

(65) Prior Publication Data
US 2020/0123509 A1    Apr. 23, 2020

(30) Foreign Application Priority Data

Dec. 27, 2016  (JP) ................ 2016-252643

(51) Int. Cl.
| | | |
|---|---|---|
| *C12N 9/10* | (2006.01) | |
| *C12N 15/70* | (2006.01) | |
| *C12N 15/81* | (2006.01) | |
| *C12N 15/82* | (2006.01) | |
| *C12P 19/56* | (2006.01) | |

(52) U.S. Cl.
CPC .......... *C12N 9/1048* (2013.01); *C12N 15/70* (2013.01); *C12N 15/81* (2013.01); *C12N 15/8245* (2013.01); *C12P 19/56* (2013.01)

(58) Field of Classification Search
None
See application file for complete search history.

(56) References Cited

U.S. PATENT DOCUMENTS

| | | |
|---|---|---|
| 9,957,540 B2 | 5/2018 | Mikkelsen et al. |
| 10,612,066 B2 | 4/2020 | Mikkelsen et al. |
| 11,530,431 B2 | 12/2022 | Mikkelsen et al. |
| 2008/0064063 A1 | 3/2008 | Brandle et al. |
| 2012/0329884 A1* | 12/2012 | Markosyan ............ A23L 27/30  514/781 |
| 2013/0171328 A1 | 7/2013 | Kishore et al. |
| 2014/0329281 A1 | 11/2014 | Houghton-Larsen et al. |
| 2015/0159188 A1 | 6/2015 | Ono et al. |
| 2015/0361476 A1 | 12/2015 | Simon et al. |
| 2016/0186225 A1 | 6/2016 | Mikkelsen et al. |
| 2018/0371517 A1 | 12/2018 | Simon et al. |
| 2019/0203243 A1 | 7/2019 | Mikkelsen et al. |
| 2020/0308617 A1 | 10/2020 | Mikkelsen et al. |

FOREIGN PATENT DOCUMENTS

| | | |
|---|---|---|
| CN | 105051195 | 11/2015 |
| EP | 1 897 951 | 3/2008 |
| EP | 2 826 861 | 1/2015 |
| JP | 2013-533736 | 8/2013 |
| JP | 2014-524247 | 9/2014 |
| WO | 2013/137487 | 9/2013 |
| WO | 2014/122328 | 8/2014 |

OTHER PUBLICATIONS

Brandle et al., "Steviol glycoside biosynthesis", *Phytochemistry* vol. 68, pp. 1855-1863 (2007).
Richman et al., "Functional genomics uncovers three glucosyltransferases involved in the synthesis of the major sweet glucosides of *Stevia rebaudiana*", *The Plant Journal*, vol. 41, pp. 56-67 (2005).
International Search Report issued in PCT/JP2017/046804, dated Apr. 3, 2018, along with an English-language translation.
Extended European Search Report issued in EP Patent Application No. 17887924.3, dated Jun. 29, 2020.
Office Action issued in CN Patent Application No. 201780080859.X, dated Nov. 15, 2022, along with a machine English translation.

* cited by examiner

*Primary Examiner* — Suzanne M Noakes
(74) *Attorney, Agent, or Firm* — Greenblum & Bernstein, P.L.C.

(57) ABSTRACT

The purpose of the present invention is to provide a steviol glycoside hexose transferase, and a method for producing a steviol glycoside that contains glucose and/or rhamnose using said enzyme. The present invention provides a steviol glycoside hexose transferase, and a method for producing a steviol glycoside that contains glucose and/or rhamnose using said enzyme. The present invention also provides a transformant into which a steviol glycoside hexose transferase gene has been introduced, and a method for preparing said transformant.

23 Claims, 19 Drawing Sheets
Specification includes a Sequence Listing.

[Figure 1]

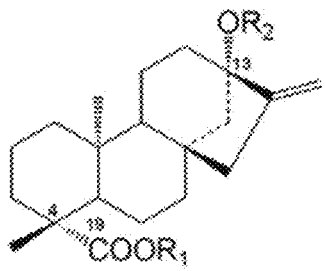

| Name | R₁ | R₂ |
|---|---|---|
| Steviol | H | H |
| Steviolmonoside | H | Glc |
| Steviolbioside | H | Glc-Glc(β2→1) |
| Dulcoside A | Glc | Glc-Rha(β2→1) |
| Rubusoside | Glc | Glc |
| Stevioside | Glc | Glc-Glc(β2→1) |
| Rebaudioside A | Glc | Glc-Glc(β2→1)<br>    \|<br>Glc(β3→1) |
| Rebaudioside B | H | Glc-Glc(β2→1)<br>    \|<br>Glc(β3→1) |
| Rebaudioside C (Dulcoside B) | Glc | Glc-Rha(β2→1)<br>    \|<br>Glc(β3→1) |
| Rebaudioside D | Glc-Glc(β2→1) | Glc-Glc(β2→1)<br>    \|<br>Glc(β3→1) |
| Rebaudioside E | Glc-Glc(β2→1) | Glc-Glc(β2→1) |
| Rebaudioside F | Glc | Glc-Xyl(β2→1)<br>    \|<br>Glc(β3→1) |

[Figure 2]
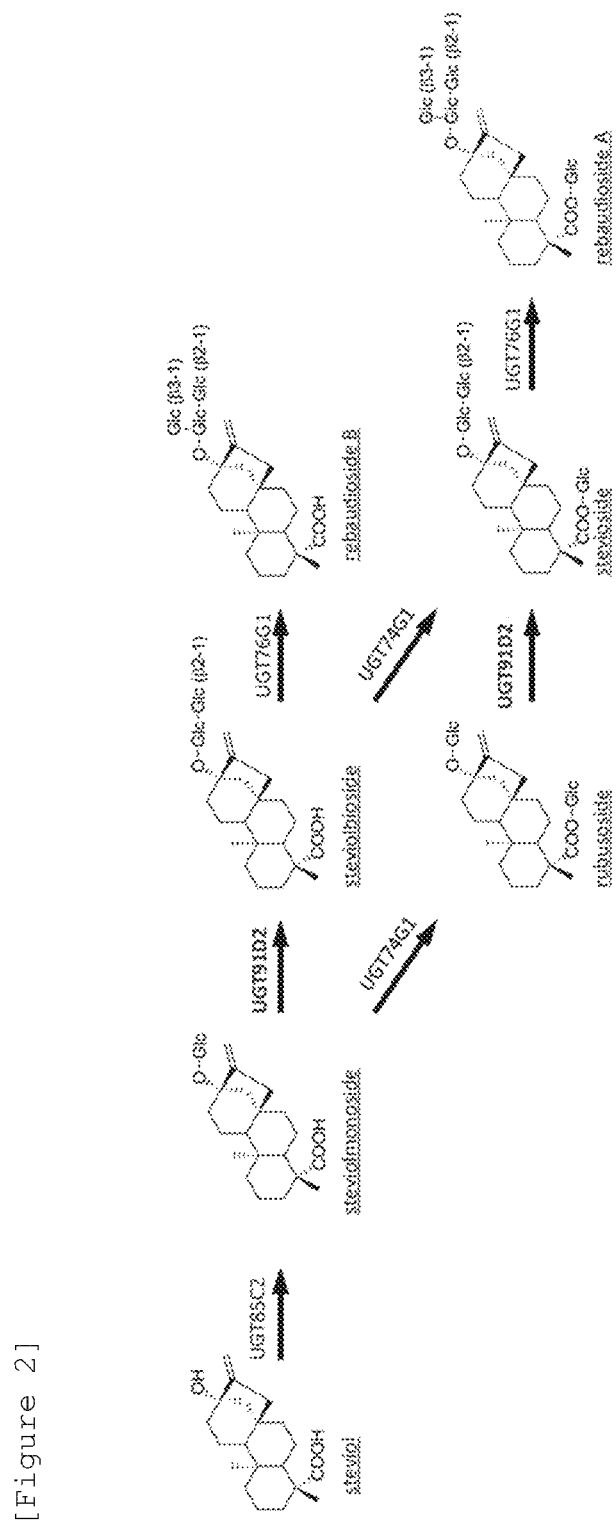

[Figure 3]
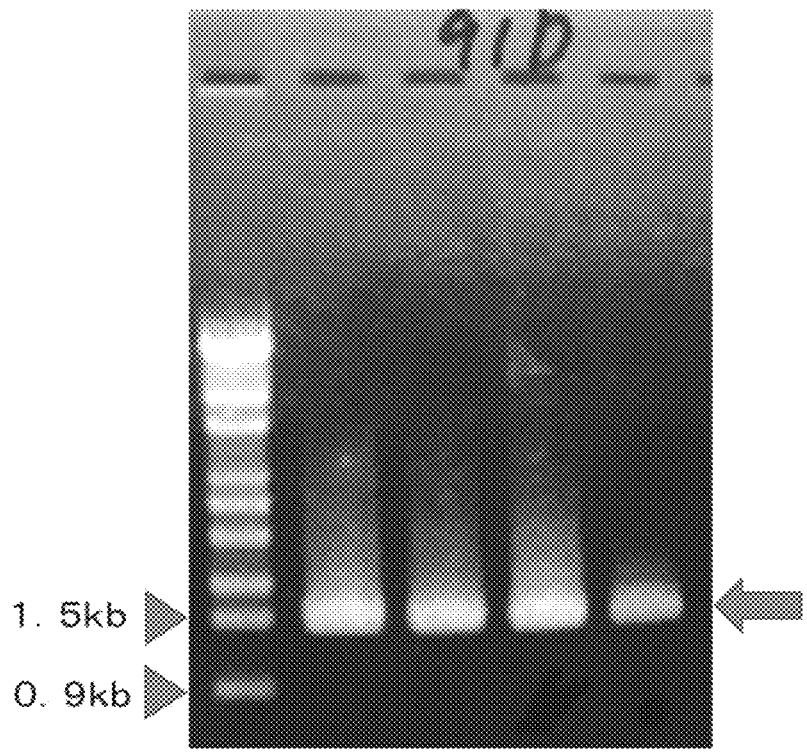

[Figure 4]
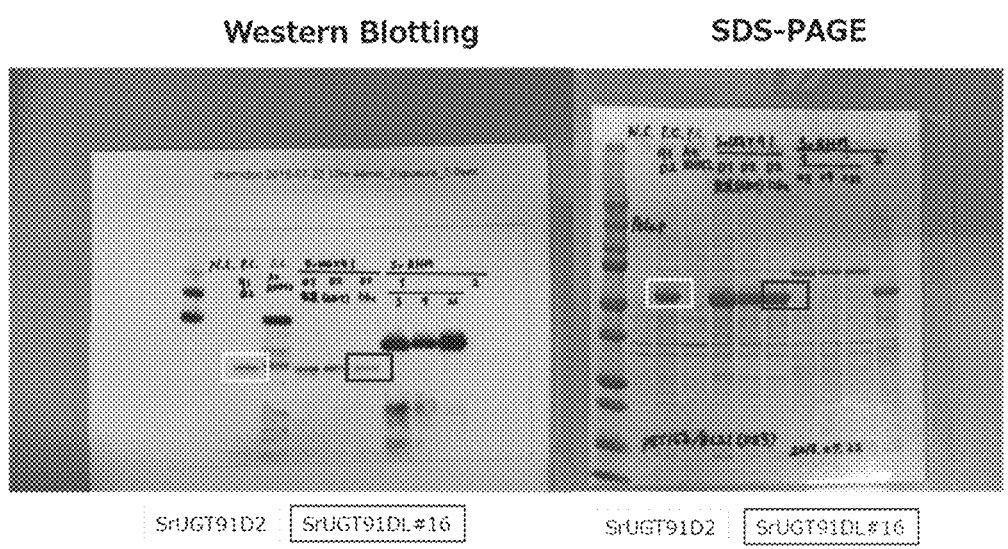

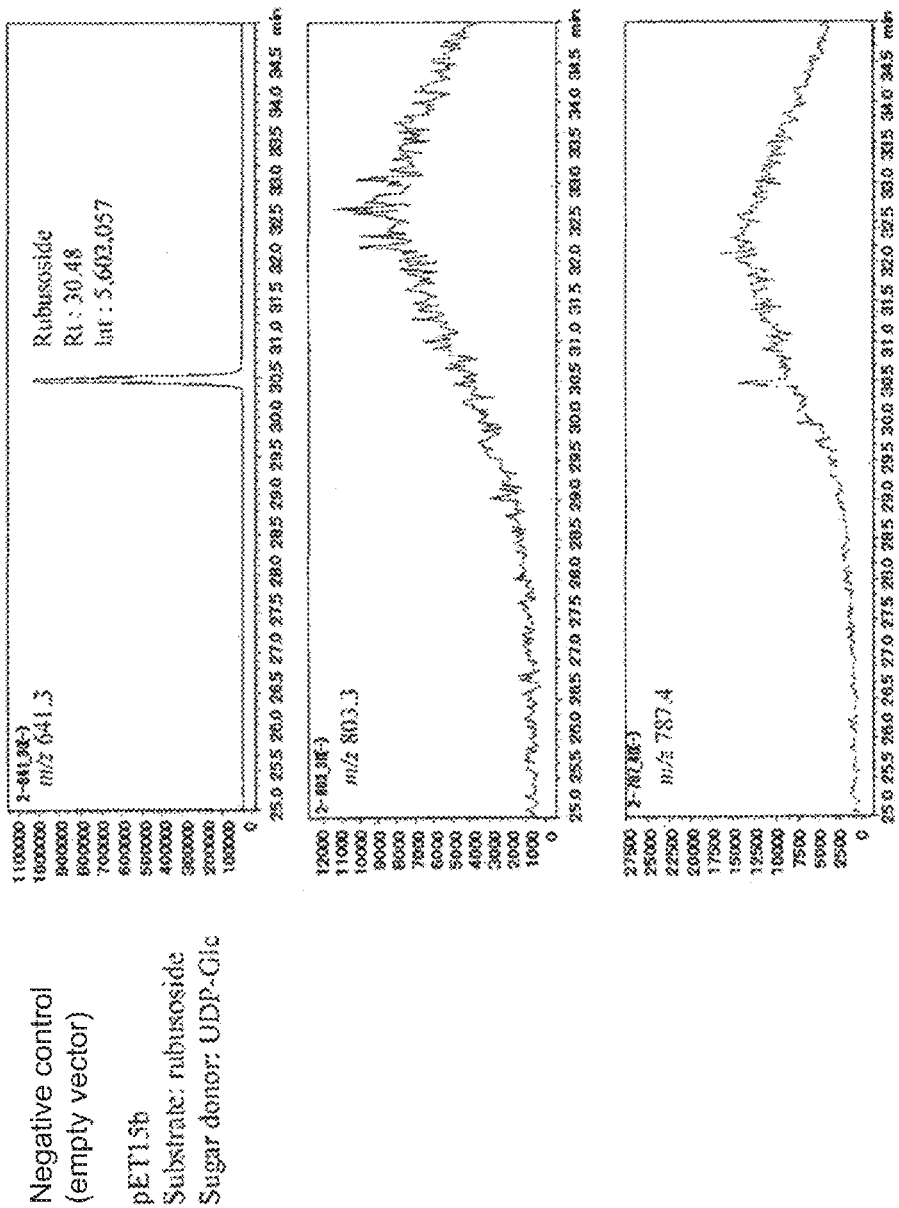
Figure 5-1: Enzymatic activity of recombinant protein

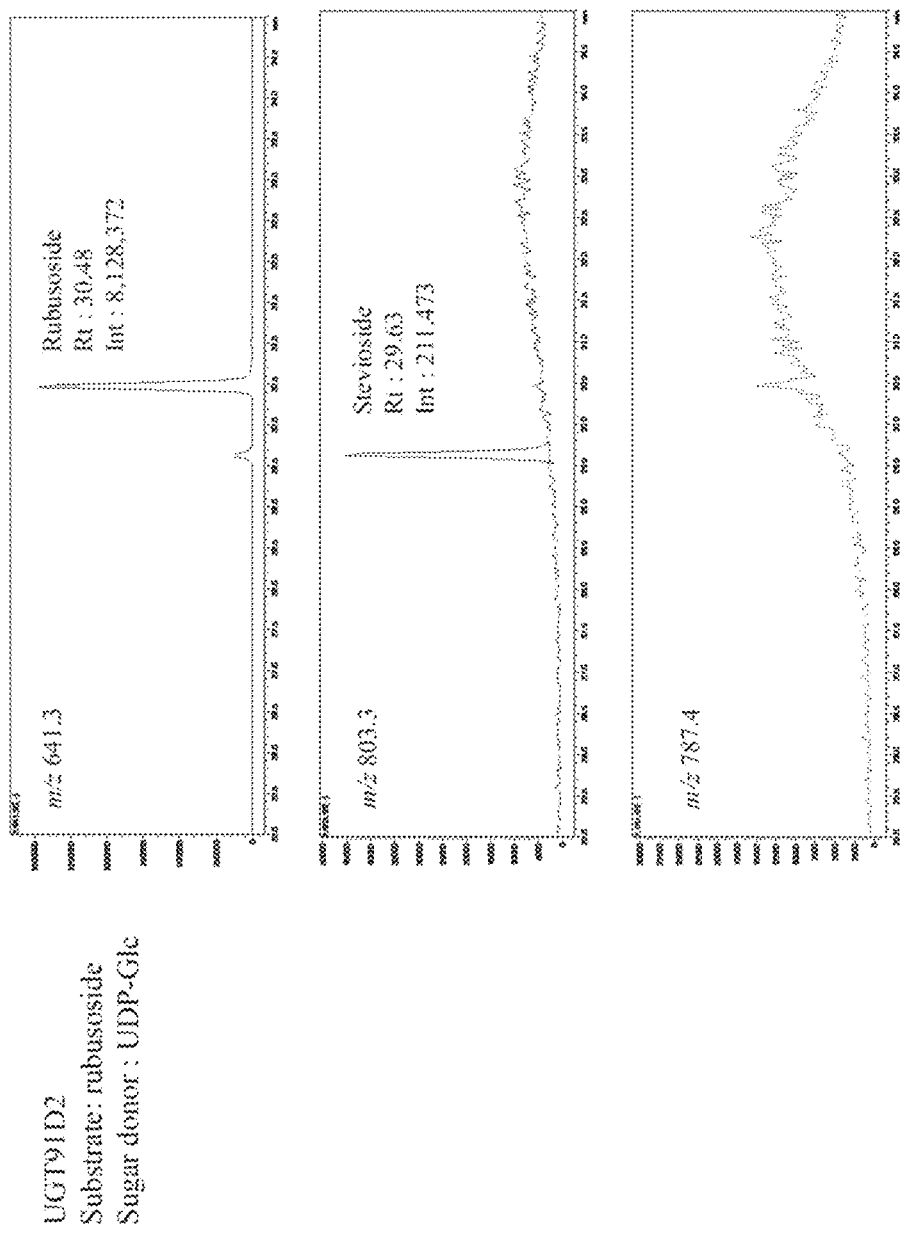
[Figure 5-2]

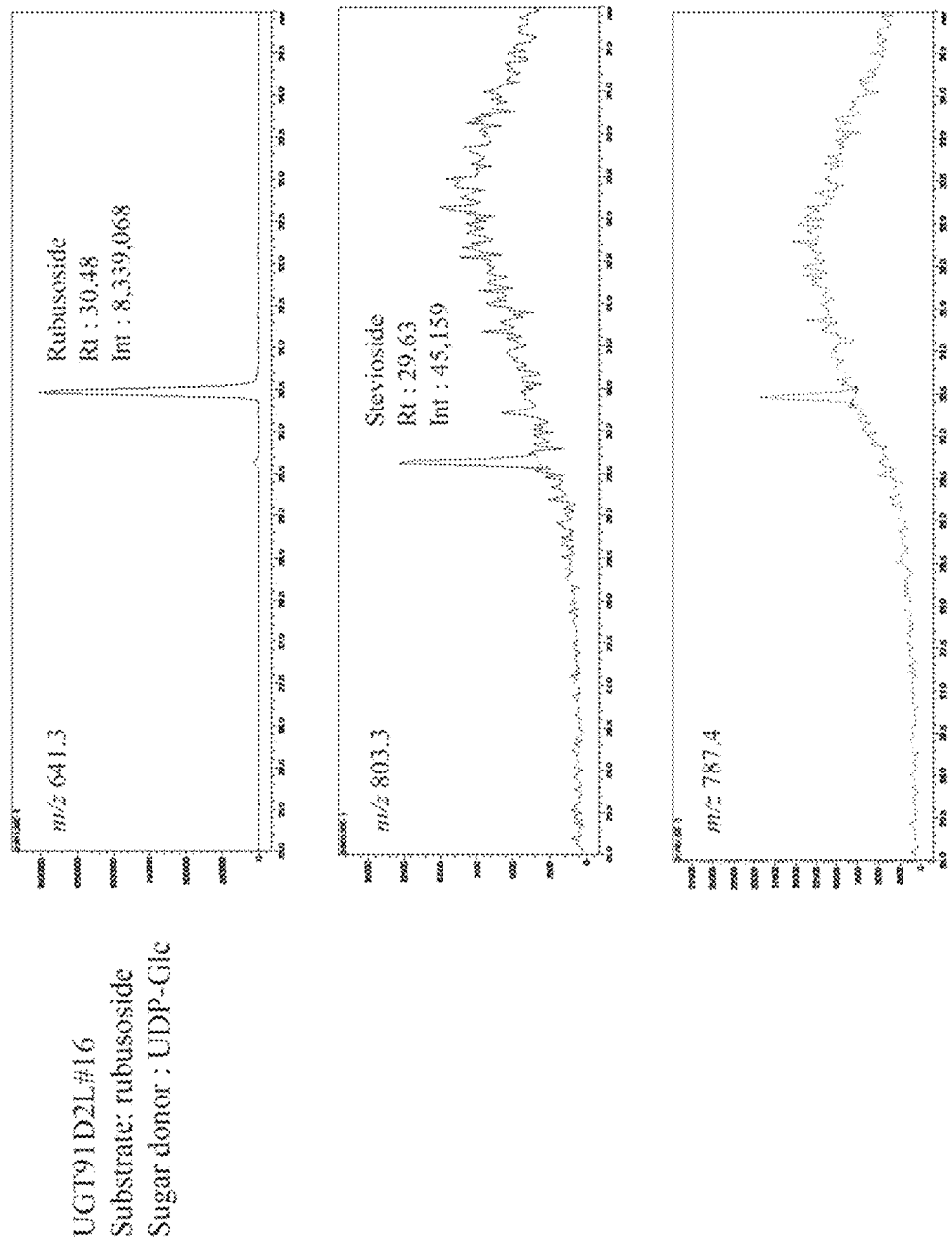
[Figure 5-3]

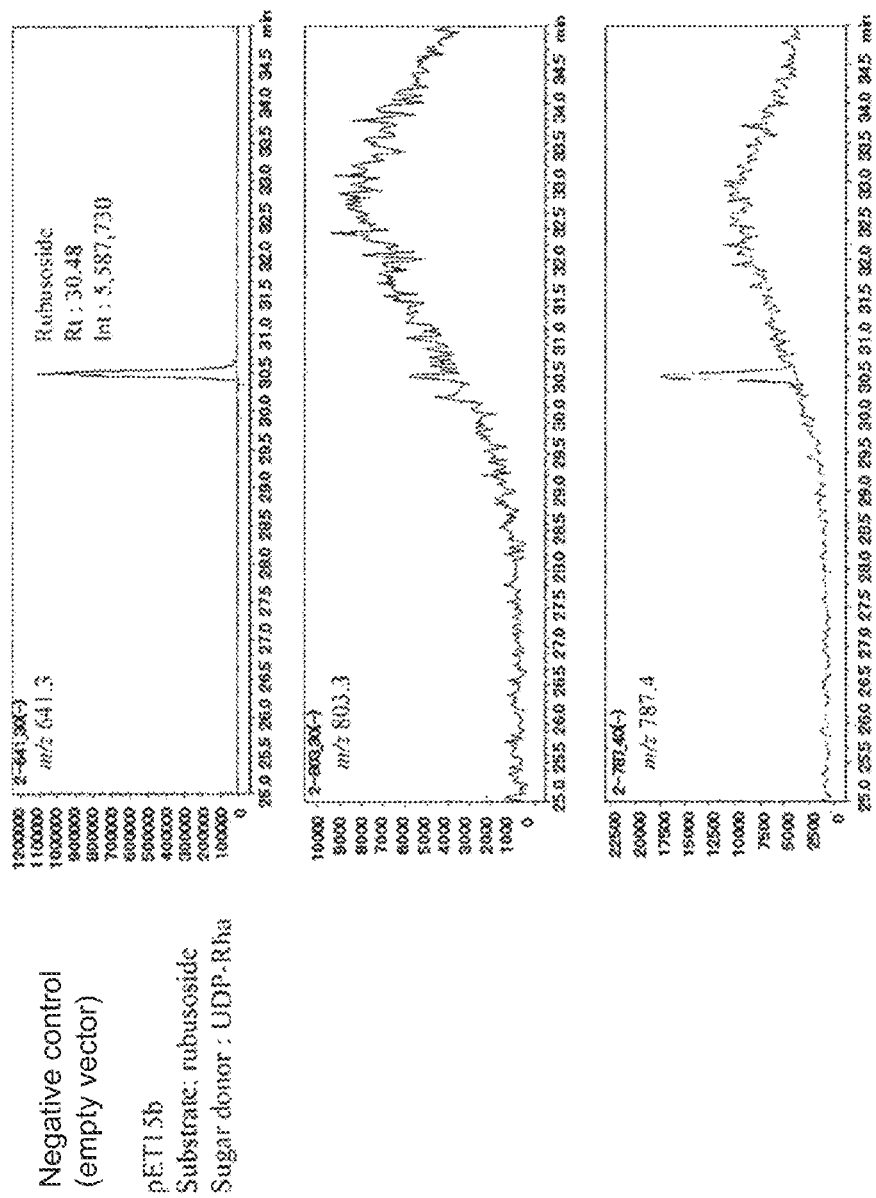
Figure 6-1: Enzymatic activity of recombinant protein

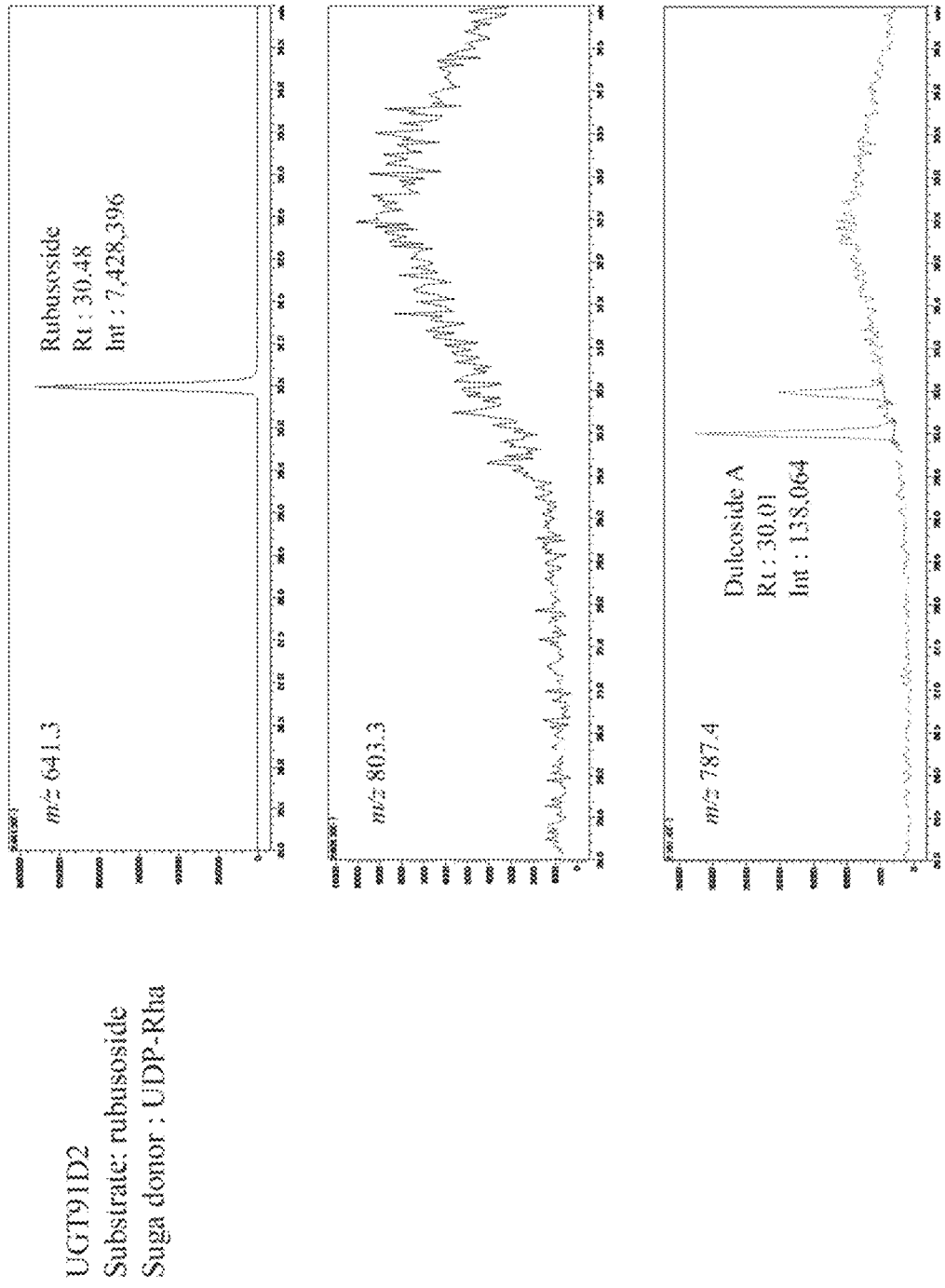
[Figure 6-2]
UGT91D2
Substrate: rubusoside
Sugar donor: UDP-Rha

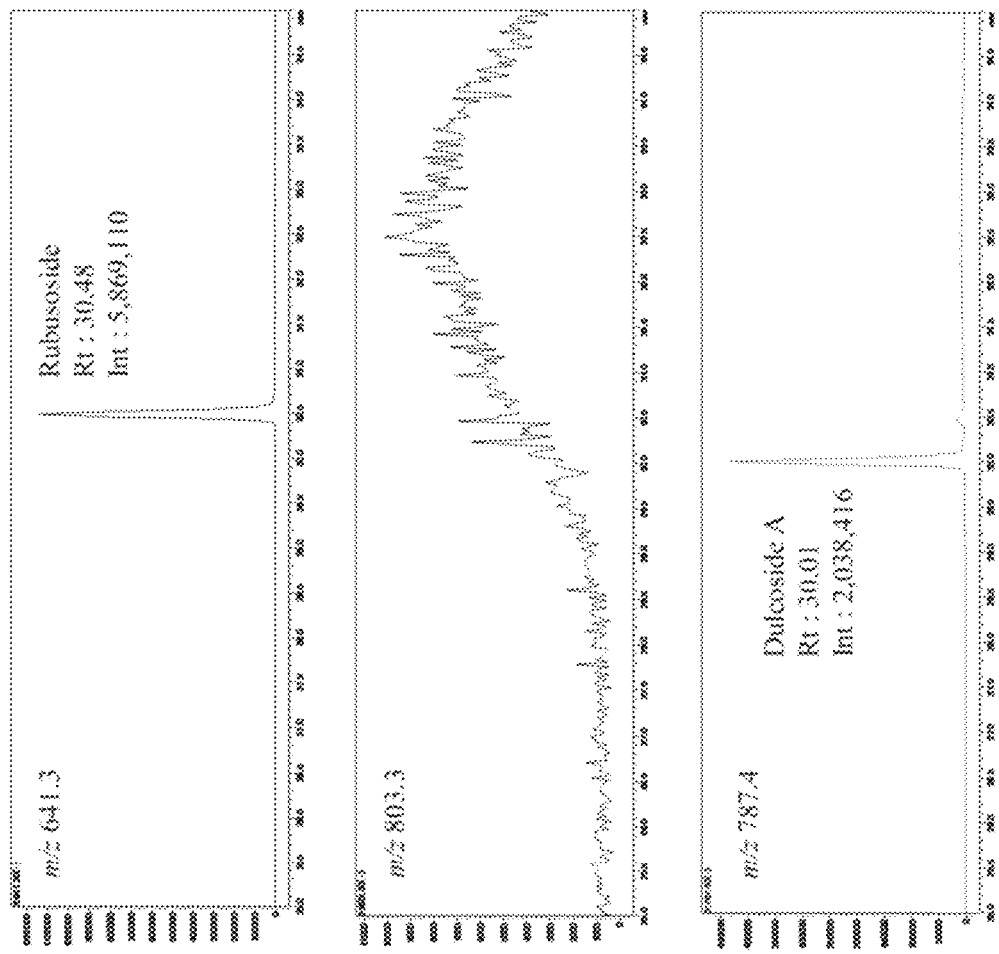
[Figure 6-3]
UGT91D2L#16
Substrate: rubusoside
Sugar donor: UDP-Rha

[Figure 7]
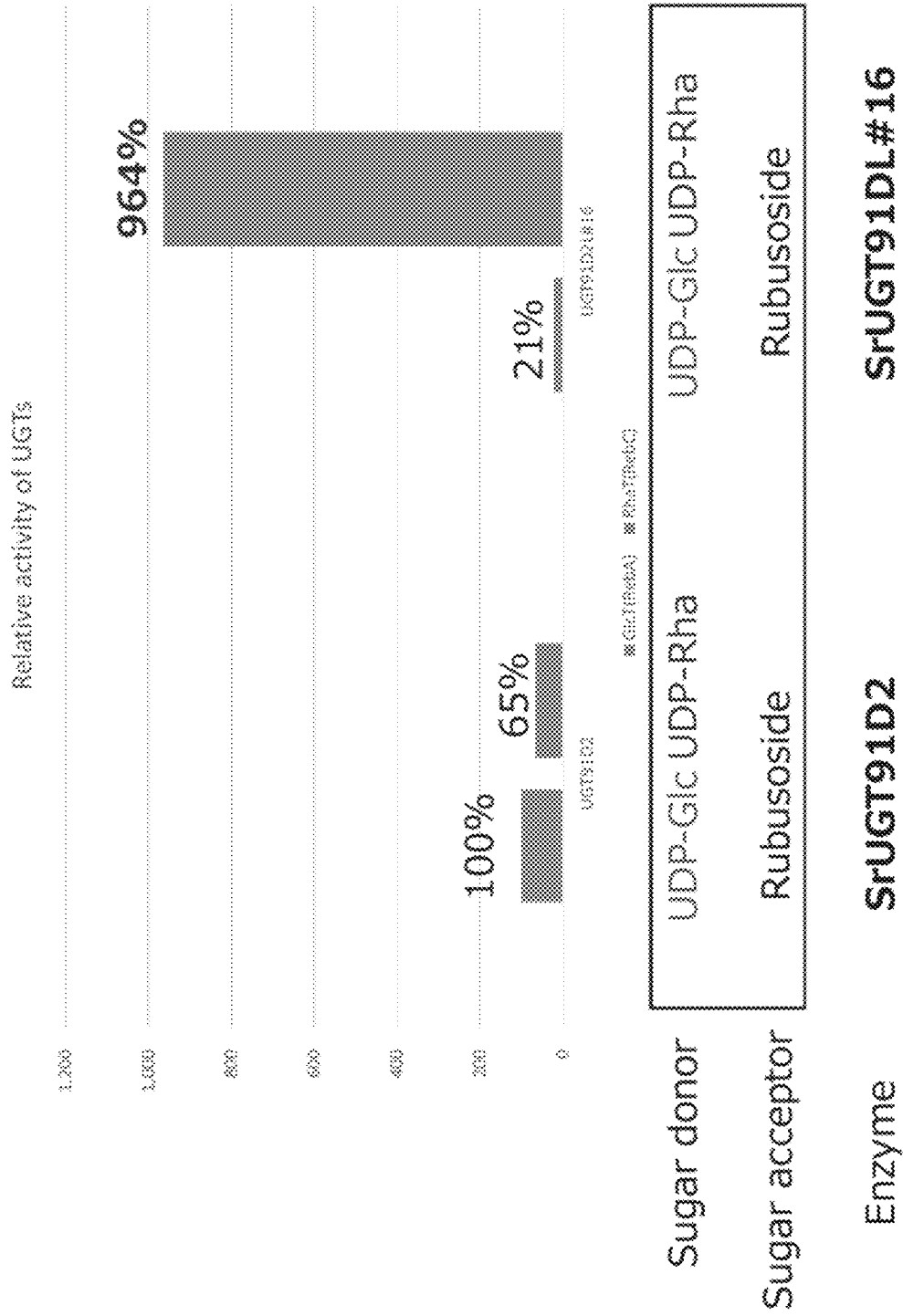

[Figure 8]
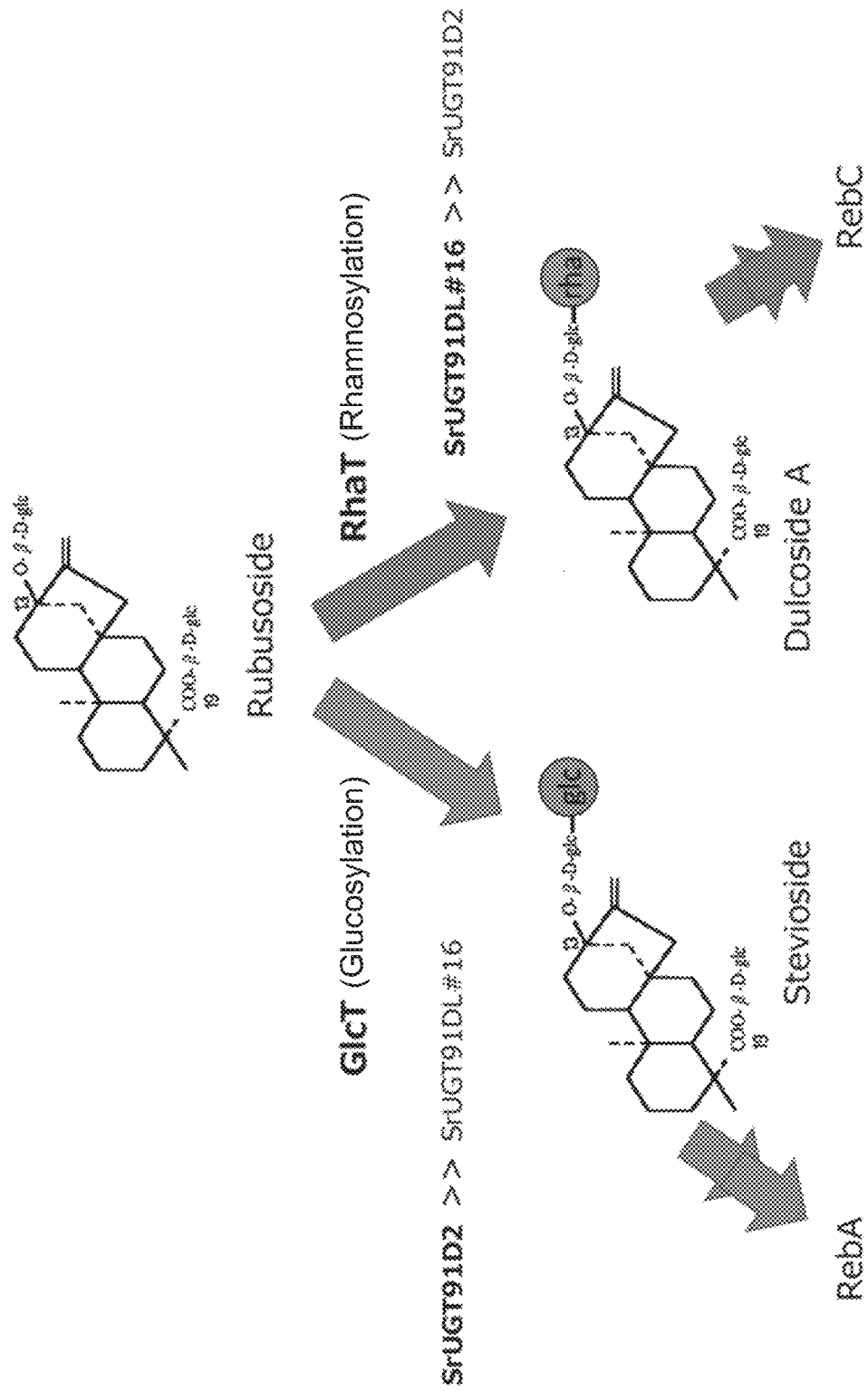

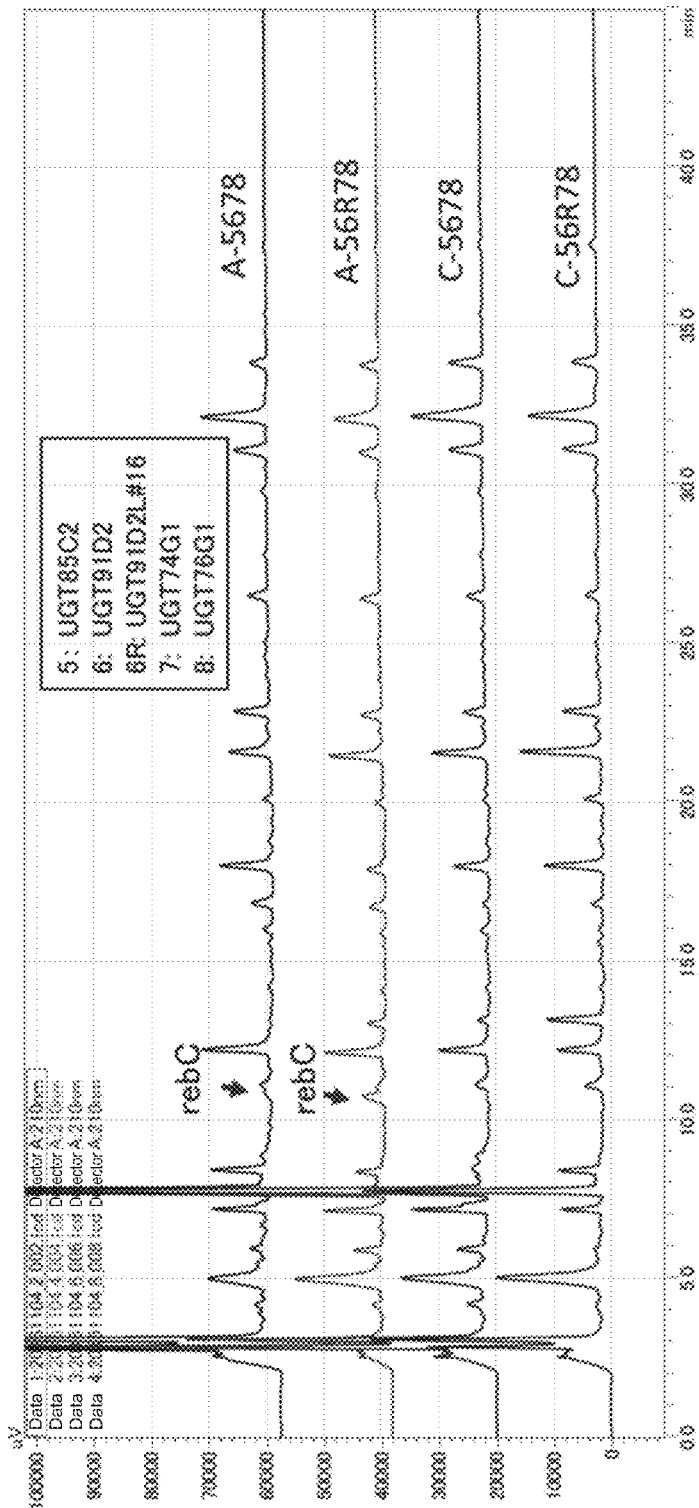
[Figure 9]

[Figure 10]
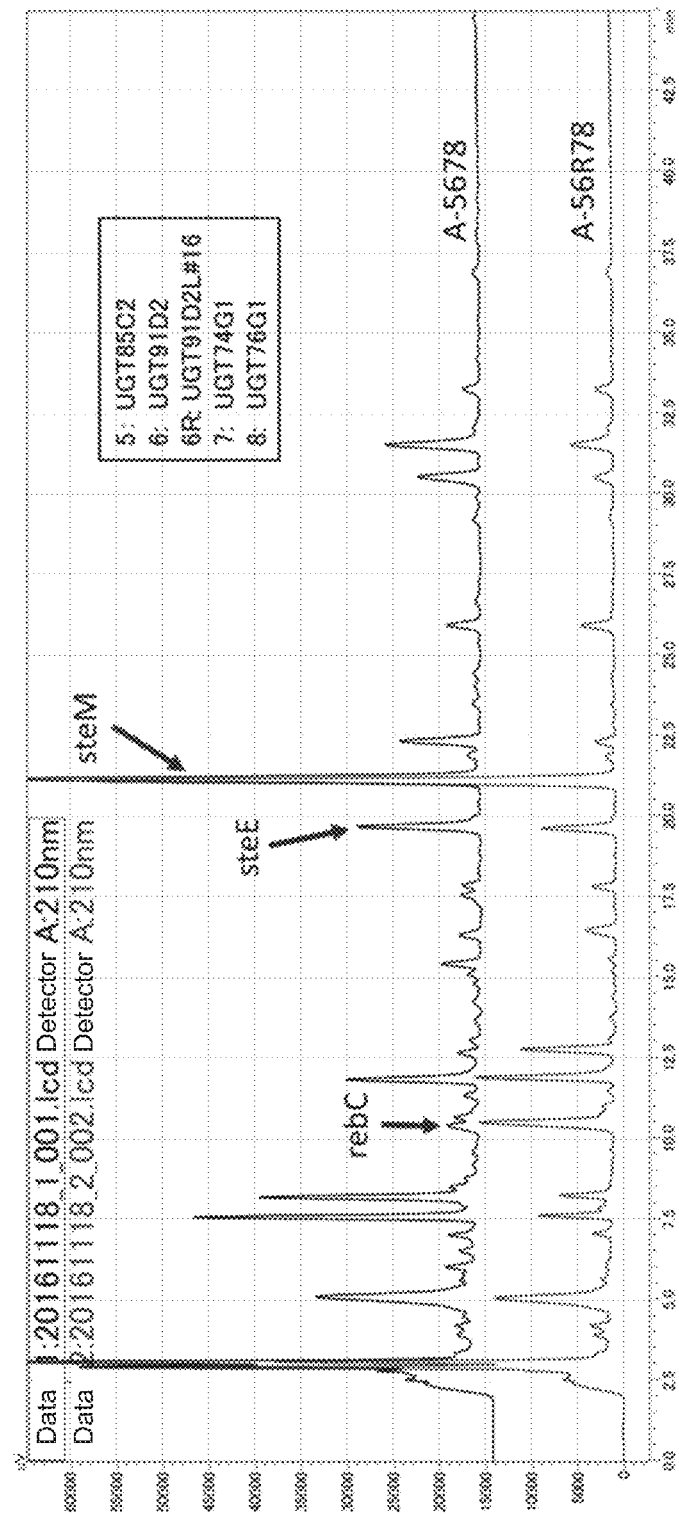

[Figure 11]
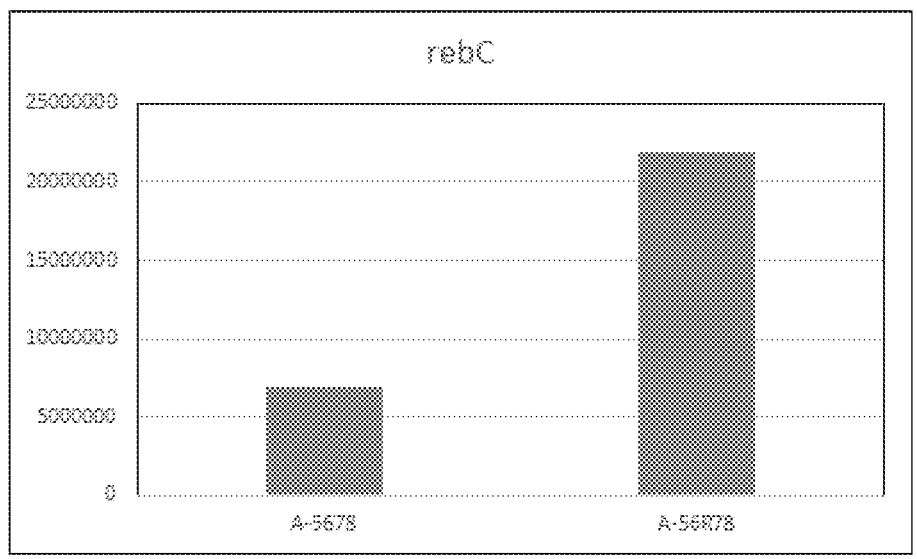

[Figure 12]
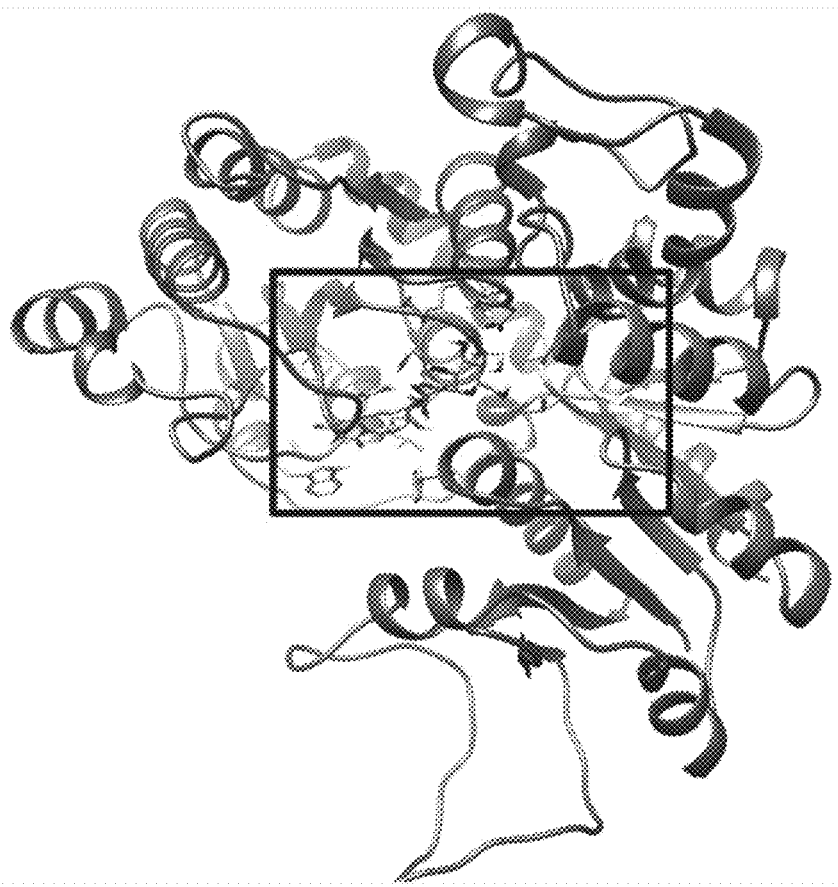

[Figure 13]
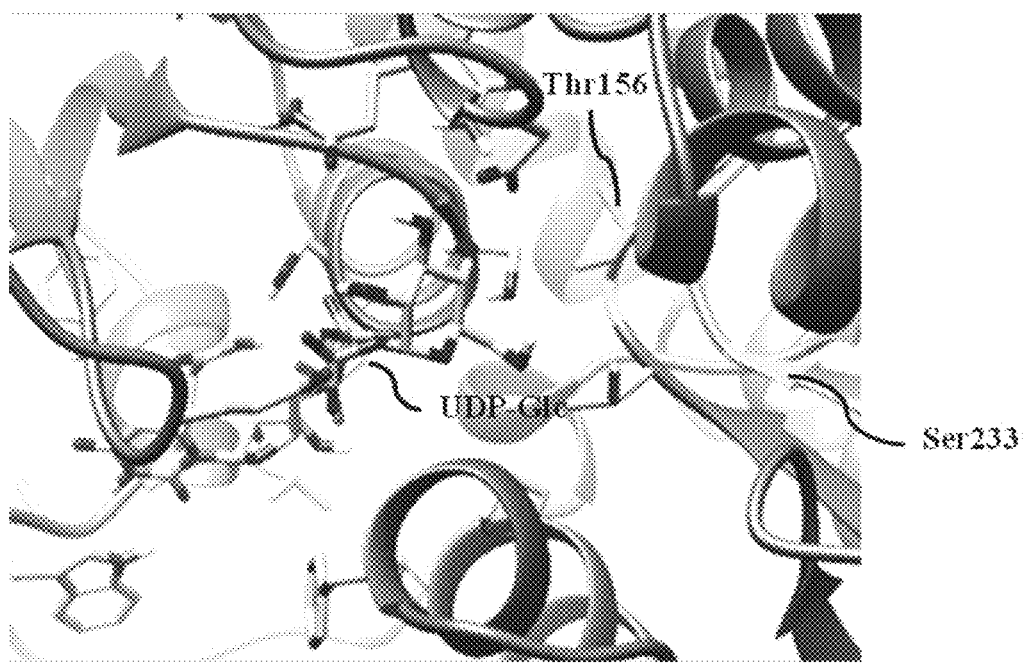

[Figure 14]
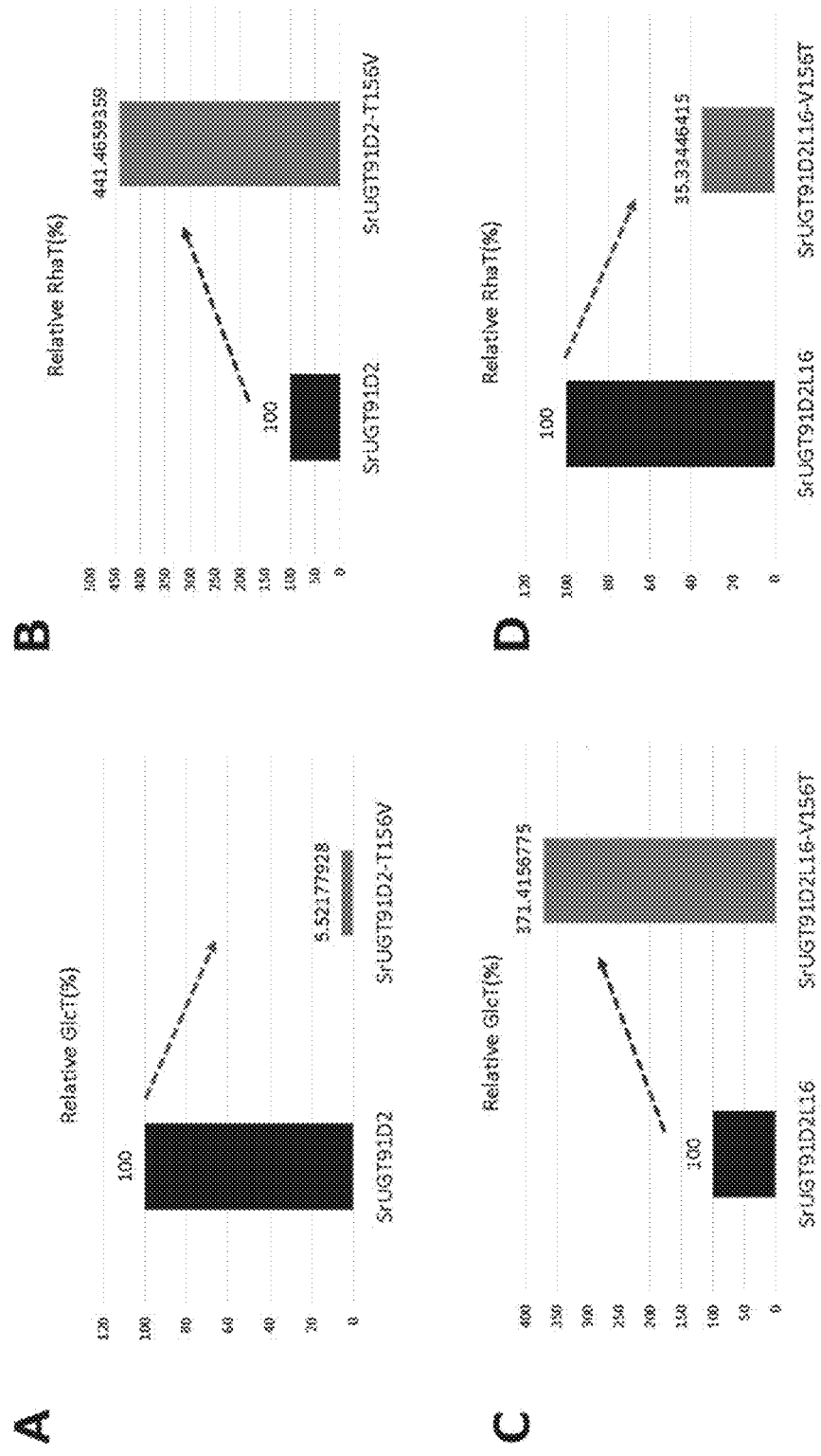

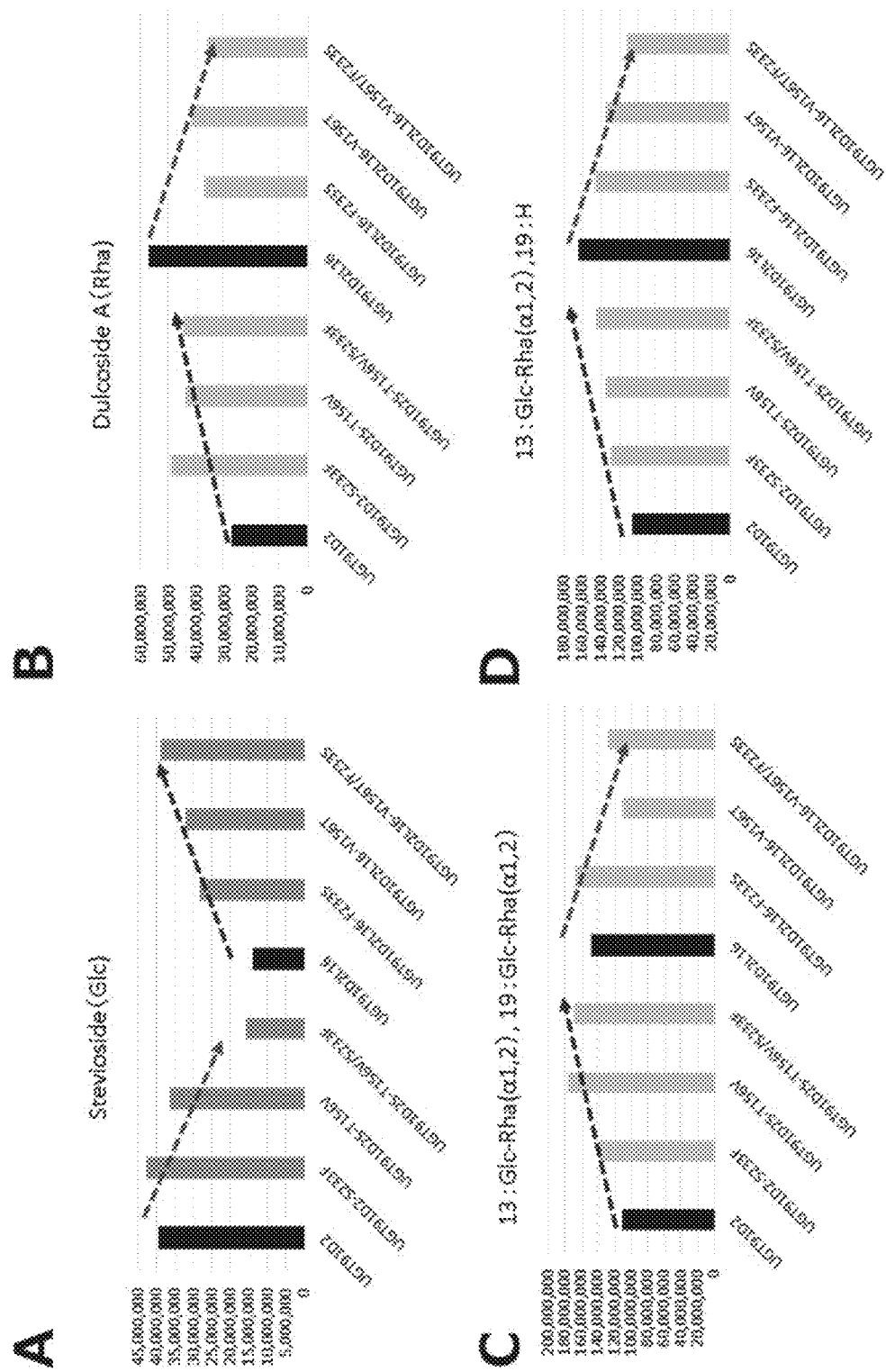
[Figure 15]

SEQUENCE LISTING

<160> NUMBER OF SEQ ID NOS: 46

<210> SEQ ID NO 1
<211> LENGTH: 1458
<212> TYPE: DNA
<213> ORGANISM: Stevia rebaudiana
<220> FEATURE:
<221> NAME/KEY: CDS
<222> LOCATION: (1)..(1458)

<400> SEQUENCE: 1

| | | | | | | | | | | | | | | | | |
|---|---|---|---|---|---|---|---|---|---|---|---|---|---|---|---|---|
| atg | tac | aac | gtt | act | tat | cat | caa | aat | tca | aaa | gca | atg | gct | acc | agt | 48 |
| Met | Tyr | Asn | Val | Thr | Tyr | His | Gln | Asn | Ser | Lys | Ala | Met | Ala | Thr | Ser | |
| 1 | | | | 5 | | | | | 10 | | | | | 15 | | |

| gac | tcc | ata | gtt | gac | gac | cgt | aag | cag | ctt | cat | gtt | gcg | acg | ttc | cca | 96 |
|---|---|---|---|---|---|---|---|---|---|---|---|---|---|---|---|---|
| Asp | Ser | Ile | Val | Asp | Asp | Arg | Lys | Gln | Leu | His | Val | Ala | Thr | Phe | Pro | |
| | | | 20 | | | | | 25 | | | | | 30 | | | |

| tgg | ctt | gct | ttc | ggt | cac | atc | ctc | cct | ttc | ctt | cag | ctt | tcg | aaa | ttg | 144 |
|---|---|---|---|---|---|---|---|---|---|---|---|---|---|---|---|---|
| Trp | Leu | Ala | Phe | Gly | His | Ile | Leu | Pro | Phe | Leu | Gln | Leu | Ser | Lys | Leu | |
| | | 35 | | | | | 40 | | | | | 45 | | | | |

| ata | gct | gaa | aag | ggt | cac | aaa | gtc | tcg | ttt | ctt | tct | acc | acc | aga | aac | 192 |
|---|---|---|---|---|---|---|---|---|---|---|---|---|---|---|---|---|
| Ile | Ala | Glu | Lys | Gly | His | Lys | Val | Ser | Phe | Leu | Ser | Thr | Thr | Arg | Asn | |
| 50 | | | | | 55 | | | | | 60 | | | | | | |

| att | caa | cgt | ctc | tct | tct | cat | atc | tcg | cca | ctc | ata | aat | gtt | gtt | caa | 240 |
|---|---|---|---|---|---|---|---|---|---|---|---|---|---|---|---|---|
| Ile | Gln | Arg | Leu | Ser | Ser | His | Ile | Ser | Pro | Leu | Ile | Asn | Val | Val | Gln | |
| 65 | | | | | 70 | | | | | 75 | | | | | 80 | |

| ctc | aca | ctt | cca | cgt | gtc | caa | gag | ctg | ccg | gag | gat | gca | gag | gcg | acc | 288 |
|---|---|---|---|---|---|---|---|---|---|---|---|---|---|---|---|---|
| Leu | Thr | Leu | Pro | Arg | Val | Gln | Glu | Leu | Pro | Glu | Asp | Ala | Glu | Ala | Thr | |
| | | | | 85 | | | | | 90 | | | | | 95 | | |

| act | gac | gtc | cac | cct | gaa | gat | att | cca | tat | ctc | aag | aag | gct | tct | gat | 336 |
|---|---|---|---|---|---|---|---|---|---|---|---|---|---|---|---|---|
| Thr | Asp | Val | His | Pro | Glu | Asp | Ile | Pro | Tyr | Leu | Lys | Lys | Ala | Ser | Asp | |
| | | | 100 | | | | | 105 | | | | | 110 | | | |

| ggt | ctt | caa | ccg | gag | gtc | acc | cgg | ttt | cta | gaa | caa | cac | tct | ccg | gac | 384 |
|---|---|---|---|---|---|---|---|---|---|---|---|---|---|---|---|---|
| Gly | Leu | Gln | Pro | Glu | Val | Thr | Arg | Phe | Leu | Glu | Gln | His | Ser | Pro | Asp | |
| | | 115 | | | | | 120 | | | | | 125 | | | | |

| tgg | att | att | tat | gat | tat | act | cac | tac | tgg | ttg | cca | tcc | atc | gcg | gct | 432 |
|---|---|---|---|---|---|---|---|---|---|---|---|---|---|---|---|---|
| Trp | Ile | Ile | Tyr | Asp | Tyr | Thr | His | Tyr | Trp | Leu | Pro | Ser | Ile | Ala | Ala | |
| 130 | | | | | 135 | | | | | 140 | | | | | | |

| agc | ctc | ggt | atc | tca | cga | gcc | cac | ttc | tcc | gtc | gtc | act | cca | tgg | gcc | 480 |
|---|---|---|---|---|---|---|---|---|---|---|---|---|---|---|---|---|
| Ser | Leu | Gly | Ile | Ser | Arg | Ala | His | Phe | Ser | Val | Val | Thr | Pro | Trp | Ala | |
| 145 | | | | | 150 | | | | | 155 | | | | | 160 | |

| att | gct | tat | atg | gga | ccc | tca | gct | gac | gcc | atg | ata | aat | ggt | tca | gat | 528 |
|---|---|---|---|---|---|---|---|---|---|---|---|---|---|---|---|---|
| Ile | Ala | Tyr | Met | Gly | Pro | Ser | Ala | Asp | Ala | Met | Ile | Asn | Gly | Ser | Asp | |
| | | | | 165 | | | | | 170 | | | | | 175 | | |

| ggt | cga | acc | acg | gtt | gag | gat | ctc | acg | aca | ccg | ccc | aag | tgg | ttt | ccc | 576 |
|---|---|---|---|---|---|---|---|---|---|---|---|---|---|---|---|---|
| Gly | Arg | Thr | Thr | Val | Glu | Asp | Leu | Thr | Thr | Pro | Pro | Lys | Trp | Phe | Pro | |
| | | | 180 | | | | | 185 | | | | | 190 | | | |

| ttt | ccg | acc | aaa | gta | tgc | tgg | cgg | aag | cat | gat | ctt | gcc | cga | ctg | gtg | 624 |
|---|---|---|---|---|---|---|---|---|---|---|---|---|---|---|---|---|
| Phe | Pro | Thr | Lys | Val | Cys | Trp | Arg | Lys | His | Asp | Leu | Ala | Arg | Leu | Val | |
| | | 195 | | | | | 200 | | | | | 205 | | | | |

| cct | tac | aaa | gct | ccg | ggg | ata | tct | gat | gga | tac | cgt | atg | ggg | ctg | gtt | 672 |
|---|---|---|---|---|---|---|---|---|---|---|---|---|---|---|---|---|
| Pro | Tyr | Lys | Ala | Pro | Gly | Ile | Ser | Asp | Gly | Tyr | Arg | Met | Gly | Leu | Val | |
| | 210 | | | | | 215 | | | | | 220 | | | | | |

| ctt | aag | gga | tct | gat | tgt | ttg | ctt | ttc | aaa | tgt | tac | cat | gag | ttt | gga | 720 |
|---|---|---|---|---|---|---|---|---|---|---|---|---|---|---|---|---|
| Leu | Lys | Gly | Ser | Asp | Cys | Leu | Leu | Phe | Lys | Cys | Tyr | His | Glu | Phe | Gly | |
| 225 | | | | | 230 | | | | | 235 | | | | | 240 | |

| act | caa | tgg | cta | cct | ctt | ttg | gag | aca | cta | cac | caa | gta | ccg | gtg | gtt | 768 |
|---|---|---|---|---|---|---|---|---|---|---|---|---|---|---|---|---|
| Thr | Gln | Trp | Leu | Pro | Leu | Leu | Glu | Thr | Leu | His | Gln | Val | Pro | Val | Val | |
| | | | | 245 | | | | | 250 | | | | | 255 | | |

| ccg | gtg | gga | tta | ctg | cca | ccg | gaa | ata | ccc | gga | gac | gag | aaa | gat | gaa | 816 |
|---|---|---|---|---|---|---|---|---|---|---|---|---|---|---|---|---|
| Pro | Val | Gly | Leu | Leu | Pro | Pro | Glu | Ile | Pro | Gly | Asp | Glu | Lys | Asp | Glu | |

```
                260              265              270
aca tgg gtg tca atc aag aaa tgg ctc gat ggt aaa caa aaa ggc agt      864
Thr Trp Val Ser Ile Lys Lys Trp Leu Asp Gly Lys Gln Lys Gly Ser
        275              280              285 gtg gtg tac gtt gca tta gga agc gag gct ttg gtg agc caa acc gag      912
Val Val Tyr Val Ala Leu Gly Ser Glu Ala Leu Val Ser Gln Thr Glu
    290              295              300 gtt gtt gag tta gca ttg ggt ctc gag ctt tct ggg ttg cca ttt gtt      960
Val Val Glu Leu Ala Leu Gly Leu Glu Leu Ser Gly Leu Pro Phe Val
305              310              315              320 tgg gct tat aga aaa cca aaa ggt ccc gcg aag tca gac tcg gtg gag     1008
Trp Ala Tyr Arg Lys Pro Lys Gly Pro Ala Lys Ser Asp Ser Val Glu
            325              330              335 ttg cca gac ggg ttc gtg gaa cga act cgt gac cgt ggg ttg gtc tgg     1056
Leu Pro Asp Gly Phe Val Glu Arg Thr Arg Asp Arg Gly Leu Val Trp
        340              345              350 acg agt tgg gca cct cag tta cga ata ctg agc cat gag tcg gtt tgt     1104
Thr Ser Trp Ala Pro Gln Leu Arg Ile Leu Ser His Glu Ser Val Cys
    355              360              365 ggt ttc ttg act cat tgt ggt tct gga tca att gtg gaa ggg cta atg     1152
Gly Phe Leu Thr His Cys Gly Ser Gly Ser Ile Val Glu Gly Leu Met
370              375              380 ttt ggt cac cct cta atc atg cta ccg ctt ttt ggg gac caa cct ctg     1200
Phe Gly His Pro Leu Ile Met Leu Pro Leu Phe Gly Asp Gln Pro Leu
385              390              395              400 aat gct cga tta ctg gag gac aaa cag gtg gga atc gag ata cca aga     1248
Asn Ala Arg Leu Leu Glu Asp Lys Gln Val Gly Ile Glu Ile Pro Arg
            405              410              415 aat gag gaa gat ggt tgc ttg acc aag gag tcg gtt gct aga tca ctg     1296
Asn Glu Glu Asp Gly Cys Leu Thr Lys Glu Ser Val Ala Arg Ser Leu
        420              425              430 agg tcc gtt gtt gtg gaa aac gaa ggg gag atc tac aag gcg aac gcg     1344
Arg Ser Val Val Val Glu Asn Glu Gly Glu Ile Tyr Lys Ala Asn Ala
    435              440              445 agg gag ctg agt aaa atc tat aac gac act aag gtg gaa aaa gaa tat     1392
Arg Glu Leu Ser Lys Ile Tyr Asn Asp Thr Lys Val Glu Lys Glu Tyr
450              455              460 gta agc caa ttc gta gac ttt ttg gaa aag aat gcg cgt gcg gtt gcc     1440
Val Ser Gln Phe Val Asp Phe Leu Glu Lys Asn Ala Arg Ala Val Ala
465              470              475              480 atc gat cat gag agt taa                                             1458
Ile Asp His Glu Ser
            485

<210> SEQ ID NO 2
<211> LENGTH: 485
<212> TYPE: PRT
<213> ORGANISM: Stevia rebaudiana

<400> SEQUENCE: 2

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
```

-continued

```
             65                  70                  75                  80
Leu Thr Leu Pro Arg Val Gln Glu Leu Pro Glu Asp Ala Glu Ala Thr
                 85                  90                  95

Thr Asp Val His Pro Glu Asp Ile Pro Tyr Leu Lys Lys Ala Ser Asp
                100                 105                 110

Gly Leu Gln Pro Glu Val Thr Arg Phe Leu Glu Gln His Ser Pro Asp
                115                 120                 125

Trp Ile Ile Tyr Asp Tyr Thr His Tyr Trp Leu Pro Ser Ile Ala Ala
130                 135                 140

Ser Leu Gly Ile Ser Arg Ala His Phe Ser Val Val Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
                180                 185                 190

Phe Pro Thr Lys Val Cys Trp Arg Lys His Asp Leu Ala Arg Leu Val
                195                 200                 205

Pro Tyr Lys Ala Pro Gly Ile Ser Asp Gly Tyr Arg Met Gly Leu Val
                210                 215                 220

Leu Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
                245                 250                 255

Pro Val Gly Leu Leu Pro Pro Glu Ile Pro Gly Asp Glu Lys Asp Glu
                260                 265                 270

Thr Trp Val Ser Ile Lys Lys Trp Leu Asp Gly Lys Gln Lys Gly Ser
                275                 280                 285

Val Val Tyr Val Ala Leu Gly Ser Glu Ala Leu Val Ser Gln Thr Glu
                290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
                340                 345                 350

Thr Ser Trp Ala Pro Gln Leu Arg Ile Leu Ser His Glu Ser Val Cys
                355                 360                 365

Gly Phe Leu Thr His Cys Gly Ser Gly Ser Ile Val Glu Gly Leu Met
                370                 375                 380

Phe Gly His Pro Leu Ile Met Leu Pro Leu Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
                420                 425                 430

Arg Ser Val Val Val Glu Asn Glu Gly Glu Ile Tyr Lys Ala Asn Ala
                435                 440                 445

Arg Glu Leu Ser Lys Ile Tyr Asn Asp Thr Lys Val Glu Lys Glu Tyr
                450                 455                 460

Val Ser Gln Phe Val Asp Phe Leu Glu Lys Asn Ala Arg Ala Val Ala
465                 470                 475                 480

Ile Asp His Glu Ser
                485
```

<210> SEQ ID NO 3
<211> LENGTH: 1458
<212> TYPE: DNA
<213> ORGANISM: Stevia rebaudiana
<220> FEATURE:
<221> NAME/KEY: CDS
<222> LOCATION: (1)..(1458)

<400> SEQUENCE: 3

```
atg tac aac gtt act tat cat caa aat tca aaa gca atg gct acc agt      48
Met Tyr Asn Val Thr Tyr His Gln Asn Ser Lys Ala Met Ala Thr Ser
1               5                   10                  15 gac tcc ata gtt gac gac cgt aag cag ctt cat gtt gcg acg ttc cca      96
Asp Ser Ile Val Asp Asp Arg Lys Gln Leu His Val Ala Thr Phe Pro
            20                  25                  30 tgg ctt gct ttc ggt cac atc ctc cct tac ctt cag ctt tcg aaa ttg     144
Trp Leu Ala Phe Gly His Ile Leu Pro Tyr Leu Gln Leu Ser Lys Leu
        35                  40                  45 ata gct gaa aag ggt cac aaa gtc tcg ttt ctt tct acc acc aga aac     192
Ile Ala Glu Lys Gly His Lys Val Ser Phe Leu Ser Thr Thr Arg Asn
    50                  55                  60 att caa cgt ctc tct tct cat atc tcg cca ctc ata aat gtt gtt caa     240
Ile Gln Arg Leu Ser Ser His Ile Ser Pro Leu Ile Asn Val Val Gln
65                  70                  75                  80 ctc aca ctt cca cgt gtc caa gag ctg ccg gag gat gca gag gcg acc     288
Leu Thr Leu Pro Arg Val Gln Glu Leu Pro Glu Asp Ala Glu Ala Thr
                85                  90                  95 act gac gtc cac cct gaa gat att cca tat ctc aag aag gct tct gat     336
Thr Asp Val His Pro Glu Asp Ile Pro Tyr Leu Lys Lys Ala Ser Asp
            100                 105                 110 ggt ctt caa ccg gag gtc acc cgg ttt cta gaa caa cac tct ccg gac     384
Gly Leu Gln Pro Glu Val Thr Arg Phe Leu Glu Gln His Ser Pro Asp
        115                 120                 125 tgg att att tat gat tat act cac tac tgg ttg cca tcc atc gcg gct     432
Trp Ile Ile Tyr Asp Tyr Thr His Tyr Trp Leu Pro Ser Ile Ala Ala
    130                 135                 140 agc ctc ggt atc tca cga gcc cac ttc tcc gtc acc act cca tgg gcc     480
Ser Leu Gly Ile Ser Arg Ala His Phe Ser Val Thr Thr Pro Trp Ala
145                 150                 155                 160 att gct tat atg gga ccc tca gct gac gcc atg ata aat ggt tca gat     528
Ile Ala Tyr Met Gly Pro Ser Ala Asp Ala Met Ile Asn Gly Ser Asp
                165                 170                 175 ggt cga acc acg gtt gag gat ctc acg aca ccg ccc aag tgg ttt ccc     576
Gly Arg Thr Thr Val Glu Asp Leu Thr Thr Pro Pro Lys Trp Phe Pro
            180                 185                 190 ttt ccg acc aaa gta tgc tgg cgg aag cat gat ctt gcc cga ctg gtg     624
Phe Pro Thr Lys Val Cys Trp Arg Lys His Asp Leu Ala Arg Leu Val
        195                 200                 205 cct tac aaa gct ccg ggg ata tct gat gga tac cgt atg ggg ctg gtt     672
Pro Tyr Lys Ala Pro Gly Ile Ser Asp Gly Tyr Arg Met Gly Leu Val
    210                 215                 220 ctt aag gga tct gat tgt ttg ctt tcc aaa tgt tac cat gag ttt gga     720
Leu Lys Gly Ser Asp Cys Leu Leu Ser Lys Cys Tyr His Glu Phe Gly
225                 230                 235                 240 act caa tgg cta cct ctt ttg gag aca cta cac caa gta ccg gtg gtt     768
Thr Gln Trp Leu Pro Leu Leu Glu Thr Leu His Gln Val Pro Val Val
                245                 250                 255 ccg gtg gga tta ctg cca ccg gaa ata ccc gga gac gag aaa gat gaa     816
Pro Val Gly Leu Leu Pro Pro Glu Ile Pro Gly Asp Glu Lys Asp Glu
            260                 265                 270
```

```
aca tgg gtg tca atc aag aaa tgg ctc gat ggt aaa caa aaa ggc agt      864
Thr Trp Val Ser Ile Lys Lys Trp Leu Asp Gly Lys Gln Lys Gly Ser
            275                 280                 285 gtg gtg tac gtt gca tta gga agc gag gtt ttg gtg agc caa acc gag      912
Val Val Tyr Val Ala Leu Gly Ser Glu Val Leu Val Ser Gln Thr Glu
            290                 295                 300 gtt gtt gag tta gca ttg ggt ctc gag ctt tct ggg ttg cca ttt gtt      960
Val Val Glu Leu Ala Leu Gly Leu Glu Leu Ser Gly Leu Pro Phe Val
305                 310                 315                 320 tgg gct tat aga aaa cca aaa ggt ccc gcg aag tca gac tcg gtg gag     1008
Trp Ala Tyr Arg Lys Pro Lys Gly Pro Ala Lys Ser Asp Ser Val Glu
            325                 330                 335 ttg cca gac ggg ttc gtg gaa cga act cgt gac cgt ggg ttg gtc tgg     1056
Leu Pro Asp Gly Phe Val Glu Arg Thr Arg Asp Arg Gly Leu Val Trp
            340                 345                 350 acg agt tgg gca cct cag tta cga ata ctg agc cat gag tcg gtt tgt     1104
Thr Ser Trp Ala Pro Gln Leu Arg Ile Leu Ser His Glu Ser Val Cys
            355                 360                 365 ggt ttc ttg act cat tgt ggt tct gga tca att gtg gaa ggg cta atg     1152
Gly Phe Leu Thr His Cys Gly Ser Gly Ser Ile Val Glu Gly Leu Met
            370                 375                 380 ttt ggt cac cct cta atc atg cta ccg att ttt ggg gac caa cct ctg     1200
Phe Gly His Pro Leu Ile Met Leu Pro Ile Phe Gly Asp Gln Pro Leu
385                 390                 395                 400 aat gct cga tta ctg gag gac aaa cag gtg gga atc gag ata cca aga     1248
Asn Ala Arg Leu Leu Glu Asp Lys Gln Val Gly Ile Glu Ile Pro Arg
            405                 410                 415 aat gag gaa gat ggt tgc ttg acc aag gag tcg gtt gct aga tca ctg     1296
Asn Glu Glu Asp Gly Cys Leu Thr Lys Glu Ser Val Ala Arg Ser Leu
            420                 425                 430 agg tcc gtt gtt gtg gaa aaa gaa ggg gag atc tac aag gcg aac gcg     1344
Arg Ser Val Val Val Glu Lys Glu Gly Glu Ile Tyr Lys Ala Asn Ala
            435                 440                 445 agg gag ctg agt aaa atc tat aac gac act aag gtt gaa aaa gaa tat     1392
Arg Glu Leu Ser Lys Ile Tyr Asn Asp Thr Lys Val Glu Lys Glu Tyr
450                 455                 460 gta agc caa ttc gta gac tat ttg gaa aag aat gcg cgt gcg gtt gcc     1440
Val Ser Gln Phe Val Asp Tyr Leu Glu Lys Asn Ala Arg Ala Val Ala
465                 470                 475                 480 atc gat cat gag agt taa                                             1458
Ile Asp His Glu Ser
            485

<210> SEQ ID NO 4
<211> LENGTH: 485
<212> TYPE: PRT
<213> ORGANISM: Stevia rebaudiana

<400> SEQUENCE: 4

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Tyr Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80
```

```
Leu Thr Leu Pro Arg Val Gln Glu Leu Pro Glu Asp Ala Glu Ala Thr
                85                  90                  95

Thr Asp Val His Pro Glu Asp Ile Pro Tyr Leu Lys Lys Ala Ser Asp
            100                 105                 110

Gly Leu Gln Pro Glu Val Thr Arg Phe Leu Glu Gln His Ser Pro Asp
            115                 120                 125

Trp Ile Ile Tyr Asp Tyr Thr His Tyr Trp Leu Pro Ser Ile Ala Ala
130                 135                 140

Ser Leu Gly Ile Ser Arg Ala His Phe Ser Val Thr Thr Pro Trp Ala
145                 150                 155                 160

Ile Ala Tyr Met Gly Pro Ser Ala Asp Ala Met Ile Asn Gly Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Leu Val
            195                 200                 205

Pro Tyr Lys Ala Pro Gly Ile Ser Asp Gly Tyr Arg Met Gly Leu Val
            210                 215                 220

Leu Lys Gly Ser Asp Cys Leu Leu Ser Lys Cys Tyr His Glu Phe Gly
225                 230                 235                 240

Thr Gln Trp Leu Pro Leu Leu Glu Thr Leu His Gln Val Pro Val Val
            245                 250                 255

Pro Val Gly Leu Leu Pro Pro Glu Ile Pro Gly Asp Glu Lys Asp Glu
            260                 265                 270

Thr Trp Val Ser Ile Lys Lys Trp Leu Asp Gly Lys Gln Lys Gly Ser
            275                 280                 285

Val Val Tyr Val Ala Leu Gly Ser Glu Val Leu Val Ser Gln Thr Glu
            290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
                325                 330                 335

Leu Pro Asp Gly Phe Val Glu Arg Thr Arg Asp Arg Gly Leu Val Trp
            340                 345                 350

Thr Ser Trp Ala Pro Gln Leu Arg Ile Leu Ser His Glu Ser Val Cys
            355                 360                 365

Gly Phe Leu Thr His Cys Gly Ser Gly Ser Ile Val Glu Gly Leu Met
            370                 375                 380

Phe Gly His Pro Leu Ile Met Leu Pro Ile Phe Gly Asp Gln Pro Leu
385                 390                 395                 400

Asn Ala Arg Leu Leu Glu Asp Lys Gln Val Gly Ile Glu Ile Pro Arg
                405                 410                 415

Asn Glu Glu Asp Gly Cys Leu Thr Lys Glu Ser Val Ala Arg Ser Leu
            420                 425                 430

Arg Ser Val Val Glu Lys Glu Gly Glu Ile Tyr Lys Ala Asn Ala
            435                 440                 445

Arg Glu Leu Ser Lys Ile Tyr Asn Asp Thr Lys Val Glu Lys Glu Tyr
            450                 455                 460

Val Ser Gln Phe Val Asp Tyr Leu Glu Lys Asn Ala Arg Ala Val Ala
465                 470                 475                 480

Ile Asp His Glu Ser
            485
```

```
<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgccgcgcgg cagccatatg tacaacgtta cttatcatc                                39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gttagcagcc ggatccttaa ctctcatgat cgatggcaa                                39

<210> SEQ ID NO 7
<211> LENGTH: 1446
<212> TYPE: DNA
<213> ORGANISM: Stevia rebaudiana
<220> FEATURE:
<221> NAME/KEY: CDS
<222> LOCATION: (1)..(1446)

<400> SEQUENCE: 7
```

| | | | | | | | | | | | | | | | | |
|---|---|---|---|---|---|---|---|---|---|---|---|---|---|---|---|---|
| atg | gat | gca | atg | gct | aca | act | gag | aag | aaa | cca | cac | gtc | atc | ttc | ata | 48 |
| Met | Asp | Ala | Met | Ala | Thr | Thr | Glu | Lys | Lys | Pro | His | Val | Ile | Phe | Ile | |
| 1 | | | | 5 | | | | | 10 | | | | | 15 | | |
| cca | ttt | cca | gca | caa | agc | cac | att | aaa | gcc | atg | ctc | aaa | cta | gca | caa | 96 |
| Pro | Phe | Pro | Ala | Gln | Ser | His | Ile | Lys | Ala | Met | Leu | Lys | Leu | Ala | Gln | |
| | | | 20 | | | | | 25 | | | | | 30 | | | |
| ctt | ctc | cac | cac | aaa | gga | ctc | cag | ata | acc | ttc | gtc | aac | acc | gac | ttc | 144 |
| Leu | Leu | His | His | Lys | Gly | Leu | Gln | Ile | Thr | Phe | Val | Asn | Thr | Asp | Phe | |
| | | | 35 | | | | | 40 | | | | | 45 | | | |
| atc | cac | aac | cag | ttt | ctt | gaa | tca | tcg | ggc | cca | cat | tgt | ttg | gac | ggt | 192 |
| Ile | His | Asn | Gln | Phe | Leu | Glu | Ser | Ser | Gly | Pro | His | Cys | Leu | Asp | Gly | |
| | 50 | | | | | 55 | | | | | 60 | | | | | |
| tca | ccg | ggt | ttc | cgg | ttc | gaa | acc | atc | ccg | gat | ggt | gtt | tct | cac | agt | 240 |
| Ser | Pro | Gly | Phe | Arg | Phe | Glu | Thr | Ile | Pro | Asp | Gly | Val | Ser | His | Ser | |
| 65 | | | | | 70 | | | | | 75 | | | | | 80 | |
| ccg | gaa | gcg | agc | atc | cca | atc | aga | gaa | tca | ctc | ttg | aga | tcc | att | gaa | 288 |
| Pro | Glu | Ala | Ser | Ile | Pro | Ile | Arg | Glu | Ser | Leu | Leu | Arg | Ser | Ile | Glu | |
| | | | | 85 | | | | | 90 | | | | | 95 | | |
| acc | aac | ttc | ttg | gat | cgt | ttc | att | gat | ctt | gta | acc | aaa | ctt | ccg | gat | 336 |
| Thr | Asn | Phe | Leu | Asp | Arg | Phe | Ile | Asp | Leu | Val | Thr | Lys | Leu | Pro | Asp | |
| | | | 100 | | | | | 105 | | | | | 110 | | | |
| cct | ccg | act | tgt | att | atc | tca | gat | ggg | ttc | ttg | tcg | gtt | tca | aca | att | 384 |
| Pro | Pro | Thr | Cys | Ile | Ile | Ser | Asp | Gly | Phe | Leu | Ser | Val | Phe | Thr | Ile | |
| | | | 115 | | | | | 120 | | | | | 125 | | | |
| gac | gct | gca | aaa | aag | ctt | gga | att | ccg | gtc | atg | atg | tat | tgg | aca | ctt | 432 |
| Asp | Ala | Ala | Lys | Lys | Leu | Gly | Ile | Pro | Val | Met | Met | Tyr | Trp | Thr | Leu | |
| | 130 | | | | | 135 | | | | | 140 | | | | | |
| gct | gcc | tgt | ggg | ttc | atg | ggt | ttt | tac | cat | att | cat | tct | ctc | att | gag | 480 |
| Ala | Ala | Cys | Gly | Phe | Met | Gly | Phe | Tyr | His | Ile | His | Ser | Leu | Ile | Glu | |
| 145 | | | | | 150 | | | | | 155 | | | | | 160 | |
| aaa | gga | ttt | gca | cca | ctt | aaa | gat | gca | agt | tac | ttg | aca | aat | ggg | tat | 528 |
| Lys | Gly | Phe | Ala | Pro | Leu | Lys | Asp | Ala | Ser | Tyr | Leu | Thr | Asn | Gly | Tyr | |

|     |     |     |     |     |     |     |     |     |     |     |     |     |     |     |     |     |
|---|---|---|---|---|---|---|---|---|---|---|---|---|---|---|---|---|
| ttg | gac | acc | gtc | att | gat | tgg | gtt | ccg | gga | atg | gaa | ggc | atc | cgt | ctc | 576 |
| Leu | Asp | Thr | Val | Ile | Asp | Trp | Val | Pro | Gly | Met | Glu | Gly | Ile | Arg | Leu | |
| | | 180 | | | | | 185 | | | | | 190 | | | | |
| aag | gat | ttc | ccg | ctg | gac | tgg | agc | act | gac | ctc | aat | gac | aaa | gtt | ttg | 624 |
| Lys | Asp | Phe | Pro | Leu | Asp | Trp | Ser | Thr | Asp | Leu | Asn | Asp | Lys | Val | Leu | |
| | | | 195 | | | | | 200 | | | | | 205 | | | |
| atg | ttc | act | aca | gaa | gct | cct | caa | agg | tca | cac | aag | gtt | tca | cat | cat | 672 |
| Met | Phe | Thr | Thr | Glu | Ala | Pro | Gln | Arg | Ser | His | Lys | Val | Ser | His | His | |
| 210 | | | | | 215 | | | | | 220 | | | | | | |
| att | ttc | cac | acg | ttc | gat | gag | ttg | gag | cct | agt | att | ata | aaa | act | ttg | 720 |
| Ile | Phe | His | Thr | Phe | Asp | Glu | Leu | Glu | Pro | Ser | Ile | Ile | Lys | Thr | Leu | |
| 225 | | | | | 230 | | | | | 235 | | | | | 240 | |
| tca | ttg | agg | tat | aat | cac | att | tac | acc | atc | ggc | cca | ctg | caa | tta | ctt | 768 |
| Ser | Leu | Arg | Tyr | Asn | His | Ile | Tyr | Thr | Ile | Gly | Pro | Leu | Gln | Leu | Leu | |
| | | | | 245 | | | | | 250 | | | | | 255 | | |
| ctt | gat | caa | ata | ccc | gaa | gag | aaa | aag | caa | act | gga | att | acg | agt | ctc | 816 |
| Leu | Asp | Gln | Ile | Pro | Glu | Glu | Lys | Lys | Gln | Thr | Gly | Ile | Thr | Ser | Leu | |
| | | | 260 | | | | | 265 | | | | | 270 | | | |
| cat | gga | tac | agt | tta | gta | aaa | gaa | gaa | cca | gag | tgt | ttc | cag | tgg | ctt | 864 |
| His | Gly | Tyr | Ser | Leu | Val | Lys | Glu | Glu | Pro | Glu | Cys | Phe | Gln | Trp | Leu | |
| | | | 275 | | | | | 280 | | | | | 285 | | | |
| cag | tct | aaa | gaa | cca | aat | tcc | gtc | gtt | tat | gta | aat | ttt | gga | agt | act | 912 |
| Gln | Ser | Lys | Glu | Pro | Asn | Ser | Val | Val | Tyr | Val | Asn | Phe | Gly | Ser | Thr | |
| | 290 | | | | | 295 | | | | | 300 | | | | | |
| aca | gta | atg | tct | tta | gaa | gac | atg | acg | gaa | ttt | ggt | tgg | gga | ctt | gct | 960 |
| Thr | Val | Met | Ser | Leu | Glu | Asp | Met | Thr | Glu | Phe | Gly | Trp | Gly | Leu | Ala | |
| 305 | | | | | 310 | | | | | 315 | | | | | 320 | |
| aat | agc | aac | cat | tat | ttc | ctt | tgg | atc | atc | cga | tca | aac | ttg | gtg | ata | 1008 |
| Asn | Ser | Asn | His | Tyr | Phe | Leu | Trp | Ile | Ile | Arg | Ser | Asn | Leu | Val | Ile | |
| | | | | 325 | | | | | 330 | | | | | 335 | | |
| ggg | gaa | aat | gca | gtt | ttg | ccc | cct | gaa | ctt | gag | gaa | cat | ata | aag | aaa | 1056 |
| Gly | Glu | Asn | Ala | Val | Leu | Pro | Pro | Glu | Leu | Glu | Glu | His | Ile | Lys | Lys | |
| | | | 340 | | | | | 345 | | | | | 350 | | | |
| aga | ggc | ttt | att | gct | agc | tgg | tgt | tca | caa | gaa | aag | gtc | ttg | aag | cac | 1104 |
| Arg | Gly | Phe | Ile | Ala | Ser | Trp | Cys | Ser | Gln | Glu | Lys | Val | Leu | Lys | His | |
| | | | 355 | | | | | 360 | | | | | 365 | | | |
| cct | tcg | gtt | gga | ggg | ttc | ttg | act | cat | tgt | ggg | tgg | gga | tcg | acc | atc | 1152 |
| Pro | Ser | Val | Gly | Gly | Phe | Leu | Thr | His | Cys | Gly | Trp | Gly | Ser | Thr | Ile | |
| | 370 | | | | | 375 | | | | | 380 | | | | | |
| gag | agc | ttg | tct | gct | ggg | gtg | cca | atg | ata | tgc | tgg | cct | tat | tcg | tgg | 1200 |
| Glu | Ser | Leu | Ser | Ala | Gly | Val | Pro | Met | Ile | Cys | Trp | Pro | Tyr | Ser | Trp | |
| 385 | | | | | 390 | | | | | 395 | | | | | 400 | |
| gac | cag | ctg | acc | aac | tgt | agg | tat | ata | tgc | aaa | gaa | tgg | gag | gtt | ggg | 1248 |
| Asp | Gln | Leu | Thr | Asn | Cys | Arg | Tyr | Ile | Cys | Lys | Glu | Trp | Glu | Val | Gly | |
| | | | | 405 | | | | | 410 | | | | | 415 | | |
| ctc | gag | atg | gga | acc | aaa | gtg | aaa | cga | gat | gaa | gtc | aag | agg | ctt | gta | 1296 |
| Leu | Glu | Met | Gly | Thr | Lys | Val | Lys | Arg | Asp | Glu | Val | Lys | Arg | Leu | Val | |
| | | | 420 | | | | | 425 | | | | | 430 | | | |
| caa | gag | ttg | atg | gga | gaa | gga | ggt | cac | aaa | atg | agg | aac | aag | gct | aaa | 1344 |
| Gln | Glu | Leu | Met | Gly | Glu | Gly | Gly | His | Lys | Met | Arg | Asn | Lys | Ala | Lys | |
| | | | 435 | | | | | 440 | | | | | 445 | | | |
| gat | tgg | aaa | gaa | aag | gct | cgc | att | gca | ata | gct | cct | aac | ggt | tca | tct | 1392 |
| Asp | Trp | Lys | Glu | Lys | Ala | Arg | Ile | Ala | Ile | Ala | Pro | Asn | Gly | Ser | Ser | |
| | 450 | | | | | 455 | | | | | 460 | | | | | |
| tct | ttg | aac | ata | gac | aaa | atg | gtc | aag | gaa | atc | acc | gtg | cta | gca | aga | 1440 |
| Ser | Leu | Asn | Ile | Asp | Lys | Met | Val | Lys | Glu | Ile | Thr | Val | Leu | Ala | Arg | |
| 465 | | | | | 470 | | | | | 475 | | | | | 480 | |
| aac | tag | | | | | | | | | | | | | | | 1446 |

Asn

<210> SEQ ID NO 8
<211> LENGTH: 481
<212> TYPE: PRT
<213> ORGANISM: Stevia rebaudiana

<400> SEQUENCE: 8

```
Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
                20                  25                  30

Leu Leu His His Lys Gly Leu Gln Ile Thr Phe Val Asn Thr Asp Phe
            35                  40                  45

Ile His Asn Gln Phe Leu Glu Ser Ser Gly Pro His Cys Leu Asp Gly
        50                  55                  60

Ser Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His
210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
        275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
            340                 345                 350

Arg Gly Phe Ile Ala Ser Trp Cys Ser Gln Glu Lys Val Leu Lys His
        355                 360                 365
```

```
Pro Ser Val Gly Gly Phe Leu Thr His Cys Gly Trp Gly Ser Thr Ile
    370                 375                 380
Glu Ser Leu Ser Ala Gly Val Pro Met Ile Cys Trp Pro Tyr Ser Trp
385                 390                 395                 400
Asp Gln Leu Thr Asn Cys Arg Tyr Ile Cys Lys Glu Trp Glu Val Gly
                405                 410                 415
Leu Glu Met Gly Thr Lys Val Lys Arg Asp Glu Val Lys Arg Leu Val
            420                 425                 430
Gln Glu Leu Met Gly Glu Gly His Lys Met Arg Asn Lys Ala Lys
        435                 440                 445
Asp Trp Lys Glu Lys Ala Arg Ile Ala Ile Ala Pro Asn Gly Ser Ser
    450                 455                 460
Ser Leu Asn Ile Asp Lys Met Val Lys Glu Ile Thr Val Leu Ala Arg
465                 470                 475                 480
Asn

<210> SEQ ID NO 9
<211> LENGTH: 1383
<212> TYPE: DNA
<213> ORGANISM: Stevia rebaudiana
<220> FEATURE:
<221> NAME/KEY: CDS
<222> LOCATION: (1)..(1383)

<400> SEQUENCE: 9 atg gcg gaa caa caa aag atc aag aaa tca cca cac gtt cta ctc atc      48
Met Ala Glu Gln Gln Lys Ile Lys Lys Ser Pro His Val Leu Leu Ile
1               5                   10                  15 cca ttc cct tta caa ggc cat ata aac cct ttc atc cag ttt ggc aaa      96
Pro Phe Pro Leu Gln Gly His Ile Asn Pro Phe Ile Gln Phe Gly Lys
            20                  25                  30 cga tta atc tcc aaa ggt gtc aaa aca aca ctt gtt acc acc atc cac     144
Arg Leu Ile Ser Lys Gly Val Lys Thr Thr Leu Val Thr Thr Ile His
        35                  40                  45 acc tta aac tca acc cta aac cac agt aac acc acc acc tcc atc         192
Thr Leu Asn Ser Thr Leu Asn His Ser Asn Thr Thr Thr Thr Ser Ile
    50                  55                  60 gaa atc caa gca att tcc gat ggt tgt gat gaa ggc ggt ttt atg agt     240
Glu Ile Gln Ala Ile Ser Asp Gly Cys Asp Glu Gly Gly Phe Met Ser
65                  70                  75                  80 gca gga gaa tca tat ttg gaa aca ttc aaa caa gtt ggg tct aaa tca     288
Ala Gly Glu Ser Tyr Leu Glu Thr Phe Lys Gln Val Gly Ser Lys Ser
                85                  90                  95 cta gct gac tta atc aag aag ctt caa agt gaa gga acc aca att gat     336
Leu Ala Asp Leu Ile Lys Lys Leu Gln Ser Glu Gly Thr Thr Ile Asp
            100                 105                 110 gca atc att tat gat tct atg act gaa tgg gtt tta gat gtt gca att     384
Ala Ile Ile Tyr Asp Ser Met Thr Glu Trp Val Leu Asp Val Ala Ile
        115                 120                 125 gag ttt gga atc gat ggt ggt tcg ttt ttc act caa gct tgt gtt gta     432
Glu Phe Gly Ile Asp Gly Gly Ser Phe Phe Thr Gln Ala Cys Val Val
    130                 135                 140 aac agc tta tat tat cat gtt cat aag ggt ttg att tct ttg cca ttg     480
Asn Ser Leu Tyr Tyr His Val His Lys Gly Leu Ile Ser Leu Pro Leu
145                 150                 155                 160 ggt gaa act gtt tcg gtt cct gga ttt cca gag ctt caa cgg tgg gag     528
Gly Glu Thr Val Ser Val Pro Gly Phe Pro Glu Leu Gln Arg Trp Glu
                165                 170                 175 aca ccg tta att ttg cag aat cat gag caa ata cag agc cct tgg tct     576
```

```
                Thr Pro Leu Ile Leu Gln Asn His Glu Gln Ile Gln Ser Pro Trp Ser
                            180                 185                 190 cag atg ttg ttt ggt cag ttt gct aat att gat caa gca cgt tgg gtc        624
Gln Met Leu Phe Gly Gln Phe Ala Asn Ile Asp Gln Ala Arg Trp Val
            195                 200                 205 ttc aca aat agt ttt tac aag ctc gag gaa gag gta ata gag tgg acg        672
Phe Thr Asn Ser Phe Tyr Lys Leu Glu Glu Glu Val Ile Glu Trp Thr
210                 215                 220 aga aag ata tgg aac ttg aag gta atc ggg cca aca ctt cca tcc atg        720
Arg Lys Ile Trp Asn Leu Lys Val Ile Gly Pro Thr Leu Pro Ser Met
225                 230                 235                 240 tac ctt gac aaa cga ctt gat gat gat aaa gat aac gga ttt aat ctc        768
Tyr Leu Asp Lys Arg Leu Asp Asp Asp Lys Asp Asn Gly Phe Asn Leu
                245                 250                 255 tac aaa gca aac cat cat gag tgc atg aac tgg tta gac gat aag cca        816
Tyr Lys Ala Asn His His Glu Cys Met Asn Trp Leu Asp Asp Lys Pro
            260                 265                 270 aag gaa tca gtt gtt tac gta gca ttt ggt agc ctg gtg aaa cat gga        864
Lys Glu Ser Val Val Tyr Val Ala Phe Gly Ser Leu Val Lys His Gly
        275                 280                 285 ccc gaa caa gtg gaa gaa atc aca cgg gct tta ata gat agt gat gtc        912
Pro Glu Gln Val Glu Glu Ile Thr Arg Ala Leu Ile Asp Ser Asp Val
    290                 295                 300 aac ttc ttg tgg gtt atc aaa cat aaa gaa gag gga aag ctc cca gaa        960
Asn Phe Leu Trp Val Ile Lys His Lys Glu Glu Gly Lys Leu Pro Glu
305                 310                 315                 320 aat ctt tcg gaa gta ata aaa acc gga aag ggt ttg att gta gca tgg       1008
Asn Leu Ser Glu Val Ile Lys Thr Gly Lys Gly Leu Ile Val Ala Trp
                325                 330                 335 tgc aaa caa ttg gat gtg tta gca cac gaa tca gta gga tgc ttt gtt       1056
Cys Lys Gln Leu Asp Val Leu Ala His Glu Ser Val Gly Cys Phe Val
            340                 345                 350 aca cat tgt ggg ttc aac tca act ctt gaa gca ata agt ctt gga gtc       1104
Thr His Cys Gly Phe Asn Ser Thr Leu Glu Ala Ile Ser Leu Gly Val
        355                 360                 365 ccc gtt gtt gca atg cct caa ttt tcg gat caa act aca aat gcc aag       1152
Pro Val Val Ala Met Pro Gln Phe Ser Asp Gln Thr Thr Asn Ala Lys
    370                 375                 380 ctt cta gat gaa att ttg ggt gtt gga gtt aga gtt aag gct gat gag       1200
Leu Leu Asp Glu Ile Leu Gly Val Gly Val Arg Val Lys Ala Asp Glu
385                 390                 395                 400 aat ggg ata gtg aga aga gga aat ctt gcg tca tgt att aag atg att       1248
Asn Gly Ile Val Arg Arg Gly Asn Leu Ala Ser Cys Ile Lys Met Ile
                405                 410                 415 atg gag gag gaa aga gga gta ata atc cga aag aat gcg gta aaa tgg       1296
Met Glu Glu Glu Arg Gly Val Ile Ile Arg Lys Asn Ala Val Lys Trp
            420                 425                 430 aag gat ttg gct aaa gta gcc gtt cat gaa ggt ggt agc tca gac aat       1344
Lys Asp Leu Ala Lys Val Ala Val His Glu Gly Gly Ser Ser Asp Asn
        435                 440                 445 gat att gtc gaa ttt gta agt gag cta att aag gct taa                   1383
Asp Ile Val Glu Phe Val Ser Glu Leu Ile Lys Ala
    450                 455                 460

<210> SEQ ID NO 10
<211> LENGTH: 460
<212> TYPE: PRT
<213> ORGANISM: Stevia rebaudiana

<400> SEQUENCE: 10
```

```
Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Glu Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

Pro Val Val Ala Met Pro Gln Phe Ser Asp Gln Thr Thr Asn Ala Lys
    370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
```

```
                420               425                 430
Lys Asp Leu Ala Lys Val Ala Val His Glu Gly Gly Ser Ser Asp Asn
            435                 440                 445

Asp Ile Val Glu Phe Val Ser Glu Leu Ile Lys Ala
            450                 455             460

<210> SEQ ID NO 11
<211> LENGTH: 1377
<212> TYPE: DNA
<213> ORGANISM: Stevia rebaudiana
<220> FEATURE:
<221> NAME/KEY: CDS
<222> LOCATION: (1)..(1377)

<400> SEQUENCE: 11 atg gaa aat aaa acg gag acc acc gtt cgc cgg cgc cgg aga ata ata        48
Met Glu Asn Lys Thr Glu Thr Thr Val Arg Arg Arg Arg Arg Ile Ile
1               5                   10                  15 tta ttc ccg gta cca ttt caa ggc cac att aac cca att ctt cag cta        96
Leu Phe Pro Val Pro Phe Gln Gly His Ile Asn Pro Ile Leu Gln Leu
                20                  25                  30 gcc aat gtg ttg tac tct aaa gga ttc agt atc acc atc ttt cac acc       144
Ala Asn Val Leu Tyr Ser Lys Gly Phe Ser Ile Thr Ile Phe His Thr
            35                  40                  45 aac ttc aac aaa ccc aaa aca tct aat tac cct cac ttc act ttc aga       192
Asn Phe Asn Lys Pro Lys Thr Ser Asn Tyr Pro His Phe Thr Phe Arg
50                  55                  60 ttc atc ctc gac aac gac cca caa gac gaa cgc att tcc aat cta ccg       240
Phe Ile Leu Asp Asn Asp Pro Gln Asp Glu Arg Ile Ser Asn Leu Pro
65                  70                  75                  80 act cat ggt ccg ctc gct ggt atg cgg att ccg att atc aac gaa cac       288
Thr His Gly Pro Leu Ala Gly Met Arg Ile Pro Ile Ile Asn Glu His
                85                  90                  95 gga gct gac gaa tta cga cgc gaa ctg gaa ctg ttg atg tta gct tct       336
Gly Ala Asp Glu Leu Arg Arg Glu Leu Glu Leu Leu Met Leu Ala Ser
            100                 105                 110 gaa gaa gat gaa gag gta tcg tgt tta atc acg gat gct ctt tgg tac       384
Glu Glu Asp Glu Glu Val Ser Cys Leu Ile Thr Asp Ala Leu Trp Tyr
        115                 120                 125 ttc gcg caa tct gtt gct gac agt ctt aac ctc cga ccg ctt gtt ttg       432
Phe Ala Gln Ser Val Ala Asp Ser Leu Asn Leu Arg Pro Leu Val Leu
    130                 135                 140 atg aca agc agc ttg ttt aat ttt cat gca cat gtt tca ctt cct cag       480
Met Thr Ser Ser Leu Phe Asn Phe His Ala His Val Ser Leu Pro Gln
145                 150                 155                 160 ttt gat gag ctt ggt tac ctc gat cct gat gac aaa acc cgt ttg gaa       528
Phe Asp Glu Leu Gly Tyr Leu Asp Pro Asp Asp Lys Thr Arg Leu Glu
                165                 170                 175 gaa caa gcg agt ggg ttt cct atg cta aaa gtg aaa gac atc aag tct       576
Glu Gln Ala Ser Gly Phe Pro Met Leu Lys Val Lys Asp Ile Lys Ser
            180                 185                 190 gcg tat tcg aac tgg caa ata ctc aaa gag ata tta ggg aag atg ata       624
Ala Tyr Ser Asn Trp Gln Ile Leu Lys Glu Ile Leu Gly Lys Met Ile
        195                 200                 205 aaa caa aca aaa gca tct tca gga gtc atc tgg aac tca ttt aag gaa       672
Lys Gln Thr Lys Ala Ser Ser Gly Val Ile Trp Asn Ser Phe Lys Glu
    210                 215                 220 ctc gaa gag tct gag ctc gaa act gtt atc cgt gag atc ccg gct cca       720
Leu Glu Glu Ser Glu Leu Glu Thr Val Ile Arg Glu Ile Pro Ala Pro
225                 230                 235                 240
```

| | | |
|---|---|---|
| agt ttc ttg ata cca ctc ccc aag cat ttg aca gcc tct tcc agc agc<br>Ser Phe Leu Ile Pro Leu Pro Lys His Leu Thr Ala Ser Ser Ser Ser<br>    245                 250                 255 | | 768 |
| tta cta gac cac gat cga acc gtt ttt caa tgg tta gac caa caa ccg<br>Leu Leu Asp His Asp Arg Thr Val Phe Gln Trp Leu Asp Gln Gln Pro<br>        260                 265                 270 | | 816 |
| cca agt tcg gta ctg tat gtt agt ttt ggt agt act agt gaa gtg gat<br>Pro Ser Ser Val Leu Tyr Val Ser Phe Gly Ser Thr Ser Glu Val Asp<br>            275                 280                 285 | | 864 |
| gag aaa gat ttc ttg gaa ata gct cgt ggg ttg gtt gat agc aag cag<br>Glu Lys Asp Phe Leu Glu Ile Ala Arg Gly Leu Val Asp Ser Lys Gln<br>        290                 295                 300 | | 912 |
| tcg ttt tta tgg gtg gtt cga cct ggg ttt gtc aag ggt tcg acg tgg<br>Ser Phe Leu Trp Val Val Arg Pro Gly Phe Val Lys Gly Ser Thr Trp<br>305                 310                 315                 320 | | 960 |
| gtc gaa ccg ttg cca gat ggg ttc ttg ggt gaa aga gga cgt att gtg<br>Val Glu Pro Leu Pro Asp Gly Phe Leu Gly Glu Arg Gly Arg Ile Val<br>                325                 330                 335 | | 1008 |
| aaa tgg gtt cca cag caa gaa gtg cta gct cat gga gca ata ggc gca<br>Lys Trp Val Pro Gln Gln Glu Val Leu Ala His Gly Ala Ile Gly Ala<br>            340                 345                 350 | | 1056 |
| ttc tgg act cat agc gga tgg aac tct acg ttg gaa agc gtt tgt gaa<br>Phe Trp Thr His Ser Gly Trp Asn Ser Thr Leu Glu Ser Val Cys Glu<br>        355                 360                 365 | | 1104 |
| ggt gtt cct atg att ttc tcg gat ttt ggg ctc gat caa ccg ttg aat<br>Gly Val Pro Met Ile Phe Ser Asp Phe Gly Leu Asp Gln Pro Leu Asn<br>    370                 375                 380 | | 1152 |
| gct aga tac atg agt gat gtt ttg aag gta ggg gtg tat ttg gaa aat<br>Ala Arg Tyr Met Ser Asp Val Leu Lys Val Gly Val Tyr Leu Glu Asn<br>385                 390                 395                 400 | | 1200 |
| ggg tgg gaa aga gga gag ata gca aat gca ata aga aga gtt atg gtg<br>Gly Trp Glu Arg Gly Glu Ile Ala Asn Ala Ile Arg Arg Val Met Val<br>                405                 410                 415 | | 1248 |
| gat gaa gaa gga gaa tac att aga cag aat gca aga gtt ttg aaa caa<br>Asp Glu Glu Gly Glu Tyr Ile Arg Gln Asn Ala Arg Val Leu Lys Gln<br>            420                 425                 430 | | 1296 |
| aag gca gat gtt tct ttg atg aag ggt ggt tcg tct tac gaa tca tta<br>Lys Ala Asp Val Ser Leu Met Lys Gly Gly Ser Ser Tyr Glu Ser Leu<br>        435                 440                 445 | | 1344 |
| gag tct cta gtt tct tac att tca tcg ttg taa<br>Glu Ser Leu Val Ser Tyr Ile Ser Ser Leu<br>    450                 455 | | 1377 |

<210> SEQ ID NO 12
<211> LENGTH: 458
<212> TYPE: PRT
<213> ORGANISM: Stevia rebaudiana

<400> SEQUENCE: 12

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

```
Thr His Gly Pro Leu Ala Gly Met Arg Ile Pro Ile Ile Asn Glu His
             85                  90                  95
Gly Ala Asp Glu Leu Arg Arg Glu Leu Glu Leu Leu Met Leu Ala Ser
            100                 105                 110
Glu Glu Asp Glu Glu Val Ser Cys Leu Ile Thr Asp Ala Leu Trp Tyr
        115                 120                 125
Phe Ala Gln Ser Val Ala Asp Ser Leu Asn Leu Arg Pro Leu Val Leu
    130                 135                 140
Met Thr Ser Ser Leu Phe Asn Phe His Ala His Val Ser Leu Pro Gln
145                 150                 155                 160
Phe Asp Glu Leu Gly Tyr Leu Asp Pro Asp Asp Lys Thr Arg Leu Glu
                165                 170                 175
Glu Gln Ala Ser Gly Phe Pro Met Leu Lys Val Lys Asp Ile Lys Ser
            180                 185                 190
Ala Tyr Ser Asn Trp Gln Ile Leu Lys Glu Ile Leu Gly Lys Met Ile
        195                 200                 205
Lys Gln Thr Lys Ala Ser Ser Gly Val Ile Trp Asn Ser Phe Lys Glu
    210                 215                 220
Leu Glu Glu Ser Glu Leu Glu Thr Val Ile Arg Glu Ile Pro Ala Pro
225                 230                 235                 240
Ser Phe Leu Ile Pro Leu Pro Lys His Leu Thr Ala Ser Ser Ser Ser
                245                 250                 255
Leu Leu Asp His Asp Arg Thr Val Phe Gln Trp Leu Asp Gln Gln Pro
            260                 265                 270
Pro Ser Ser Val Leu Tyr Val Ser Phe Gly Ser Thr Ser Glu Val Asp
        275                 280                 285
Glu Lys Asp Phe Leu Glu Ile Ala Arg Gly Leu Val Asp Ser Lys Gln
    290                 295                 300
Ser Phe Leu Trp Val Val Arg Pro Gly Phe Val Lys Gly Ser Thr Trp
305                 310                 315                 320
Val Glu Pro Leu Pro Asp Gly Phe Leu Gly Glu Arg Gly Arg Ile Val
                325                 330                 335
Lys Trp Val Pro Gln Gln Glu Val Leu Ala His Gly Ala Ile Gly Ala
            340                 345                 350
Phe Trp Thr His Ser Gly Trp Asn Ser Thr Leu Glu Ser Val Cys Glu
        355                 360                 365
Gly Val Pro Met Ile Phe Ser Asp Phe Gly Leu Asp Gln Pro Leu Asn
    370                 375                 380
Ala Arg Tyr Met Ser Asp Val Leu Lys Val Gly Val Tyr Leu Glu Asn
385                 390                 395                 400
Gly Trp Glu Arg Gly Glu Ile Ala Asn Ala Ile Arg Arg Val Met Val
                405                 410                 415
Asp Glu Glu Gly Glu Tyr Ile Arg Gln Asn Ala Arg Val Leu Lys Gln
            420                 425                 430
Lys Ala Asp Val Ser Leu Met Lys Gly Gly Ser Ser Tyr Glu Ser Leu
        435                 440                 445
Glu Ser Leu Val Ser Tyr Ile Ser Ser Leu
    450                 455

<210> SEQ ID NO 13
<211> LENGTH: 2004
<212> TYPE: DNA
<213> ORGANISM: Arabidopsis thaliana

<400> SEQUENCE: 13
```

```
atggatgata ctacgtataa gccaaagaac attctcatta ctggagctgc tggatttatt      60
gcttctcatg ttgccaacag attaatccgt aactatcctg attacaagat cgttgttctt     120
gacaagcttg attactgttc agatctgaag aatcttgatc cttcttttc ttcaccaaat     180
ttcaagtttg tcaaaggaga tatcgcgagt gatgatctcg ttaactacct tctcatcact     240
gaaaacattg atacgataat gcattttgct gctcaaactc atgttgataa ctcttttggt     300
aatagctttg agtttaccaa gaacaatatt tatggtactc atgttctttt ggaagcctgt     360
aaagttacag gacagatcag gaggtttatc catgtgagta ccgatgaagt ctatggagaa     420
accgatgagg atgctgctgt aggaaaccat gaagcttctc agctgttacc gacgaatcct     480
tactctgcaa ctaaggctgg tgctgagatg cttgtgatgg cttatggtag atcatatgga     540
ttgcctgtta ttacgactcg cgggaacaat gtttatgggc taaccagtt tcctgaaaaa     600
atgattccta agttcatctt gttggctatg agtgggaagc cgcttcccat ccatggagat     660
ggatctaatg tccggagtta cttgtactgc gaagacgttg ctgaggcttt tgaggttgtt     720
cttcacaaag gagaaatcgg tcatgtctac aatgtcggca caaaagaga aggagagtg     780
atcgatgtgg ctagagacat ctgcaaactt tcgggaaag accctgagtc aagcattcag     840
tttgtggaga accggccctt taatgatcaa aggtacttcc ttgatgatca gaagctgaag     900
aaattggggt ggcaagagcg aacaaattgg aagatggat tgaagaagac aatggactgg     960
tacactcaga atcctgagtg gtggggtgat gtttctggag ctttgcttcc tcatccgaga    1020
atgcttatga tgcccggtgg aagactttct gatggatcta gtgagaagaa agacgtttca    1080
agcaacacgg tccagacatt tacggttgta acacctaaga atggtgattc tggtgacaaa    1140
gcttcgttga gttttttgat ctatggtaag actggttggc ttggtggtct tctagggaaa    1200
ctatgtgaga agcaagggat tacatatgag tatgggaaag gacgtctgga ggatagagct    1260
tctcttgtgg cggatattcg tagcatcaaa cctactcatg tgtttaatgc tgctggttta    1320
actggcagac ccaacgttga ctggtgtgaa tctcacaaac cagagaccat tcgtgtaaat    1380
gtcgcaggta cttttgactct agctgatgtt tgcagagaga atgatctctt gatgatgaac    1440
ttcgccaccg gttgcatctt tgagtatgac gctacacatc ctgagggttc gggtataggt    1500
ttcaaggaag aagacaagcc aaatttcttt ggttctttct actcgaaaac caaagccatg    1560
gttgaggagc tcttgagaga atttgacaat gtatgtacct tgagagtccg gatgccaatc    1620
tcctcagacc taaacaaccc gagaaacttc atcacgaaga tctcgcgcta caacaaagtg    1680
gtggacatcc cgaacagcat gaccgtacta gacgagcttc tcccaatctc tatcgagatg    1740
gcgaagagaa acctaagagg catatggaat ttcaccaacc caggggtggt gagccacaac    1800
gagatattgg agatgtacaa gaattacatc gagccaggtt ttaaatggtc caacttcaca    1860
gtggaagaac aagcaaaggt cattgttgct gctcgaagca acaacgaaat ggatggatct    1920
aaactaagca aggagttccc agagatgctc tccatcaaag agtcactgct caaatacgtc    1980
tttgaaccaa acaagagaac ctaa                                            2004
```

<210> SEQ ID NO 14  
<211> LENGTH: 33  
<212> TYPE: DNA  
<213> ORGANISM: Artificial Sequence  
<220> FEATURE:  
<223> OTHER INFORMATION: Description of Artificial Sequence: Synthetic oligonucleotide

<400> SEQUENCE: 14

```
cacccatatg gatgcaatgg ctacaactga gaa                                    33
```

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
agatctctag tttcttgcta gcacggtgat tt                                     32
```

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

```
cacccatatg gcggaacaac aaaagatcaa gaaat                                  35
```

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
ggatccttaa gccttaatta gctcacttac aaatt                                  35
```

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
cacccatatg gaaaataaaa cggagacca                                         29
```

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
ggatccttac aacgatgaaa tgtaagaaac ta                                     32
```

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
acagatctat ggatgcaatg gctacaactg aga                          33

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tagtcgacta gtttcttgct agcacggtga tttc                         34

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aagcggccgc atgtacaacg ttacttatca tcaaaattca aa                 42

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cgttaattaa ctctcatgat cgatggcaac c                            31

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagcggccgc atggcggaac aacaaaagat caag                         34

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgttaattaa gccttaatta gctcacttac aaattcg                      37

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaggatccat ggaaaataaa acggagacca ccg                          33

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgtcgactt acaacgatga aatgtaagaa actagagact ctaa                    44

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggatccatgg atgatactac gtataagcca aag                                33

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ctcgagttag gttctcttgt ttggttcaaa ga                                 32

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
caagtcccca accaaattcc gt                                            22

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cacgaacccg tctggcaact c                                             21

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cccgtgtgat ttcttccact tgttc                                         25

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
caagaaccca tctggcaacg g                                              21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gctttgtcac cagaatcacc att                                            23

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gattattaaa cttctttgcg tccatcca                                       28

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cctctatact ttaacgtcaa ggagaaaaaa cc                                  32

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tgccgcgcgg cagccatatg tacaacgtta cttatcatc                           39

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gttagcagcc ggatccttaa ctctcatgat cgatggcaa                           39

```
<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cacttctccg tcgtcactcc atg                                              23

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
catggagtga cgacggagaa gtg                                              23

<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cacttctccg tcaccactcc atg                                              23

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
catggagtgg tgacggagaa gtg                                              23

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ctgattgttt gcttttcaaa tgttaccatg ag                                    32

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctcatggtaa catttgaaaa gcaaacaatc ag                                    32

<210> SEQ ID NO 45
```

```
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctgattgttt gctttccaaa tgttaccatg ag                                    32

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctcatggtaa catttggaaa gcaaacaatc ag                                    32
```

STEVIOL GLYCOSIDE HEXOSE TRANSFERASE AND GENE CODING FOR SAME

SEQUENCE LISTING

The instant application contains a Sequence Listing which has been filed electronically in ASCII format and is hereby incorporated by reference in its entirety. Said ASCII copy, created on Sep. 27, 2019, is named P57761 SL.txt and is 67,082 bytes in size.

TECHNICAL FIELD

The present invention relates to a protein having the activity to transfer hexose to a steviol glycoside and a polynucleotide encoding this, a method of producing a steviol glycoside using the protein, a transformant that highly expresses a steviol glycosyltransferase, and a steviol glycoside made by the method and use thereof.

BACKGROUND ART

The leaves of *Stevia rebaudiana* of the family Asteraceae contain a secondary metabolite called "steviol" which is a kind of diterpenoid. Some steviol glycosides have sweetness about 300 times higher than that of sucrose and are therefore used as non-caloric sweeteners in the food industry. Obesity is becoming more of a serious social issue on an international scale, and non-caloric sweeteners are increasingly demanded from the viewpoint of promotion of health and reduction of medical cost. Currently, aspartame and acesulfame potassium, which are artificially-synthesized amino acid derivatives, are used as artificial sweeteners. However, naturally-occurring non-caloric sweeteners such as steviol glycosides are expected to be safer and gain more public acceptance.

The main steviol glycosides in *Stevia rebaudiana* are modified with sugar finally into a glycoside called Rebaudioside A (Reb.A) having 4 sugars attached (FIG. 1). Its precursor stevioside, which is a trisaccharide glycoside, is most abundant and these 2 are central substances of the sweetness of *Stevia rebaudiana*. It is known that the stevioside content is highest in the leaves of *Stevia rebaudiana* and it exhibits sweetness about 250 to 300 times higher than that of sucrose. Reb.A is very sweet (350 to 450 times of that of sucrose) and is a tetrasaccharide glycoside, which is said to have good quality of taste. These have attracted attention as non-caloric sweeteners. In addition to these glycosides, glycosides considered to be reaction intermediates and analogs differing in the type of sugar are known to exist. For example, while the 4 glycoside sugars in Reb.A are all glucose, Rebaudioside C (Reb.C), in which rhamnose instead of glucose is added at position 2 of glucose at position 13, and Rebaudioside F (Reb.F), in which xylose was added at the same position, are known.

The genes of enzymes for bio-synthesis of Reb.A have been isolated by the Expressed Sequence Tag (EST) analysis of *Stevia rebaudiana* (Non-Patent Literature 1 and 2, Patent Literature 1). Ent-kaurenoic acid, which is a precursor of gibberellin, a plant hormone diterpenoid, is hydroxylated at position 13 by ent-kaurenoic acid 13-hydroxylase (EK13H) to produce steviol (FIG. 2) (Patent Literature 1). Steviol is first glucosylated at the hydroxyl group at position 13 by UGT85C2, a UDP sugar-dependent glycosyltransferase (UGT) in *Stevia rebaudiana* to produce steviolmonoside (Non-Patent Literature 1, 2). Steviolmonoside is further glucosylated at position 2 of glucose at position 13 to produce steviolbioside or glucosylated at the carboxyl group at position 19 to produce a disaccharide glycoside of steviol called rubusoside. As an enzyme that glucosylates steviolmonoside or rubusoside at position 2 of glucose at position 13, UGT91D2 has been reported (Non-Patent Literature 2: in the report, UGT91D2 is referred to as UGT91D-like 3). Meanwhile, position 3 of glucose at position 13 and carboxylic acid at position 19 have been reported to be glucosylated by UGT76G1 and UGT74G1, respectively (Non-Patent Literature 2). As described above, the genes of enzymes responsible for glycosylation to Reb.A have been identified and the industrial use of *Stevia rebaudiana* enzymes is in progress, as seen in the report of ectopic expression of biosynthetic enzymes for steviol glycosides in yeast and production of the steviol glycosides in culture (Patent Literature 3). Meanwhile, the UGT enzymes responsible for the biosynthesis of Reb.C and Reb.F, which comprise a glycoside sugar other than glucose, are not elucidated.

CITATION LIST

Patent Literature

Patent Literature 1: EP 1 897 951 B1
Patent Literature 2: WO2013/137487
Patent Literature 3: WO2014 122328

Non-Patent Literature

Non-Patent Literature 1: Brandle and Telmer (2007) Phytochemistry 68, 1855-1863
Non-Patent Literature 2: Richman et al (2005) Plant J. 41, 56-67

SUMMARY OF INVENTION

Technical Problem

An object of the present invention is to provide a steviol glycoside hexose transferase and a method of producing a steviol glycoside comprising glucose and/or rhamnose using the enzyme.

Solution to Problem

The present inventors have succeeded, as a result of diligent studies for achieving the aforementioned object, in identifying the enzyme UGT91D2L #16, which catalyzes the reaction of adding rhamnose to rubusoside, a steviol glycoside, at position 2 of glucose at position 13 in *Stevia rebaudiana*, and a genetic sequence encoding the protein. It was also found that the enzyme UGT91D2L #16 catalyzes the transfer of glucose.

Moreover, the present inventors have identified the amino acid residues that are actually involved in the selection of the sugar donor among the 7 amino acid mutations between the glucose transferase (UGT91D2) and the rhamnose transferase (UGT91D2L #16) for steviol glycosides in *Stevia rebaudiana* through the homology model analysis and the evaluation of mutant proteins.

The present invention is based on the findings.

Advantageous Effects of Invention

By using the enzyme according to the present invention, it is possible to provide a steviol glycoside hexose transferase and a method of producing a steviol glycoside comprising glucose and/or rhamnose using the enzyme. Moreover, by promoting or inhibiting the function of the enzyme according to the present invention, the kind of steviol glycoside that is expressed in the plant of Stevia rebaudiana can be controlled.

Furthermore, it is possible to select individuals containing a particular steviol glycoside and to produce steviol glycosides containing glucose and/or rhamnose by metabolic engineering, based on the sequence and the expression level of the gene of the enzyme.

Moreover, more highly glycosylated steviol glycosides (for example, Rebaudioside C, N, and O) can be produced by coexpressing the protein according to the present invention and a polynucleotide encoding the protein with another steviol glycoside hexose transferase or a polynucleotide encoding the enzyme in the same host cells.

Furthermore, by using the present invention, it is possible to efficiently design the sugar donor-selectivity of UGT and estimate the activity of a natural UGT and the glycoside sugar of an accumulated metabolite. Moreover, by specifically substituting one or more amino acid residues involved in the selection of sugar donor identified in the present invention by a genome editing technique, etc. it can be applied to controlling not only rhamnose-containing steviol glycosides such as Reb.C but also glycoside sugars of plant secondary metabolites.

BRIEF DESCRIPTION OF DRAWINGS

FIG. 1 illustrates the names and structures of the steviol glycosides. In FIG. 1, "Glc-Glc" (β 2→1) indicates that the binding of "Glc-Glc" is a β2,1 glycosidic linkage and "Glc-Glc" (β 3→1) indicates that the binding of "Glc-Glc" is a β3,1 glycosidic linkage.

FIG. 2 illustrates the biosynthetic pathway of steviol glycosides.

FIG. 3 illustrates a result of electrophoresis of PCR products in a 0.8% agarose gel and ethidium bromide staining.

FIG. 4 illustrates results of Western Blotting and SDS-PAGE of the Stevia rebaudiana UGT protein expressed in Escherichia coli.

FIG. 5-1 illustrates the activity to glucosylate rubusoside to generate stevioside in a negative control section.

FIG. 5-2 illustrates the activity to glucosylate rubusoside to generate stevioside in SrUGT91D2.

FIG. 5-3 illustrates the activity to glucosylate rubusoside to generate stevioside in SrUGT91D2L #16.

FIG. 6-1 illustrates the activity to rhamnosylate rubusoside to produce dulcoside A in a negative control section.

FIG. 6-2 illustrates the activity to rhamnosylate rubusoside to produce dulcoside A in SrUGT91D2.

FIG. 6-3 illustrates the activity to rhamnosylate rubusoside to produce dulcoside A in SrUGT91D2L #16.

FIG. 7 illustrates the specific activities of UGT91D2 and UGT91D2L #16 for glucosylation and rhamnosylation of rubusoside.

FIG. 8 illustrates the glycosylation pathway of steviol glycosides using UGT91D2 and UGT91D2L #16.

FIG. 9 illustrates results of the HPLC analysis of steviol glycosides obtained by the production of steviol glycosides in yeast (the amount of steviol added: 0.5 μg/ml).

FIG. 10 illustrates results of the HPLC analysis of steviol glycosides obtained by the production of steviol glycosides in yeast (the amount of steviol added: 2 μg/ml). In FIG. 10, RebC represents Rebaudioside C, SteE represents steviol monoglucosyl ester, and SteM represents steviol monoglucoside.

FIG. 11 illustrates LC-MS results indicating the amount of Reb.C produced in the strains A-5678 and A-56R78 at an amount of steviol added of 2 μg/ml.

FIG. 12 illustrates a homology model of UGT91D2 bound with UDP-glucose.

FIG. 13 is an enlarged view of the part in the frame in FIG. 12. The figure illustrates the positional relation between UDP-glucose (UDP-Glc) and the 156th amino acid (Thr156) and the 233rd amino acid (Ser233) adjacent thereto.

FIG. 14 is a graph illustrating a comparison of in vitro glycosylation activity (A) and rhamnosylation activity (B) of wild-type UGT91D2 and Mutant 1 expressed in Escherichia coli and a comparison of in vitro glucosylation activity (C) and rhamnosylation activity (D) of wild-type UGT91D2L #16 and Mutant 2. The numerical values indicate the relative activity of Mutant 1 or 2 with that of wild-type UGT91D2 or wild-type UGT91D2L #16 being 100%.

FIG. 15 is a graph illustrating a comparison of glucosylation activity (A) and rhamnosylation activity (B to D) of wild-type UGT91D2, wild-type UGT91D2L #16, and Mutants 1 to 6 in the yeast in which various UGTs are introduced. The numerical values indicate the signal intensity of the products as measured by LC-MS.

DESCRIPTION OF EMBODIMENTS

The present invention will be described in detail below. The following embodiments are illustrations for describing the present invention and it is not intended to limit the present invention to only these embodiments. The present invention can be embodied in various forms that do not deviates from the spirit of the present invention. All literature and patent literature such as unexamined patent publications and patent publications cited herein are incorporated herein by reference.

The present inventors have for the first time elucidated that the enzyme proteins are UGT91D2 and UGT91D2L #16 that are responsible for glucose- and/or rhamnose-addition reaction at position 2 of glucose at position 13 in steviol glycosides. The CDSs and the estimated amino acid sequences of UGT91D2 and UGT91D2L #16 are SEQ ID NOs: 1 to 4, respectively. These polynucleotides and enzymes can be obtained by the techniques described in Examples below, known genetic engineering techniques, known synthetic methods, and the like.

1. Steviol Glycoside Hexose Transferase

The present invention provides a protein (hereinafter, referred to as the "protein according to the present invention") according to any one selected from the group consisting of the following (a) to (c):

(a) a protein consisting of the amino acid sequence of SEQ ID NO: 2;

(b) a protein consisting of an amino acid sequence wherein 1 to 48 amino acids other than the amino acid residue $X_7$ are deleted, substituted, inserted, and/or added in the amino acid sequence of SEQ ID NO: 2 and having an activity to add hexose at position 2 of glucose at position 13 in a compound represented by the following formula (I);

(c) a protein having an amino acid sequence having a sequence identity of 90% or more to the amino acid sequence of SEQ ID NO: 2 wherein an amino acid corresponding to the amino acid residue $X_7$ is the same and having an activity to add hexose at position 2 of glucose at position 13 in a compound represented by the following formula (I);

[Formula 1]

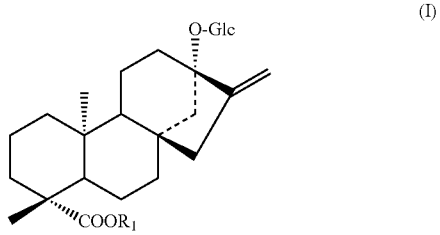

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a ($C_3$-$C_{10}$ cycloalkyl)$C_1$-$C_{10}$ alkyl group or a sugar residue.

According to another embodiment, the protein according to the present invention is (b') a protein consisting of an amino acid sequence wherein 1 to 48 amino acids other than the amino acid residues $X_1$ to $X_7$ are deleted, substituted, inserted, and/or added in the amino acid sequence of SEQ ID NO: 2 and having an activity to add hexose at position 2 of glucose at position 13 in a compound represented by formula (I) above; or (c') a protein having an amino acid sequence having a sequence identity of 90% or more to the amino acid sequence of SEQ ID NO: 2 wherein amino acids corresponding to the amino acid residues $X_1$ to $X_7$ are the same and having an activity to add hexose at position 2 of glucose at position 13 in a compound represented by formula (I) above.

According to another embodiment, the protein according to the present invention is (b") a protein consisting of an amino acid sequence wherein 1 to 48 amino acids other than the amino acid residues $X_2$ and/or $X_3$ are deleted, substituted, inserted, and/or added in the amino acid sequence of SEQ ID NO: 2 and having an activity to add hexose at position 2 of glucose at position 13 in a compound represented by formula (I) above; or (c") a protein having an amino acid sequence having a sequence identity of 90% or more to the amino acid sequence of SEQ ID NO: 2 wherein amino acids corresponding to the amino acid residues $X_2$ and/or $X_3$ are the same and having an activity to add hexose at position 2 of glucose at position 13 in a compound represented by formula (I) above.

According to another embodiment, the protein according to the present invention is (d) a protein consisting of an amino acid sequence wherein the 156th amino acid residue is Val and/or the 233rd amino acid residue is Phe in the amino acid sequence of SEQ ID NO: 4; or (e) a protein consisting of an amino acid sequence wherein 1 to 48 amino acids are deleted, substituted, inserted, and/or added in the protein (d) above and an amino acid residue corresponding to the 156th amino acid residue of SEQ ID NO: 4 is Val and/or an amino acid residue corresponding to the 233rd amino acid residue of SEQ ID NO: 4 is Phe and having an activity to add hexose at position 2 of glucose at position 13 in a compound represented by formula (I) above; or (f) a protein having an amino acid sequence having a sequence identity of 90% or more to the amino acid sequence of the protein (d) above wherein an amino acid residue corresponding to the 156th amino acid residue is Val and/or an amino acid residue corresponding to the 233rd amino acid residue is Phe in the amino acid sequence of SEQ ID NO: 4 and having an activity to add hexose at position 2 of glucose at position 13 in a compound represented by formula (I) above.

According to another embodiment, the protein according to the present invention is (g) a protein wherein the amino acid residue $X_2$ is Thr and/or the amino acid residue $X_3$ is Ser in the amino acid sequence of SEQ ID NO: 2; or (h) a protein consisting of an amino acid sequence wherein 1 to 48 amino acids are deleted, substituted, inserted, and/or added and an amino acid residue corresponding to the amino acid residue $X_2$ is Thr and/or an amino acid residue corresponding to the amino acid residue $X_3$ is Ser in the protein (g) above and having an activity to add hexose at position 2 of glucose at position 13 in a compound represented by formula (I) above; or (i) a protein having an amino acid sequence having a sequence identity of 90% or more to the amino acid sequence of the protein (g) above wherein an amino acid residue corresponding to the amino acid residue $X_2$ is Thr and/or an amino acid residue corresponding to the amino acid residue $X_3$ is Ser and having an activity to add hexose at position 2 of glucose at position 13 in a compound represented by formula (I) above.

The proteins described in above (b), (b'), (b"), (c), (c'), (c"), and (d) to (i) are typically naturally occurring mutants of polypeptides of SEQ ID NO: 2 or 4, but include those that can be obtained artificially by using site-directed mutagenesis described in, for example, "Sambrook & Russell, Molecular Cloning: A Laboratory Manual Vol. 3, Cold Spring Harbor Laboratory Press, 2001", "Ausubel, Current Protocols in Molecular Biology, John Wiley & Sons, 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", "Proc. Natl. Acad. Sci. USA, 82, 488 (1985)", or the like.

As used herein, the "protein consisting of an amino acid sequence wherein 1 to 48 amino acids other than the amino acid residue $X_7$ are deleted, substituted, inserted, and/or added in the amino acid sequence of SEQ ID NO: 2 and having an activity to add hexose at position 2 of glucose at position 13 in a compound represented by formula (I)" includes a protein consisting of an amino acid sequence wherein, for example, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue(s) is/are deleted, substituted, inserted, and/or added, besides the amino acid residue $X_7$, in the amino acid sequence set forth in SEQ ID NO: 2 and having an activity to add hexose at position 2 of glucose at position 13 in a compound represented by formula (I). In general, the number of amino acid residues in the aforementioned deletion, substitution, insertion, and/or addition is preferably smaller.

Moreover, such proteins include proteins having an amino acid sequence having a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence of SEQ ID NO: 2 wherein an amino acid corresponding to the amino acid residue $X_7$ is the same and having an activity to add hexose at position 2 of glucose at position 13 in a compound represented by formula (I). In general, the numerical value of the aforementioned sequence identity is preferably greater.

Similarly, the "protein consisting of an amino acid sequence wherein 1 to 48 amino acids other than the amino acid residues $X_1$ to $X_7$ are deleted, substituted, inserted, and/or added in the amino acid sequence of SEQ ID NO: 2 and having an activity to add hexose at position 2 of glucose at position 13 in a compound represented by formula (I)", as used herein, includes a protein consisting of an amino acid sequence wherein, for example, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue(s) is/are deleted, substituted, inserted, and/or added, besides the amino acid residues $X_1$ to $X_7$, in the amino acid sequence set forth in SEQ ID NO: 2 and having an activity to add hexose at position 2 of glucose at position 13 in a compound represented by formula (I). In general, the number of amino acid residues in the aforementioned deletion, substitution, insertion, and/or addition is preferably smaller.

Moreover, such proteins include proteins having an amino acid sequence having a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence of SEQ ID NO: 2 wherein amino acids corresponding to the amino acid residues $X_1$ to $X_7$ are the same and having an activity to add hexose at position 2 of glucose at position 13 in a compound represented by formula (I). In general, the numerical value of the aforementioned sequence identity is preferably greater.

As used herein, the "protein consisting of an amino acid sequence wherein 1 to 48 amino acids other than the amino acid residues $X_2$ and/or $X_3$ are deleted, substituted, inserted, and/or added in the amino acid sequence of SEQ ID NO: 2 and having an activity to add hexose at position 2 of glucose at position 13 in a compound represented by formula (I) above" includes a protein consisting of an amino acid sequence wherein, for example, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residue(s) is/are deleted, substituted, inserted, and/or added, besides the amino acid residues $X_2$ and/or $X_3$, in the amino acid sequence set forth in SEQ ID NO: 2 and having an activity to add hexose at position 2 of glucose at position 13 in a compound represented by formula (I). In general, the number of amino acid residues in the aforementioned deletion, substitution, insertion, and/or addition is preferably smaller.

Moreover, such proteins include proteins having an amino acid sequence having a sequence identity of 90% or more, 91% or more, 92% or more, 93% or more, 94% or more, 95% or more, 96% or more, 97% or more, 98% or more, 99% or more, 99.1% or more, 99.2° % or more, 99.3% or more, 99.4% or more, 99.5% or more, 99.6% or more, 99.7% or more, 99.8° % or more, or 99.9% or more to the amino acid sequence of SEQ ID NO: 2 wherein an amino acid corresponding to the amino acid residues $X_2$ and/or $X_3$ are the same and having an activity to add hexose at position 2 of glucose at position 13 in a compound represented by formula (I). In general, the numerical value of the aforementioned sequence identity is preferably greater.

As used herein, the "protein consisting of an amino acid sequence wherein 1 to 48 amino acids are deleted, substituted, inserted, and/or added in the protein (d) and an amino acid residue corresponding to the 156th amino acid residue is Val and/or an amino acid residue corresponding to the 233rd amino acid residue is Phe in the amino acid sequence of SEQ ID NO: 4 and having an activity to add hexose at position 2 of glucose at position 13 in a compound represented by formula (I) above" includes a protein consisting of an amino acid sequence wherein 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid residues is/are deleted, substituted, inserted, and/or added in the protein (d) and an amino acid residue corresponding to the 156th amino acid residue is Val and/or an amino acid residue corresponding to the 233rd amino acid residue is Phe in the amino acid sequence of SEQ ID NO: 4 and having an activity to add hexose at position 2 of glucose at position 13 in a compound represented by formula (I). In general, the number of amino acid residues in the aforementioned deletion, substitution, insertion, and/or addition is preferably smaller.

Moreover, such proteins include proteins having a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence of the protein (d), having an amino acid sequence wherein an amino acid residue corresponding to the 156th amino acid residue is Val and/or an amino acid residue corresponding to the 233rd amino acid residue is Phe in the amino acid sequence of SEQ ID NO: 4 and having an activity to add hexose at position 2 of glucose at position 13 in a compound represented by formula (I). In general, the numerical value of the aforementioned sequence identity is preferably greater.

As used herein, the "protein consisting of an amino acid sequence wherein 1 to 48 amino acids are deleted, substituted, inserted, and/or added and an amino acid residue corresponding to the amino acid residue $X_2$ is Thr and/or the amino acid residue corresponding to the amino acid residue $X_3$ is Ser in the protein (g) and having an activity to add hexose at position 2 of glucose at position 13 in a compound represented by formula (I) above" includes a protein consisting of an amino acid sequence wherein, for example, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or 1 amino acid(s) other than the amino acid residues $X_1$ to $X_7$ is/are deleted, substituted, inserted, and/or added and an amino acid residue corresponding to the amino acid residue $X_2$ is Thr and/or an amino acid residue corresponding to the amino acid residue $X_3$ is Ser in the protein (g) and having an activity to add hexose at position 2 of glucose at position 13 in a compound represented by formula (I). In general, the number of amino acid residues in the aforementioned deletion, substitution, insertion, and/or addition is preferably smaller.

Moreover, such proteins include proteins having a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more to the amino acid sequence of the protein (g), having an amino acid sequence wherein the amino acid residue corresponding to the amino acid residue $X_2$ is Thr and/or the amino acid residue corresponding to the amino acid residue $X_3$ is Ser and having an activity to add hexose at position 2 of glucose at position 13 in a compound represented by formula (I). In general, the numerical value of the aforementioned sequence identity is preferably greater.

Here, the "activity to add hexose at position 2 of glucose at position 13 in a compound represented by formula (I)" means an activity to add hexose at position 2 of the glucose group at position 13 in a compound represented by the following formula (I).

[Formula 2]

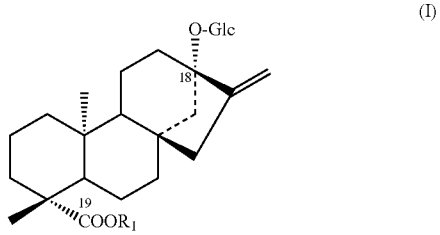

(I)

In formula (I), Glc represents a glucose residue. Moreover, in formula (I), $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a $(C_3$-$C_{10}$ cycloalkyl)$C_1$-$C_{10}$ alkyl group or a sugar residue.

As used herein, the "$C_1$-$C_{20}$ alkyl group" is preferably a $C_1$-$C_{10}$ alkyl group and more preferably a $C_1$-$C_6$ alkyl group, Examples of the alkyl group include, but are not limited to, methyl, ethyl, propyl, isopropyl, n-butyl, sec-butyl, tert-butyl, pentyl, hexyl, dodecanyl, and the like.

As used herein, the "$C_2$-$C_{20}$ alkenyl group" is preferably a $C_2$-$C_{10}$ alkenyl group and more preferably a $C_2$-$C_6$ alkenyl group. Examples of the alkenyl group include, but are not limited to, vinyl, allyl, propenyl, isopropenyl, 2-methyl-1-propenyl, 2-methylallyl, 2-butenyl, and the like.

As used herein, the "$C_2$-$C_{20}$ alkynyl group" is preferably a $C_2$-$C_{10}$ alkynyl group and more preferably a $C_2$-$C_6$ alkynyl group. Examples of the alkynyl group include, but are not limited to, ethynyl, 2-propynyl, 2-butynyl, and the like.

As used herein, the "$C_4$-$C_{20}$ alkyldienyl group" is preferably a $C_4$-$C_{10}$ alkyldienyl group and more preferably a $C_4$-$C_6$ alkyldienyl group. Examples of the alkyldienyl group include, but are not limited to, 1,3-butadienyl, and the like.

As used herein, the "$C_6$-$C_{18}$ aryl group" is preferably a $C_6$-$C_{10}$ aryl group. Examples of the aryl group include, but are not limited to, phenyl, 1-naphthyl, 2-naphthyl, indenyl, biphenylyl, anthryl, phenanthryl, and the like.

As used herein, the "$C_6$-$C_{20}$ alkylaryl group" is preferably a $C_6$-$C_{12}$ alkylaryl group. Examples of the alkylaryl group include, but are not limited to, o-tolyl, m-tolyl, p-tolyl, 2,3-xylyl, 2,4-xylyl, 2,5-xylyl, o-cumenyl, m-cumenyl, p-cumenyl, mesityl, and the like.

As used herein, the "$C_6$-$C_{20}$ arylalkyl group" is preferably a $C_6$-$C_{12}$ arylalkyl group. Examples of the arylalkyl group include, but are not limited to, benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, and the like.

As used herein, the "$C_4$-$C_{20}$ cycloalkyl group" is preferably a $C_4$-$C_{10}$ cycloalkyl group. Examples of the cycloalkyl group include, but are not limited to, cyclopropyl, cyclobutyl, cyclopentyl, cyclohexyl, and the like.

As used herein, the "$C_4$-$C_{20}$ cycloalkenyl group" is preferably a $C_4$-$C_{10}$ cycloalkenyl group. Examples of the cycloalkenyl group include, but are not limited to, cyclopropenyl, cyclobutenyl, 2-cyclopenten-1-yl, 2-cyclohexen-1-yl, 3-cyclohexen-1-yl, and the like.

Examples of the "$(C_3$-$C_{10}$ cycloalkyl)C-Cc alkyl group", as used herein, include methylcyclopropyl, ethylcyclopropyl, methylcyclobutyl, ethylcyclopentyl, methylcyclohexyl, and the like.

The "sugar residue", as used herein, is not particularly limited, but may be a sugar residue consisting of one or more pentose, hexose (including deoxyhexose), or a combination thereof.

Examples of the pentose include ribose, arabinose, and lyxose and examples of the hexose include allose, altrose, glucose, mannose, gulose, idose, galactose, talose, and rhamnose.

Preferably, the "sugar residue" is a sugar residue consisting of one or more hexose units and, more preferably, a sugar residue of a glucose monomer (-Glc) or a glucose dimer (-Glc-Glc). In the sugar residue of a glucose dimer, the glucose is preferably bound to each other by the β2,1-glycosidic linkage.

Preferably, the compound of formula (I) is steviolmonoside or rubusoside.

By the protein according to the present invention, hexose to be added to the compound represented by formula (I) at position 2 of glucose at position 13 in the compound is not particularly limited, but preferably a hexose selected from the group consisting of glucose, rhamnose, mannose, and galactose and, more preferably, glucose or rhamnose. Most preferably, the hexose is rhamnose. In the proteins according to (a), (b'), (b"), (c'), (c"), and (d) to (f) above, rhamnose can particularly advantageously be used as the hexose. Moreover, in the proteins according to (g) to (i) above, glucose can particularly advantageously be used as the hexose.

The activity to add hexose at position 2 of glucose at position 13 in a compound represented by formula (I) can be validated by incubating a buffer solution (for example, a sodium phosphate buffer or a potassium phosphate buffer), at a pH in a neutral region of pH 6.0 to 8.0, containing a test protein, a 1 to 1000 μM (preferably 100 to 700 μM and most preferably 500 μM) UDP sugar (for example, UDP-glucose), and a 1 to 500 μM (preferably 100 to 500 μM and most preferably 250 μM) substrate compound (a compound of formula (I)) at a temperature of 20 to 40° C. for from 10 minutes to 2 hours, then purifying the aforementioned substrate compound, and analyzing the purified monoterpene by a known technique such as the liquid chromatography-mass spectrometry (LC-MS) analysis.

If a compound in which hexose is added at position 2 of glucose at position 13 in the compound represented by formula (I) is detected, as a result of the LC-MS analysis, then the test protein is considered to be that having an activity to add hexose at position 2 in glucose at position 13 in a compound represented by formula (I). The aforementioned hexose addition reaction is usually completed in around 1 minute to 12 hours.

The one or more amino acid residues deleted, substituted, inserted, and/or added in the amino acid sequence of the protein according to the present invention means that there is deletion, substitution, insertion, and/or addition of one or more amino acid residues at the position(s) of any one or more amino acid sequences in the same sequence. Two or more of the deletion, substitution, insertion, and addition may occur simultaneously.

Examples of amino acid residues that may be substituted with each other are illustrated below. The amino acid residues included in a group may be substituted with each other. Group A: leucine, isoleucine, norleucine, valine, norvaline, alanine, 2-aminobutanoic acid, methionine, o-methylserine, t-butylglycine, t-butylalanine, cyclohexylalanine; Group B: aspartic acid, glutamic acid, isoaspartic acid, isoglutamic acid, 2-aminoadipic acid, 2-aminosuberic acid; Group C: asparagine, glutamine; Group D: lysine, arginine, ornithine, 2,4-diaminobutanoic acid, 2,3-diaminopropionic acid; Group E: proline, 3-hydroxyproline, 4-hydroxyproline; Group F: serine, threonine, homoserine; Group G: phenylalanine, tyrosine.

The protein according to the present invention can be obtained by expressing a polynucleotide (see the "Polynucleotide of the present invention" below) encoding this in an appropriate host cell, but it can be produced by a chemical synthetic method such as the fluorenylmethyl oxycarbonyl (Fmoc) method, the t-butyloxycarbonyl (tBoc) method, or the like. Moreover, the protein according to the present invention can be chemically synthesized with a peptide synthesizer such as that manufactured by Advanced Automation Peptide Protein Technologies, Inc., PerkinElmer, Inc., Protein Technologies Ltd., PerSeptive Biosystems, Inc., Applied Biosystems, or SHIMADZU CORPORATION.

2. Method of Producing Steviol Glycoside

Steviol glycosides can easily be produced in large amounts by making use of the activity to add hexose at position 2 of glucose at position 13 in a compound represented by formula (I) that the protein according to the present invention has.

Therefore, in another embodiment, the present invention provides a method of producing a steviol glycoside, comprising reacting the protein according to the present invention, a UDP-sugar, and a compound represented by the following formula (I) to add hexose at position 2 of glucose at position 13 in the compound represented by formula (I).

[Formula 3]

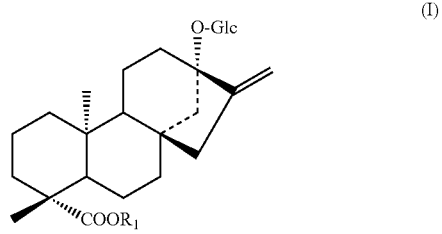

The definition of Glc and $R_1$ in formula (I) is as described above. Preferably, the compound of formula (I) is steviolmonoside or rubusoside.

As used herein, the "UDP-sugar" is uridine diphosphate (UDP)-bound sugar. Preferred examples of the sugar moiety in the UDP-sugar include sugar consisting of one or more hexose. Examples of the hexose are as described above. Preferably, the UDP-sugar is UDP-hexose and more preferably, the sugar is a hexose selected from the group consisting of glucose, rhamnose, mannose, and galactose. Most preferably, the aforementioned UDP-sugar is UDP-rhamnose. When a protein described in any of the aforementioned (a), (b'), (b"), (c'), (c"), and (d) to (f) is used as the protein according to the present invention, UDP-rhamnose can be used particularly advantageously as the UDP-sugar. Moreover, when a protein described in any of the aforementioned (g) to (i) is used as the protein according to the present invention, UDP-glucose can be used particularly advantageously as the UDP-sugar.

The first method of producing a steviol glycoside according to the present invention comprises reacting the protein according to the present invention, a UDP-sugar, and a compound represented by formula (I) to add hexose at position 2 of glucose at position 13 in the compound represented by formula (I). The first method of production according to the present invention may further comprise purifying the steviol glycoside produced in the aforementioned step. Moreover, the first method of production according to the present invention may comprise further adding sugar to the steviol glycoside produced in the aforementioned step.

Examples of the steviol glycoside that is produced by the first method of production include, but are not limited to, steviolbioside, stevioside, dulcoside A, Reb.E, or Reb.C, or a combination thereof.

The produced steviol glycoside can be purified by a known method such as extraction with an appropriate solvent (an aqueous solvent such as water or an organic solvent such as alcohol, ether, and acetone), the gradient of an organic solvent such as ethyl acetate:water, high performance liquid chromatography (HPLC), gas chromatography, time-of-flight mass spectrometry (TOF-MS), or ultra (high) performance liquid chromatography (UPLC).

3. Non-Human Transformant Highly Containing Steviol Glycoside

The steviol glycoside can be produced using the protein according to the present invention in cells of a microorganism (*Escherichia coli*, yeast, or the like), a plant, an insect, a mammal other than humans. This is because the protein according to the present invention is an enzyme from *Stevia rebaudiana* or a variant thereof and therefore expected to have high activity in the intracellular environment. In this case, a steviol glycoside can be produced by introducing a polynucleotide encoding the protein according to the present invention (see the "polynucleotide of the present invention" described below) into host cells from a microorganism, a plant, an insect, or a mammal other than humans to express the protein according to the present invention and reacting the protein according to the present invention, UDP-sugar present in the aforementioned cells, and a compound represented by formula (I).

[Formula 4]

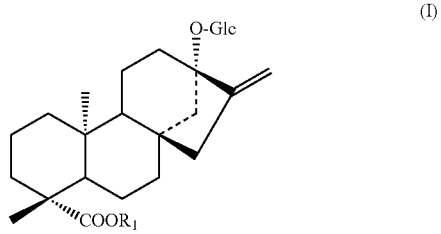

(I)

Accordingly, the present invention provides a non-human transformant (hereinafter, referred to as the "transformant of the present invention") in which a polynucleotide described in any one selected from the group consisting of the following (a) to (e) is introduced (hereinafter, referred to as the "polynucleotide of the present invention").

(a) a polynucleotide comprising the nucleotide sequence of SEQ ID NO: 1;

(b) a polynucleotide encoding a protein consisting of the amino acid sequences of SEQ ID NO: 2;

(c) a polynucleotide encoding a protein consisting of an amino acid sequence wherein 1 to 48 amino acids other than the amino acid residue $X_7$ are deleted, substituted, inserted, and/or added in the amino acid sequence of SEQ ID NO: 2 and having an activity to add hexose at position 2 of glucose at position 13 in a compound represented by formula (I) above;

(d) a polynucleotide encoding a protein having an amino acid sequence having a sequence identity of 90% or more to the amino acid sequence of SEQ ID NO: 2 wherein an amino acid corresponding to the amino acid residue $X_7$ is the same and having an activity to add hexose at position 2 of glucose at position 13 in a compound represented by formula (I) above:

Moreover, according to one aspect of the present invention, (c') a polynucleotide encoding a protein consisting of an amino acid sequence wherein 1 to 48 amino acids other than the amino acid residues $X_1$ to $X_7$ are deleted, substituted, inserted, and/or added in the amino acid sequence of SEQ ID NO: 2 and having an activity to add hexose at position 2 of glucose at position 13 in a compound represented by formula (I) above; or (d') a polynucleotide encoding a protein having an amino acid sequence having a sequence identity of 90% or more to the amino acid sequence of SEQ ID NO: 2 wherein amino acids corresponding to the amino acid residues $X_1$ to $X_7$ are the same and having an activity to add hexose at position 2 of glucose at position 13 in a compound represented by formula (I) above is provided.

According to another aspect of the present invention, (c") a polynucleotide encoding a protein consisting of an amino acid sequence wherein 1 to 48 amino acids other than the amino acid residues $X_2$ and/or $X_3$ are deleted, substituted, inserted, and/or added in the amino acid sequence of SEQ ID NO: 2 and having an activity to add hexose at position 2 of glucose at position 13 in a compound represented by formula (I) above; or (d") a polynucleotide encoding a protein having an amino acid sequence having a sequence identity of 90% or more to the amino acid sequence of SEQ ID NO: 2 wherein amino acids corresponding to the amino acid residues $X_2$ and/or $X_3$ are the same and having an activity to add hexose at position 2 of glucose at position 13 in a compound represented by formula (I) above is provided.

According to another aspect of the present invention, (e) a polynucleotide encoding a protein wherein the 156th amino acid residue is Val and/or the 233rd amino acid residue is Phe in the amino acid sequence of SEQ ID NO: 4; or (f) a polynucleotide encoding a protein consisting of an amino acid sequence wherein 1 to 48 amino acids are deleted, substituted, inserted, and/or added in the protein according to (e) above and an amino acid residue corresponding to the 156th amino acid residue of SEQ ID NO: 4 is Val and/or an amino acid residue corresponding to the amino acid residue of the 233rd of SEQ ID NO: 4 is Phe and having an activity to add hexose at position 2 of glucose at position 13 in a compound represented by formula (I) above; or (g) a polynucleotide encoding a protein having an amino acid sequence having a sequence identity of 90% or more to the amino acid sequence of the protein according to (e) above wherein an amino acid residue corresponding to the 156th amino acid residue of SEQ ID NO: 4 is Val and/or an amino acid residue corresponding to the 233rd amino acid residue of SEQ ID NO: 4 is Phe and having an activity to add hexose at position 2 of glucose at position 13 in a compound represented by formula (I) above is provided.

According to another aspect of the present invention, (h) a polynucleotide encoding a protein wherein the amino acid residue $X_2$ is Thr and/or the amino acid residue $X_3$ is Ser in the amino acid sequence of SEQ ID NO: 2; or (i) a polynucleotide encoding a protein consisting of an amino acid sequence wherein 1 to 48 amino acids are deleted, substituted, inserted, and/or added in the protein according to (h) above and an amino acid residue corresponding to the amino acid residue $X_2$ is Thr and/or an amino acid residue corresponding to the amino acid residue $X_3$ is Ser and having an activity to add hexose at position 2 of glucose at position 13 in a compound represented by formula (I) above; or (j) a polynucleotide encoding a protein having an amino acid sequence having a sequence identity of 90% or more to the amino acid sequence of the protein according to (h) above wherein an amino acid residue corresponding to the amino acid residue $X_2$ is Thr and/or an amino acid residue corresponding to the amino acid residue $X_3$ is Ser and having an activity to add hexose at position 2 of glucose at position 13 in a compound represented by formula (I) above is provided.

The definition and specific examples of formula (I) are as described above and the definition and specific examples of the hexose to be added at position 2 of glucose at position 13 in the compound represented by formula (I) are also as described above.

As used herein, the "polynucleotide" means DNA or RNA.

As used herein, the "polynucleotide that hybridizes under highly stringent conditions" refers to a polynucleotide obtained by performing colony hybridization, plaque hybridization, Southern hybridization, or the like, using for example, all or a part of a polynucleotide consisting of a nucleotide sequence complementary to the nucleotide sequence set forth in SEQ ID NO: 1 or a polynucleotide consisting of a nucleotide sequence encoding the amino acid sequence set forth in SEQ ID NO: 2 as a probe. Examples of available methods of hybridization include methods described in "Sambrook & Russell, Molecular Cloning A Laboratory Manual Vol. 3, 2001 Cold Spring Harbor, Laboratory Press", "Ausubel, Current Protocols in Molecular Biology, John Wiley & Sons 1987-1997", and the like.

Examples of the "highly stringent conditions" as used herein are, but not limited to, conditions of (1) 5×SSC, 5× den Hald solution, 0.5% SDS, 50% formamide, 50° C.; (2) 0.2×SSC, 0.1% SDS, 60° C., (3) 0.2×SSC, 0.1% SDS, 62° C.; (4) 0.2×SSC, 0.1% SDS, 65° C.; or (5) 0.1×SSC, 0.1% SDS, 65° C. Under these conditions, it can be expected that DNA having a high sequence identity is obtained more efficiently at higher temperatures. Meanwhile, it is considered that there are plural factors that have effects on the stringency of hybridization, such as temperature, the probe concentration, the probe length, the ionic strength, time, and the salt concentration and a person skilled in the art can attain similar stringency by selecting these factors as appropriate.

When using a commercially available kit for hybridization, for example, Alkphos Direct Labelling and Detection System (GE Healthcare) may be used. In this case, hybridized DNA can be detected after incubating a membrane with a labelled probe overnight in accordance with the protocol attached to the kit and then washing the membrane with a primary washing buffer containing 0.1% (w/v) SDS under conditions at 55 to 60° C. Alternatively, hybridization can be detected by using the DIG nucleic acid detection kit (Roche Diagnostics), when the probe is labeled with digoxigenin (DIG) by using a commercially available reagent (for example, PCR labeling mixture (Roche Diagnostics)), in the production of a probe based on a nucleotide sequence complementary to the nucleotide sequence set forth in SEQ ID NO: 1 or a sequence complementary to all or a part of a nucleotide sequence encoding the amino acid sequence set forth in SEQ ID NO: 2.

Examples of hybridizable polynucleotide other than those described above include DNA having a sequence identity of 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1 or more, 99.2% or more, 99.3% or more, 99.4% or more, 99.5% or more, 99.6% or more, 99.7% or more, 99.8% or more, or 99.9% or more to the DNA of SEQ ID NO: 1 or DNA encoding the amino acid sequence set forth in SEQ ID NO: 2 as calculated by homology search software such as FASTA or BLAST using default parameters.

The sequence identity of an amino acid sequence or a nucleotide sequence can be determined using FASTA (Science 227 (4693): 1435-1441 (1985)) or the algorithm by Karlin and Altschul BLAST (Basic Local Alignment Search Tool) (Proc. Natl. Acad. Sci. USA 872264-2268, 1990; Proc Natl Acad Sci USA 90: 5873, 1993). The programs called blastn, blastx, blastp, tblastn, and tblastx based on the algorithm of BLAST have been developed (Altschul S F, et al: J Mol Biol 215:403, 1990). When analyzing a nucleotide sequence using blastn, parameters are set at, for example, score=100, wordlength=12. Moreover, when analyzing an amino acid sequence using blastp, parameters are, for example, score=50, wordlength=3. When using BLAST and Gapped BLAST programs, the default parameters of each program are used.

The polynucleotide of the present invention described above can be obtained by a known genetic engineering technique or a known synthetic method.

The polynucleotide of the present invention is preferably introduced into a host in a state inserted into an appropriate expression vector.

An appropriate expression vector is usually configured to comprise:

(i) a promoter that allows the transcription in host cells, (ii) the polynucleotide of the present invention connected to the promoter; and (iii) an expression cassette comprising signals that function in host cells as a component for the termination of transcription of RNA molecules and the polyadenylation.

Examples of the method of producing the expression vector include, but are not particularly limited to, methods using a plasmid, a bacteriophage, a cosmid or the like.

The specific kind of vector is not particularly limited, but a vector expressible in host cells can be selected as appropriate. More specifically, a vector obtained by selecting a promoter sequence that ensures the expression of the polynucleotide of the present invention, as appropriate, depending on the kind of host cells and incorporating the promoter and the polynucleotide of the present invention into a certain plasmid may be used as an expression vector.

The expression vector according to the present invention contains an expression regulatory region (for example, a promoter, a terminator, and/or a replication origin) depending on the kind of the host in which the expression vector is to be introduced. A conventional promoter (for example, trc promoter, tac promoter, lac promoter) is used as the promoter of the expression vector for bacteria, examples of a promoter for yeast include the GAL1 promoter, the GAL10 promoter, the glyceraldehyde-3-phosphate dehydrogenase promoter, the PH05 promoter, and the like, and examples of a promoter for filamentous fungi include those for amylase and trpC, and the like. Moreover, examples of a promoter for expressing a gene of interest in plant cells include the 35S RNA promoter from cauliflower mosaic virus, the rd29A gene promoter, the rbcS promoter, the mac-1 promoter, which is a promoter obtained by adding an enhancer sequence of the aforementioned 35S RNA promoter from cauliflower mosaic virus on 5' of the mannopine synthase promoter sequence derived from *Agrobacterium*, and the like. Examples of a promoter for an animal cell host include a viral promoter (for example, the SV40 early promoter, the SV40 late promoter, or the like).

The expression vector preferably comprises at least one selection marker. Such markers that are available include auxotrophic markers (ura5, niaD, TRP1, URA3, HIS3, LEU2), drug resistance markers (hygromycin, Zeocin), Geneticin resistance genes (G418r), copper resistance genes (CUP1) (Marin et al., Proc. Natl. Acad. Sci. USA, vol. 81, p. 337, 1984), and cerulenin resistance genes (fas2m, PDR4) (Inokoshi, Junji, et al., Biochemistry, vol. 64, p. 660, 1992; and Hussain et al., Gene, vol. 101, p. 149, 1991, respectively).

The method of producing the transformant according to the present invention (method of production) is not particularly limited, but examples thereof include a method involving introducing an expression vector containing the polynucleotide of the present invention into a host to transform the host.

The transformant according to the present invention is expected to produce a steviol glycoside at high efficiency. The host cells to be used in transformation are not particularly limited, but various known cells may suitably be used. For example, examples of the host cells include bacteria such as *Escherichia coli*, yeast (the budding yeast *Saccharomyces cerevisiae*, the fission yeast *Schizosaccharomyces pombe*), plant cells, animal cells other than human cells, and the like. The host cells may be xenogeneic cells (cells from an organism other than *Stevia rebaudiana*) or allogeneic cells (cells from *Stevia rebaudiana*). When using allogeneic cells as a transformant, the transformant according to the present invention has the enzymatic reaction promoted in comparison with wild type *Stevia rebaudiana* cells since the protein according to the present invention introduced exogenously is expressed in addition to the protein expressed endogenously.

The host cells are preferably host cells that can produce a compound represented by formula (I). The host cells are not limited to those that can produce a compound represented by formula (I) in natural states, but may be, for example, those recombinantly engineered with a known gene so as to be capable of producing a compound represented by formula (I).

Examples of the known gene encoding an enzyme that contributes to the synthesis of the compound represented by formula (I) include, but are not limited to, EK13H, UGT74G1, UGT76G1 (Non-Patent Literature 2), and the like.

When the host cells are cells that cannot produce a compound represented by formula (I), a steviol glycoside can be produced by adding a compound of formula (I) or a plant extract containing the compound as a substrate to a culture system of the transformant obtained by introducing the gene of the present invention into a host cell, without introducing a gene encoding an enzyme that contributes to the synthesis of a compound represented by formula (I).

Furthermore, a more glycosylated steviol glycoside (for example, steviolbioside, Rebaudioside A, stevioside, and Rebaudioside B) can be produced by expressing the polynucleotide of the present invention in the host cells using the host cells in which a gene encoding a glycosyltransferase involved in a series of glycoside synthesis from steviol to Rebaudioside A is introduced. Examples of the glycosyltransferase involved in a series of glycoside synthesis from steviol to Rebaudioside A and a gene thereof include UGT85C2 (CDS sequence: SEQ ID NO: 7, amino acid sequence: SEQ ID NO: 8), UGT74G1 (CDS sequence: SEQ ID NO: 9, amino acid sequence: SEQ ID NO: 10), UGT76G1 (CDS sequence: SEQ ID NO: 11, amino acid sequence: SEQ ID NO: 12), and the like.

The aforementioned appropriate culture media and conditions for host cells are well-known in the art. Moreover, the organism to be transformed is not particularly limited, but examples thereof include the microorganisms, plants, or animals other than humans illustrated for the aforementioned host cells.

For other general techniques in molecular biology, see Sambrook & Russell, "Molecular Cloning: A Laboratory Manual" Vol. 3, Cold Spring Harbor Laboratory Press 2001; "Methods in Yeast Genetics, A laboratory manual" (Cold Spring Harbor Laboratory Press, Cold Spring Harbor, N.Y.).

By culturing the transformant obtained in this way, it is possible to have the transformant produce a steviol glycoside. As described above, the production of the steviol glycoside can be promoted by adding the compound of formula (I) or a plant extract containing the compound as a substrate to a culture system of the transformant. The steviol glycoside of interest can be obtained by extracting and purifying the accumulated steviol glycoside.

Accordingly, the present invention provides a second method of producing a steviol glycoside characterized by using the transformant according to the present invention. Appropriate culture media and conditions are well-known in the art. The method of extracting and purifying a steviol glycoside is as described above.

The steviol glycoside is not particularly limited, but may preferably be one selected from the group consisting of steviolbioside, stevioside, dulcoside A, Reb.E, or Reb.C or a combination thereof.

In one aspect of the present invention, the host cells for transformation to be used may be any yeast. Specifically, the host cells include, but are not limited to, yeast such as those in the genus *Saccharomyces*.

Examples of available methods of transforming yeast include known methods that are generally used. The transformation can be conducted by methods such as, but not limited to, those described in Meth. Enzym., 194, p 182 (1990) (electroporation); Proc. Natl. Acad. Sci. USA, 75 p 1929 (1978) (the spheroplast method); J. Bacteriology, 153, p. 163 (1983) (the lithium acetate method); Proc. Natl. Acad. Sci. USA, 75 p. 1929 (1978); Methods in yeast genetics, 2000 Edition: A Cold Spring Harbor Laboratory Course Manual; and the like. The transformant strain is obtained by selecting a strain that grows in a medium with a selective pressure for the selection marker used (for example, a medium containing an antibiotic or a medium lacking a nutrient).

In one aspect of the present invention, the transformant may be a plant transformant. The plant transformant according to the present embodiment is obtained by introducing a recombinant vector containing the polynucleotide according to the present invention into a plant such that the polypeptide encoded by the polynucleotide can be expressed. Alternatively, a new plant having the gene can be obtained by using the transformant according to the present invention as a crossing parent since the gene of the present invention is inherited by offspring.

When using a recombination expression vector, the recombination expression vector used in transformation of plant bodies is not particularly limited as long as it is a vector that can express the polynucleotide according to the present invention in the plant. Examples of such a vector include a vector having a promoter that allows the constitutive expression of a polynucleotide in plant cells or a vector having a promoter that is inductively activated by an external stimulus.

Examples of the promoter that allows the constitutive expression of a polynucleotide in plant cells include the 35S RNA promoter from cauliflower mosaic virus, the rd29A gene promoter, the rbcS promoter, the mac-1 promoter, and the like.

Examples of the promoter inducibly activated by an external stimulus include the mouse mammary tumor virus (MMTV) promoter, the tetracycline responsiveness promoter, the metallothionein promoter, the heat shock protein promoter, and the like.

The plant to be transformed in the present invention means the whole plant body, a plant organ (for example, a leaf, a petal, a stem, a root, a seed, or the like), plant tissue (for example, epidermis, phloem, parenchyma, xylem, vascular bundle, palisade tissue, spongy tissue, or the like) or cultured plant cells, various forms of plant cells (for example, suspension cultured cells), protoplasts, a leaf section, callus, or the like. The plant used in transformation is not particularly limited, but may be any of plants belonging to Monocotyledoneae or Dicotyledoneae.

The introduction of a gene into a plant is conducted by a method of transformation known to those skilled in the art (for example, the *Agrobacterium* method, the gene gun method, the PEG method, electroporation, particle bombardment, or the like).

The cells or plant tissue in which a gene has been introduced is first selected for drug resistance such as the hygromycin resistance and then reproduced into a plant by a conventional method. The reproduction of a plant from transformed cells may be conducted by a method known to those skilled in the art depending on the kind of the plant cells.

Whether the polynucleotide of the present invention has been introduced into a plant or not can be confirmed by PCR, Southern hybridization, Northern hybridization, or the like.

Once the transformed plant in which the polynucleotide of the present invention is incorporated in the genome is obtained, offspring can be obtained by sexual reproduction or asexual reproduction of the plant. Moreover, it is possible to obtain, for example, a seed, a fruit, cutting, a tuber, a tuberous root, a strain, a callus, a protoplast, or the like from the plant or offspring thereof or a clone thereof and produce the plant therefrom at a large quantity. Accordingly, the present invention also includes a plant in which the polynucleotide according to the present invention has been expressibly introduced, or offspring of the plant having the same traits as the plant, or tissue derived therefrom.

Moreover, methods for transforming various plants have been already reported. The transformant plant according to the present invention is not limited, but particularly preferable examples desirable to be used include plants known to bio-synthesize various glycosides using steviol as aglycones and examples of such a plant include *Stevia rebaudiana* and *Rubus suavissimus*.

The plant transformed with the polynucleotide of the present invention (hereinafter, the "plant of the present invention" or "plant body of the present invention") can produce a steviol glycoside more than the wild type when it has an appropriate substrate or when an appropriate substrate is added from the outside.

From the plant of the present invention, a complete plant body can easily be obtained by growing a seed, a cutting, a bulb, or the like of the plant of the present invention.

Accordingly, the plant of the present invention includes a whole plant body, a plant organ (for example, a leaf, a petal, a stem, a root, a seed, a bulb), plant tissue (for example, epidermis, phloem, parenchyma, xylem, vascular bundle, palisade tissue, spongy tissue) or cultured plant cells, or various forms of plant cells (for example, suspension cultured cells), a protoplast, a section of leaf, a callus, and the like.

4. Extract of Transformant and Use Thereof

In another embodiment, the present invention also provides an extract of the aforementioned transformant. Since the transformant according to the present invention contains steviol glycosides at a higher content than the wild type when it has an appropriate substrate or when an appropriate substrate is added from the outside, extracts thereof are considered to contain steviol glycosides at high concentrations.

The extract of the transformant according to the present invention has a higher ratio of hexose, in particular rhamnose and/or glucose, to the aglycones in the whole steviol glycosides than extracts of the wild type *Stevia rebaudiana*, even when the transformant is cells from *Stevia rebaudiana*. Since the introduced protein according to the present invention is expressed and adds hexose to steviol glycosides in the transformant according to the present invention, the number of hexose residues added to a unit quantity (for example, a unit number of molecules) of steviol aglycones, when collectively taking the whole steviol glycosides, is of course increased in comparison with cells expressing no such protein (for example, wild type *Stevia rebaudiana* cells). The change in ratio of hexose to the aglycones in the whole steviol glycosides has effects on the properties of extract, for example, the sensory properties, for example, sweetness and the like.

The extract of the transformant according to the present invention can be obtained by homogenizing the transformant using glass beads, a homogenizer, or a sonicator, centrifuging the resultant homogenate, and collecting the supernatant. Furthermore, a further extraction step by the methods of extracting steviol glycosides described above may be conducted.

The extract of the transformant according to the present invention can be used, according to a conventional method, for a purpose such as the production of a food, a pharmaceutical product, an industrial raw material, or the like.

In another embodiment, the present invention also provides a food, a medicament, an industrial raw material (a raw material for a food or the like) comprising an extract of the transformant according to the present invention. The food, medicament, or industrial raw material containing an extract of the transformant according to the present invention is prepared according to a conventional method. As seen above, the food, medicament, or industrial raw material containing an extract of the transformant according to the present invention contains a steviol glycoside produced using the transformant according to the present invention. The aforementioned food, medicament, or industrial raw material may comprise an unnatural ingredient. Examples of the unnatural ingredient include a compound that does not occur naturally, for example, a synthetic additive such as a synthetic flavorant and a synthetic preservative, a fermentation product, and the like.

Examples of the food of the present invention include a dietary supplement, a health food, a functional food, a food for infants, a food for the elderly, and the like. As used herein, the food is a solid, a fluid, and a liquid, and a mixture thereof and is a generic name for edibles.

The dietary supplement refers to a food enriched with a particular nutrition ingredient. The health food refers to a food that is healthy or considered to be good for health and includes a dietary supplement, a natural food, a diet food, and the like. The functional food refers to a food for supplying a nutrition ingredient which serves a function in regulating physical conditions and is synonymous with a food for a specified health use. The food for infants refers to a food for feeding a child to up to about 6 years old. The food for the elderly refers to a food treated so as to be more easily digested and absorbed than a food with no treatment.

The food of the present invention uses a calorie-less steviol glycoside as a sweetener. Therefore, the food of the present invention is low-calorie and has a merit of contributing to health promotion or health maintenance.

Examples of the forms of these foods may be agricultural foods such as bread, noodles, pasta, rice, confectionery (a cake, ice cream, popsicles, doughnuts, baked confectionery, candy, chewing gum, gummy candy, tablets, and Japanese sweets such as a dumpling and a steamed bun), tofu and processed products thereof; fermented foods such as refined sake, alcoholic drinks with medical properties, sweet sake, vinegar, soy sauce, and miso; livestock foods such as yogurt, ham, bacon, and sausage; sea foods such as kamaboko, fried fish paste, and cakes of ground fish; fruit juice beverages, refreshing beverages, sports beverages, alcoholic beverages; tea, and the like or flavoring agents. Examples of the forms of further foods include low calorie beverage, non-sugar beverage, canned fruits, milk beverage, beverage powder, yogurt, Jelly, dressing, noodle soup, pickle, a food boiled down in soy, soy sauce, miso, fish guts pickled in salt, Vermont vinegar, sweet pickled scallions, sweet and sour ginger, and a pickled lotus root, as well as a pickle, sauces for tempura and kabayaki, sauce for grilled meats, sources, gum, candy, toothpaste, a deep-fried patty of fish paste, rolled omelet, chow mein source, sauce for cold Chinese noodles, cut mackerel sprinkled with salt and then pickled in vinegar, ice cream, sherbet, soft ice cream, fish paste, snack food, rice confectionery, a corn cup, seasoned laver, bits of tempura batter that have fallen into the hot oil and been deep-fried, flaked seasoning for sprinkling over rice, and the like.

The food of the present invention encompasses any processed food. In one aspect, the processed food is made from natural raw materials, but different from natural products in the properties (for example, physical properties such as elasticity, viscosity, hardness, and the like; and sensory properties such as taste, smell, and texture). Many existing processed foods belong to this class. In another aspect, the processed food comprises an unnatural ingredient.

Moreover, the food of the present invention encompasses any beverage. In one aspect, the beverage is made from natural raw materials, but different from natural products in the properties (for example, physical properties such as viscosity and cohesive power; and sensory properties such as taste, smell, and texture). Examples of such a beverage include fermentation beverages (for example, lactic fermenting beverages, alcoholic beverages such as refined sake, wine, beer, alcoholic drinks with medical properties, half fermented tea such as oolong tea, total fermented tea such as black tea, and post-heating fermented tea such as Pu-erh tea), smoothie, milk shake, and the like. In another aspect, the beverage comprises an unnatural ingredient.

The dosage form of the pharmaceutical product (composition) according to the present invention is not particularly limited, and may be any dosage form, such as a solution, paste, gel, solid, or powder. Moreover, the pharmaceutical product (pharmaceutical composition) according to the present invention can be used in a skin external preparations such as an oil, a lotion, a cream, an emulsion, a gel, a shampoo, a hair rinse, a hair conditioner, enamel, a foundation, a lipstick, face powder, a pack, ointment, powder, toothpaste, aerosol, or a cleansing foam, as well as a bath preparation, hair tonic, skin essence, a sunscreen, or the like.

The pharmaceutical composition according to the present invention may further comprise another pharmaceutically active ingredients (for example, an anti-inflammatory ingredient) or an auxiliary ingredient (for example, a lubricant ingredient, a carrier ingredient) as needed. The pharmaceutically active ingredient or auxiliary ingredient may be a natural ingredient or an unnatural ingredient.

5. Method of Screening for Plant with High Content of Steviol Glycoside Having Rhamnose Group The present invention provides a method of screening for a plant with a high content of steviol glycoside having rhamnose groups. Specifically, the aforementioned method comprises the following steps (1) to (3).

(1) extracting mRNA from a test plant;
(2) hybridizing the aforementioned mRNA or a cDNA prepared from the aforementioned mRNA with a polynucleotide that hybridizes with a polynucleotide consisting of a nucleotide sequence complementary to the polynucleotide of the present invention under highly stringent conditions;
(3) detecting the aforementioned hybridization.

The aforementioned step (1) can be carried out by extracting mRNA from a test plant. The part in the test plant from which mRNA is extracted is not particularly limited, but preferably a petal. When mRNA is extracted, cDNA may be prepared from mRNA by reverse transcription.

The step (2) can be carried out by hybridizing a polynucleotide or oligonucleotide consisting of nucleotide sequence complementary to the polynucleotide of the present invention as a probe or a primer with the mRNA extracted as described above under highly stringent conditions. The highly stringent conditions are as described above. The polynucleotide or oligonucleotide is preferably 5 to 500 bp, more preferably 10 to 200 bp, and further preferably 10 to 100 bp in length. The polynucleotide or oligonucleotide can easily be synthesized using various automatic synthesizers (for example, AKTA oligopilot plus 10/100 (GE Healthcare)) or the synthesis can be outsourced to a third party (for example, Promega Corporation or Takara Bio Inc.).

When using a polynucleotide consisting of a nucleotide sequence complementary to the polynucleotide of the present invention as a probe in step (2), the step (3) can be carried out by a method of hybridization detection such as usual Southern blotting, Northern blotting (Sambrook, Fritsch and Maniatis, "Molecular Cloning: A Laboratory Manual" 2nd Edition (1989), Cold Spring Harbor Laboratory Press), Microarray (see Affymetrix Inc., U.S. Pat. Nos. 6,045,996, 5,925,525, and 5,858,659), TaqMan PCR (Sambrook, Fritsch and Maniatis, "Molecular Cloning: A Laboratory Manual" 2nd Edition (1989), Cold Spring Harbor Laboratory Press), or Fluorescent In Situ Hybridization (FISH) (Sieben V. J. et al., (2007-06). IET Nanobiotechnology 1 (3): 27-35). Meanwhile, when using a polynucleotide consisting of a nucleotide sequence complementary to the polynucleotide of the present invention as a primer in the step (2), hybridization can be detected in the step (3) by performing the PCR amplification reaction and analyzing the obtained amplified product by electrophoresis or sequencing, or the like (Sambrook, Fritsch and Maniatis, "Molecular Cloning: A Laboratory Manual" 2nd Edition (1989), Cold Spring Harbor Laboratory Press).

The plant for which more hybridization has been detected is expected to have a high content of steviol glycosides having rhamnose groups in comparison with other plant bodies since it is considered to have higher expression of a protein having an activity to add hexose, particularly rhamnose, at position 2 of glucose at position 13 in a compound represented by the following formula (I).

[Formula 5]

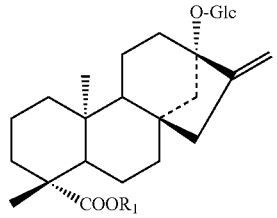

(I)

6. Method of Producing UGT with Changed Sugar Donor Selectivity

In another side, the present invention provides a method of producing UGT with changed sugar donor selectivity. In one aspect, the aforementioned method comprises the following steps (1) to (2).

(1) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT; and (2) substituting the amino acid residue corresponding to the amino acid residue $X_2$ in SEQ ID NO: 2 or the 156th amino acid residue in SEQ ID NO: 4, if the amino acid residue is Thr or Ser, preferably Thr, with Val, Leu, Ile, Ala, or Met, preferably Val, and, if the amino acid is Val, Leu, Ile, Ala, or Met, preferably Val, with Thr or Ser, preferably Thr, and/or substituting the amino acid residue corresponding to the amino acid residue $X_3$ in SEQ ID NO: 2 or the 233rd amino acid residue in SEQ ID NO: 4, if the amino acid residue is Ser or Thr, preferably Ser, with Phe or Tyr, preferably Phe, and, if the amino acid is Phe or Tyr, preferably Phe, with Ser or Thr, preferably Ser.

In a particular aspect, the present invention provides a method of producing UGT whose sugar donor selectivity is shifted from UDP-glucose to UDP-rhamnose. In one aspect, the aforementioned method comprises the following steps (1) to (2).

(1) identifying UGT having an amino acid sequence in which the amino acid residue corresponding to the amino acid residue $X_2$ in SEQ ID NO: 2 or the 156th amino acid residue in SEQ ID NO: 4 is Thr or Ser, preferably Thr and/or the amino acid residue corresponding to the amino acid residue $X_3$ in SEQ ID NO: 2 or the 233rd amino acid residue in SEQ ID NO: 4 is Ser or Thr, preferably Ser;

(2) substituting the amino acid residue corresponding to the amino acid residue $X_2$ in SEQ ID NO: 2 or the 156th amino acid residue in SEQ ID NO: 4 in the amino acid sequence of UGT identified in (1), if the amino acid residue is Thr or Ser, preferably Thr, with Val, Leu, Ile, Ala, or Met, preferably Val, and/or substituting the amino acid residue corresponding to the amino acid residue $X_3$ in SEQ ID NO: 2 or the 233rd amino acid residue in SEQ ID NO: 4, if the amino acid is Ser or Thr, preferably Ser, with Phe or Tyr, preferably Phe.

In another aspect, the aforementioned method comprises the following steps (1) to (3).

(1) identifying UGT having a sugar donor selectivity for UDP-glucose, (2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT identified in (1);

(3) substituting the amino acid residue corresponding to the amino acid residue $X_2$ in SEQ ID NO: 2 or the 156th amino acid residue in SEQ ID NO: 4, if the amino acid residue is Thr or Ser, preferably Thr, with Val, Leu, Ile, Ala, or Met, preferably Val, and/or substituting the amino acid residue corresponding to the amino acid residue $X_3$ in SEQ ID NO: 2 or the 233rd amino acid residue in SEQ ID NO: 4, if the amino acid is Ser or Thr, preferably Ser, with Phe or Tyr, preferably Phe.

In another particular aspect, the present invention provides a method of producing UGT whose sugar donor selectivity is shifted from UDP-rhamnose to UDP-glucose. In one aspect, the aforementioned method comprises the following steps (1) to (2).

(1) identifying UGT having an amino acid sequence in which the amino acid residue corresponding to the amino acid residue $X_2$ in SEQ ID NO: 2 or the 156th amino acid residue in SEQ ID NO: 4 is Val, Leu, Ile, Ala, or Met, preferably Val, and/or the amino acid residue corresponding to the amino acid residue $X_3$ in SEQ ID NO: 2 or the 233rd amino acid residue in SEQ ID NO: 4 is Phe or Tyr, preferably Phe;

(2) substituting the amino acid residue corresponding to the amino acid residue $X_2$ in SEQ ID NO: 2 or the 156th amino acid residue in SEQ ID NO: 4, if the amino acid residue is Val, Leu, Ile, Ala, or Met, preferably Val, with Thr or Ser, preferably Thr, and/or substituting the amino acid residue corresponding to the amino acid residue $X_3$ in SEQ ID NO: 2 or the 233rd amino acid residue in SEQ ID NO: 4, if the amino acid residue is Phe or Tyr, preferably Phe, with Ser or Thr, preferably Ser in the amino acid sequence of UGT identified in (1).

In another aspect, the aforementioned method comprises the following steps (1) to (3).

(1) identifying UGT having a sugar donor selectivity for UDP-rhamnose;

(2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT identified in (1);

(3) substituting the amino acid residue corresponding to the amino acid residue $X_2$ in SEQ ID NO: 2 or the 156th amino acid residue in SEQ ID NO: 4, if the amino acid residue is Val, Leu, Ile, Ala, or Met, preferably Val, with Thr or Ser, preferably Thr, and/or substituting the amino acid residue corresponding to the amino acid residue $X_3$ in SEQ ID NO: 2 or the 233rd amino acid residue in SEQ ID NO: 4, if the amino acid residue is Phe or Tyr, preferably Phe, with Ser or Thr, preferably Ser.

In each method of producing UGT with changed sugar donor selectivity described above, the identification of the amino acid residue corresponding to the predetermined amino acid residue in the amino acid sequence of the UGT of interest can be made by any known method, for example, the alignment of the amino acid sequence of the UGT of interest and a standard amino acid sequence (SEQ ID NO: 2 or 4), the homology modeling using the protein consisting of the amino acid sequence of SEQ ID NO: 2 or 4 as a template, or the like.

The substitution of amino acid in the UGT of interest can be made, for example, by the aforementioned site-directed mutagenesis or the like. Moreover, the polynucleotide encoding the aforementioned amino acid related to the sugar donor selectivity may be modified by genome editing or the like to express a desired amino acid in the genome of the plant having the UGT of interest.

The identification of UGT having a sugar donor selectivity for UDP-glucose or UDP-rhamnose can be made based on literature or experimentally. To identify the aforementioned UGT experimentally, for example, the comparison can be made between the result of the reaction of UGT of interest, UDP-glucose or UDP-rhamnose, and a sugar receptor substrate (for example, the compound represented by formula (I)) under conditions suitable for the glycosidation reaction and the result of a reaction under the same conditions except that a compound different from one used in the aforementioned reaction is used as a sugar donor. When the reaction using UDP-glucose or UDP-rhamnose is more efficient than the reaction using another sugar donor, the UGT can be determined to have a sugar donor selectivity for UDP-glucose or UDP-rhamnose.

By any of the aforementioned methods, the UGT having a sugar donor selectivity for UDP-glucose or UDP-rhamnose can easily be designed or produced. Moreover, the sugar donor selectivity of UGT expressed in the plant can be changed to control the kind of glycoside sugar accumulated in the plant by the substitution of an amino acid residue of UGT at the genomic level.

7. Method of Estimating Sugar Donor Selectivity of UGT

In another side, the present invention provides a method of estimating the sugar donor selectivity of UGT. In one aspect, the aforementioned method comprises the following steps (1) to (2).

(1) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT; and (2) estimating that the aforementioned UGT has a sugar donor selectivity for UDP-glucose if the amino acid residue corresponding to the amino acid residue $X_2$ in SEQ ID NO: 2 or the 156th amino acid residue in SEQ ID NO: 4 is Thr or Ser, preferably Thr, and/or the amino acid residue corresponding to the amino acid residue $X_3$ in SEQ ID NO: 2 or the 233rd amino acid residue in SEQ ID NO: 4 is Ser or Thr, preferably Ser; and estimating that the aforementioned UGT has a sugar donor selectivity for UDP-rhamnose if the amino acid residue corresponding to the amino acid residue $X_2$ in SEQ ID NO: 2 or the 156th amino acid residue in SEQ ID NO: 4 is Val, Leu, Ile, Ala, or Met, preferably Val, and/or the amino acid residue corresponding to the amino acid residue $X_3$ in SEQ ID NO: 2 or the 233rd amino acid residue in SEQ ID NO: 4 is Phe or Tyr, preferably Phe.

In the step (1) of the aforementioned method, the identification of the amino acid residue corresponding to the predetermined amino acid residue in the amino acid sequence of UGT of interest may be made as in the method of producing UGT with changed sugar donor selectivity.

By estimating the sugar donor selectivity of UGT by this method, it is possible to carry out designing of experiments for the characterization of UGT reasonably and emit unnecessary experiments.

8. Method of Estimating Kind of Sugar Attached to Position 2 of Glucose at Position 13 in Steviol Glycoside Accumulated in Plant In another side, the present invention provides a method of estimating the kind of sugar attached to position 2 of glucose at position 13 in a steviol glycoside accumulated in a plant. In one aspect, the aforementioned method comprises the following steps (1) to (3).

(1) determining the amino acid sequence of UGT expressed in a plant;

(2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT identified in (1);

(3) estimating that a proportion of glucose in the sugar attached to position 2 of glucose at position 13 in the steviol glycoside accumulated in the plant is high if the amino acid residue corresponding to the amino acid residue $X_2$ in SEQ ID NO: 2 or the 156th amino acid residue in SEQ ID NO: 4 is Thr or Ser, preferably Thr, and/or the amino acid residue corresponding to the amino acid residue $X_3$ in SEQ ID NO: 2 or the 233rd amino acid residue in SEQ ID NO: 4 is Ser or Thr, preferably Ser, and estimating that a proportion of rhamnose in the sugar attached to position 2 of glucose at position 13 in the steviol glycoside accumulated in the plant is high if the amino acid residue corresponding to the amino acid residue $X_2$ in SEQ ID NO: 2 or the 156th amino acid residue in SEQ ID NO: 4 is Val, Leu, Ile, Ala, or Met, preferably Val, and/or the amino acid residue corresponding to the amino acid residue $X_3$ in SEQ ID NO: 2 or the 233rd amino acid residue in SEQ ID NO: 4 is Phe or Tyr, preferably Phe.

The determination of the amino acid sequence of the UGT expressed in the plant in the step (1) of the aforementioned method can be made philologically or by any known experimental technique. Examples of the experimental identification technique of the amino acid sequence of the UGT include a technique involving extracting mRNA from a plant of interest, obtaining a gene having a similar nucleotide sequence using a probe or primer, etc. produced based on a known UGT nucleotide sequence, and identifying the amino acid sequence based on the gene, and the like.

In the step (2) of the aforementioned method, the identification of the amino acid residue corresponding to the predetermined amino acid residue in the amino acid sequence of the UGT of interest can be made similarly to the method of producing UGT with changed sugar donor selectivity.

In the step (3) of the aforementioned method, the term "a proportion of glucose in the sugar attached to position 2 of glucose at position 13 in the steviol glycoside accumulated in the plant is high" means that the proportion of glucose in the sugar attached to position 2 of glucose at position 13 in the steviol glycoside accumulated in the plant is higher when the amino acid residue corresponding to the amino acid residue $X_2$ in SEQ ID NO: 2 or the 156th amino acid residue in SEQ ID NO: 4 is Thr or Ser, preferably Thr, and/or the amino acid residue corresponding to the amino acid residue $X_3$ in SEQ ID NO: 2 or the 233rd amino acid residue in SEQ ID NO: 4 is Ser or Thr, preferably Ser, in the amino acid sequence of the UGT expressed in the aforementioned plant, in comparison with a different plant, for example, a plant that expresses UGT having an amino acid sequence in which the amino acid residue corresponding to the amino acid residue $X_2$ in SEQ ID NO: 2 or the 156th amino acid residue in SEQ ID NO: 4 is Val and the amino acid residue corresponding to the amino acid residue $X_3$ in SEQ ID NO: 2 or the 233rd amino acid residue in SEQ ID NO: 4 is Phe. The aforementioned proportion of glucose may be higher than a plant that expresses, for example, UGT having an amino acid sequence in which the amino acid residue corresponding to the amino acid residue $X_2$ in SEQ ID NO: 2 or the 156th amino acid residue in SEQ ID NO: 4 is Val and the amino acid residue corresponding to the amino acid residue $X_3$ in SEQ ID NO: 2 or the 233rd amino acid residue in SEQ ID NO: 4 is Phe by about 10% or more, about 20% or more, about 30% or more, about 40% or more, about 50% or more, about 60% or more, about 70% or more, about 80% or more, about 90% or more, or about 100% or more.

In the step (3) of the aforementioned method, the term "a proportion of rhamnose in the sugar attached to position 2 of glucose at position 13 in the steviol glycoside accumulated in the plant is high" means that the proportion of rhamnose in the sugar attached to position 2 of glucose at position 13 in the steviol glycoside accumulated in the plant is higher when the amino acid residue corresponding to the amino acid residue $X_2$ in SEQ ID NO: 2 or the 156th amino acid residue in SEQ ID NO: 4 is Val, Leu, Ile, Ala, or Met, preferably Val, and/or the amino acid residue corresponding to the amino acid residue $X_3$ in SEQ ID NO: 2 or the 233rd amino acid residue in SEQ ID NO: 4 is Phe or Tyr, preferably Phe, in the amino acid sequence of the UGT expressed in the aforementioned plant, in comparison with a different plant, for example, a plant that expresses UGT having an amino acid sequence in which the amino acid residue corresponding to the amino acid residue $X_2$ in SEQ ID NO: 2 or the 156th amino acid residue in SEQ ID NO: 4 is Thr and the amino acid residue corresponding to the amino acid residue $X_3$ in SEQ ID NO: 2 or the 233rd amino acid residue in SEQ ID NO: 4 is Ser. The aforementioned proportion of rhamnose may be higher than a plant that expresses, for example, UGT having an amino acid sequence in which the amino acid residue corresponding to the amino acid residue $X_2$ in SEQ ID NO: 2 or the 156th amino acid residue in SEQ ID NO: 4 is Thr and the amino acid residue corresponding to the amino acid residue $X_3$ in SEQ ID NO: 2 or the 233rd amino acid residue in SEQ ID NO: 4 is Ser by about 10% or more, about 20% or more, about 30% or more, about 40% or more, about 50% or more, about 60% or more, about 70% or more, about 80% or more, about 90% or more, or about 100% or more.

By estimating the glycoside sugar accumulated in the plant by this method, it is possible to carry out designing of experiments for the characterization of the glycoside sugar reasonably and emit unnecessary experiments and to efficiently carry out the screening for a plant having a desired glycoside sugar profile.

9. Method of Screening for Plant Accumulating Glycoside Comprising Glucose or Rhamnose as Steviol Glycoside In another side, the present invention provides a method of screening for a plant accumulating glycoside comprising glucose or rhamnose at position 2 of glucose at position 13 as a steviol glycoside. In one aspect, the aforementioned method comprises the following steps (1) to (3).

(1) determining the amino acid sequence of UGT expressed in a plant;

(2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of UGT identified in (1);

(3) determining that the plant may have accumulated glycoside comprising glucose at position 2 of glucose at position 13 as a steviol glycoside, if the amino acid residue corresponding to the amino acid residue $X_2$ in SEQ ID NO: 2 or the 156th amino acid residue in SEQ ID NO: 4 is Thr or Ser, preferably Thr, and/or the amino acid residue corresponding to the amino acid residue $X_3$ in SEQ ID NO: 2 or the 233rd amino acid residue in SEQ ID NO: 4 is Ser or Thr, preferably Ser, and determining that the plant may have accumulated glycoside comprising rhamnose at position 2 of glucose at position 13 as a steviol glycoside, if the amino acid residue corresponding to the amino acid residue $X_2$ in SEQ ID NO: 2 or the 156th amino acid residue in SEQ ID NO: 4 is Val, Leu, Ile, Ala, or Met, preferably Val, and/or the amino acid residue corresponding to the amino acid residue $X_3$ in SEQ ID NO: 2 or the 233rd amino acid residue in SEQ ID NO: 4 is Phe or Tyr, preferably Phe.

The step (1) and (2) of the aforementioned method can be carried out similarly to the aforementioned "method of estimating the kind of sugar attached to position 2 of glucose at position 13 in steviol glycoside accumulated in a plant". The UGT to be investigated in the same plant may be one plant or plural plants. When there are plural UGTs to be investigated, there may be a case in which it is determined for a certain UGT that the plant may have accumulated glycoside comprising glucose at position 2 of glucose at position 13 as a steviol glycoside and for another UGT that the plant may have accumulated glycoside comprising rhamnose at position 2 of glucose at position 13 as a steviol glycoside. In such a case, it is possible to determine that the plant has accumulated both glycosides comprising glucose or rhamnose at position 2 of glucose at position 13 as a steviol glycoside.

By this method, it is possible to screen for a plant accumulating a desired glycoside without directly detecting the glycoside contained in the plant and to increase the efficiency of selection for a food raw material.

EXAMPLES

The present invention will be described more specifically by Examples below, but the scope of the present invention is not limited to these Examples.

[Example 1] Isolation of candidate gene for steviol glycoside hexose transferase The molecular biological techniques used in this Example were according to methods described in Molecular Cloning (Sambrook et al., Cold Spring Harbor Laboratory Press, 2001) otherwise specified in detail.

cDNA from *Stevia rebaudiana* leaves was obtained by extracting total RNA from *Stevia rebaudiana* leaves using RNeasy Plant Mini kit (QIAGEN) and reverse-transcribing 0.5 μg the total RNA with Random Oligo-dT primers (RT).

The PCR reaction solution (50 μl) was prepared to have the composition of 1 μl of cDNA from *Stevia rebaudiana* leaves, 1×ExTaq buffer (Takara Bio), 0.2 mM dNTPs, 0.4 pmol/μl each of primers, 2.5 U of ExTaq polymerase. The following primers were used.

```
Primer set for amplification of UGT91D2 and
UGT91D2#16 gene
SrUGT91D2-pET15b-FW
                                    (SEQ ID NO: 37)
5 -TGCCGCGCGGCAGCCATATGTACAACGTTACTTATCATC-3

SrUGT91D2-pET15b-RV
                                    (SEQ ID NO: 38)
5 -GTTAGCAGCCGGATCCTTAACTCTCATGATCGATGGCAA-3
```

The PCR reaction included the reaction at 94° C. for 3 minutes and subsequent amplification with total 30 cycles of the reaction at 94° C. for 1 minute, at 50° C. for 1 minute, and at 72° C. for 2 minutes. Electrophoresis of the PCR product on a 0.8% agarose gel and staining with ethidium bromide have resulted in an amplified band at a size of about 1.4 kb estimated from each template DNA (FIG. 3).

This PCR product was subcloned into pENTR-TOPO Directional vector (Invitrogen) in a way recommended by the manufacturer. The sequencing was carried out by primer walking with the synthesized oligonucleotide primers with DNA Sequencer model 3100 (Applied Biosystems). As a result, the presence of 2 genes was revealed.

One of them was a known gene UGT91D2 (CDS sequence: SEQ ID NO: 3, amino acid sequence: SEQ ID NO: 4) and the other one was a novel *Stevia rebaudiana* UGT gene (CDS sequence: SEQ ID NO: 1, amino acid sequence: SEQ ID NO: 2) highly homologous with UGT91D2. This homologous gene (UGT91D2L #16) exhibited a sequence identity of 99% (9 nucleotides are different) at the DNA level and 98% (7 residues are different) at the amino acid level with UGT91D2.

[Example 2] Construction of Expression Vector

An *Escherichia coli* expression vector for this enzyme gene was obtained by cutting out the UGT91D2 and UGT91D2L #16 ORF fragments with a size of about 1.4 kb using the NdeI and BamHI restriction enzyme sites (underlined parts in SEQ ID NOs: 5 and 6) added to the primers and ligating the fragments at the NdeI and BamHI sites in the *Escherichia coli* expression vector pET15b (Novagen). The expression vector was designed such that the His tag upstream of the NdeI site in this vector is in frame with the opening reading frame of the inserted gene and a chimeric protein in which UGT and the His tag are fused is expressed.

[Example 3] Expression and Purification of Recombination Protein

To elucidate the biochemical function of this enzyme, this enzyme was expressed in *Escherichia coli*. The *Escherichia coli* strain BL21 (DE3) was transformed with the plasmids for *Escherichia coli* expression of the two UGT91D2 genes obtained as described above according to a conventional method. The obtained transformant was cultured with shaking at 37° C. overnight in 4 ml of LB medium (10 g/l tryptone pepton, 5 g/l yeast extract, 1 g/l NaCl) containing 50 µg/ml ampicillin. 80 ml of the medium of the same composition was inoculated with 4 ml of the culture liquid reached to the stationary phase and the resultant culture was cultured with shaking at 37° C. IPTG was added at a final concentration of 0.5 mM when the bacterial turbidity (OD600) reached approximately 0.5 and the shaking culture was continued for 20 hr at 18° C.

All following operations were carried out at 4° C. The cultured transformant was collected by centrifugation (5,000×g, 10 min) and suspended by adding 1 ml/g cell of Buffer S [20 mM HEPES buffer (pH 7.5), 20 mM imidazole, 14 mM β-mercaptoethanol]. Subsequently, sonication (15 sec×8 times) and centrifugation (15,000×g, 15 min) were conducted. The obtained supernatant was collected as a crude enzyme liquid. The crude enzyme liquid was loaded onto equilibrated His SpinTrap (GE Healthcare) with Buffer S and centrifuged (70×g, 30 sec). After washing with the buffer, proteins bound to the column were eluted stepwise with 5 ml each of Buffer S containing 100 mM and 500 mM imidazole. Each elution fraction was subjected to buffer exchange into 20 mM HEPES buffer (pH 7.5), 14 mM β-mercaptoethanol using Microcon YM-30 (Amicon) (dialysis against approximately 500 volumes).

As a result of CBB staining and Western blot analysis using an anti-HisTag antibody after the SDS-PAGE separation of the prepared enzyme, protein was confirmed in the vicinity of the estimated molecular weight of about 50 kDa for chimeric HisTag-fused UGT91D2 and UGT91D2L #16 proteins in the 200 mM imidazole elution fraction. Therefore, this fraction was used for the enzymatic analysis (FIG. 4).

[Example 4] Enzymatic Activity Measurement of UGT91D2 and UGT91D2L #16

The standard enzymatic reaction conditions are as follows. A reaction solution (2 mM UDP-glucose, 0.1 mM sugar receptor substrate, 100 mM potassium phosphate buffer (pH 7.5), 25 µl of purified enzyme solution) was prepared to 50 µl with distilled water and incubated at 30° C. for 1 hour to react. The LC-MS analysis of 5 µl of the enzymatic reaction solution was carried out under the following conditions.
LC Conditions
 Column: Imtakt SM-C18 3.0 um 4.6 mm I.D.×250 mm
 Mobile phase: A: MilliQ Water (+0.2% acetic acid), B: Methanol
 Gradient: 0 to 5 min (B conc 10% constant), 5 to 20 min (B conc 10%→70%), 20 to 25 min (B conc 70%→100%), 25 to 35 min (B conc 100% constant), 35 to 36 min (B conc 100%→10%), 45 min end of analysis
 Flow rate: 0.4 mL/min
 Column oven: 40° C.
MS Conditions
 ESI (negative mode)
 Selected ion monitoring: m/z 641.3, 787.3, 803.3, 935.4, 949.4, 965.4, 1111.4, 1127.4, 1259.5, 1273.5, 1289.5, 1435.5

As described in prior literature (Patent Literature 2), the reaction of the recombinant SrUGT91D2 protein and UDP-glucose with rubusoside resulted in the production of stevioside in which position 2 of glucose at position 13 is glucosylated (FIG. 5-2). Under similar conditions, SrUGT91D2L #16 also had the activity to glucosylate rubusoside to produce stevioside, but its activity was weaker than SrUGT91D2 (FIG. 5-3). Meanwhile, transfer of hexose to rubusoside was not found in the negative control (FIG. 5-1).

The reaction of the recombinant SrUGT91D2 protein and UDP-rhamnose with rubusoside then resulted in the production of dulcoside A in which position 2 of glucose at position 13 was rhamnosylated (FIG. 6-2). Under similar conditions, SrUGT91D2L #16 has the activity to rhamnosylate rubusoside to produce dulcoside A and the activity was even markedly higher than SrUGT91D2 (FIGS. 6-3). Meanwhile, transfer of hexose to rubusoside was not found in the negative control (FIG. 6-1). The specific activities of UGT91D2 and UGT91D2L #16 based on the above results are summarized in FIG. 7. Moreover, the glycosylation pathway of steviol glycosides using UGT91D2 and UGT91D2L #16 is summarized in FIG. 8.

Based on the foregoing results, it was revealed that SrUGT91D2 and SrUGT91D2L #16 have the activity to rhamnosylate position 2 of glucose at position 13 in rubusoside to produce dulcoside A. In particular, SrUGT91D2L #16, which has 7-amino acid residue difference from SrUGT91D2, has a striking rhamnose transfer activity and is considered to contribute to the synthesis of dulcoside A and Reb.C, a derivative thereof, in *Stevia rebaudiana*.

[Example 5] RebC Synthesis by Fermentative Production Using Yeast

Various steviol glycosides were produced from steviol in yeast. First, yeast that simultaneously expresses the 4 glycosylation enzyme genes UGT85C2 (SEQ ID NO: 7), UGT91D2 (SEQ ID NO: 3), UGT74G1 (SEQ ID NO: 9), and UGT76G1 (SEQ ID NO: 11) or the 4 genes UGT85C2, UGT91D2L #16, UGT74G1, and UGT76G1 from *Stevia rebaudiana* and the UDP-rhamnose synthase gene AtRHM2 (SEQ ID NO: 13) from *Arabidopsis thaliana* has been created.
Cloning of Glycosylation Enzyme Gene and Rhamnose Synthase Gene cDNA
The cDNA cloning of UGT91D2 and UGT91D2L #16 from *Stevia rebaudiana* was carried out as described above. To clone other UGT genes from *Stevia rebaudiana*, the following primer sets were prepared.

```
Primer set for amplification of UGT85C2 gene
CACC-NdeI-SrUGT85C2-Fw (underlined part is NdeI
recognition site):
                                     (SEQ ID NO: 14)
5 -CACCCATATGGATGCAATGGCTACAACTGAGAA-3

BglII-SrUGT85C2-Rv (underlined part is BglII
recognition site):
                                     (SEQ ID NO: 15)
5 -AGATCTCTAGTTTCTTGCTAGCACGGTGATTT-3

Primer set for amplification of UGT7401
CACC-NdeI-SrUGT74G1-Fw underlined part is NdeI
recognition site):
                                     (SEQ ID NO: 16)
5 -CACCCATATGGCGGAACAACAAAAGATCAAGAAAT-3

BamHI-SrUGT74G1-Rv underlined part is BamHI
recognition site):
                                     (SEQ ID NO: 17)
5 -GGATCCTTAAGCCTTAATTAGCTCACTTACAAATT-3

Primer set for amplification of UgT7601
CACC-Ndei-SrUGT76G1-Fw (underlined part is NdeI
recognition site):
                                     (SEQ ID NO: 18)
5 -CACCCATATGGAAAATAAAACGGAGACCA-3

BamHI-SrUGT76G1-Rv underlined part is BamHI
recognition site):
                                     (SEQ ID NO: 19)
5 -GGATCCTTACAACGATGAAATGTAAGAAACTA-3
```

The PCR reaction solution (50 μl) was prepared to have the composition of 1 μl of cDNA from *Stevia rebaudiana* leaves, 1×KOD plus buffer (TOYOBO), 0.2 mM dNTPs, 0.4 pmol/μl primers, 1 mM MgSO4, and 1 U heat-resistant KOD plus polymerase. The PCR reaction included the reaction at 95° C. for 5 minutes and subsequent amplification with total 30 cycles of the reaction at 94° C. for 0.5 minutes, at 50° C. for 0.5 minutes, and at 68° C. for 2 minutes. Electrophoresis of the PCR products on a 0.8% agarose gel and staining with ethidium bromide resulted in an amplified band at a size of about 1.4 kb estimated from each template DNA.

This PCR product was subcloned into pENTR-TOPO Directional vector (Invitrogen) in a way recommended by the manufacturer. The sequencing was carried out by primer walking with the synthesized oligonucleotide primers with DNA Sequencer model 3100 (Applied Biosystems) to confirm the cloning of all the intended UGT genes, that is to say, UGT85C2, UGT74G1, and UGT76G1.

Construction of expression vector for yeast To incorporate these UGT and UDP-rhamnose synthase genes and the UDP-rhamnose synthase gene AtRHM2 from *Arabidopsis thaliana* (J Biol Chem 2007 Oka et. al) into a yeast expression vector, the following primer sets were designed.

```
SrUGT85C2 set
Bgl2-UGT85C2-F (underlined part is BglII
recognition site):
                                     (SEQ ID NO: 20)
5 -ACAGATCTATGGATGCAATGGCTACAACTGAGA-3

Sal-UGT85C2-R (underlined part is SalI
recognition site):
                                     (SEQ ID NO: 21)
5 -TAGTCGACTAGTTTCTTGCTAGCACGGTGATTTC-3

SrUGT91D2 set
NotI-UGT91DIL3-F (underlined part is NotI
recognition site):
                                     (SEQ ID NO: 22)
5 -AAGCGGCCGCATGTACAACGTTACTTATCATCAAAATICAAA-3

Pac-UGT91D1L3-R (underlined part is PacI
recognition site):
                                     (SEQ ID NO: 23)
5 -CGTTAATTAACTCTCATGATCGATGGCAACC-3

SrUGT74G1 set
Not-UGT74G1-F (underlined part is NotI recognition
site):
                                     (SEQ ID NO: 24)
5 -AAGCGGCCGCATGGCGGAACAACAAAAGATCAAG-3

Pac-UGT74G1-R (underlined part is PacI recognition
site):
                                     (SEQ ID NO: 25)
5 -CGTTAATTAAGCCTTAATTAGCTCACTTACAAATTCG-3

SrUGT76G1 set
Bam-UGT76G1-F (underlined part is BamHI
recognition site):
                                     (SEQ ID NO: 26)
5 -AAGGATCCATCGAAAATAAAACCGAGACCACCG-3

Sal-UGT76G1-R (underlined part is SalI recognition
site):
                                     (SEQ ID NO: 27)
5 -GCGTCGACTTACAACGATGAAATGTAAGAAACTAGAGACTCTAA-3

AtRHM2 set
Bam-AtRHM2-F (underlined part is BamHI recognition
site):
                                     (SEQ ID NO: 28)
5 -GGATCCATGGATGATACTACGTATAAGCCAAAG-3

Xho-AtRHM2-R (underlined part is XhoI recognition
site):
                                     (SEQ ID NO: 29)
5 -CTCGAGTTAGGTTCTCTTGTTTGGTTCAAAGA-3
```

Using the combinations of template and primers, UGT85C2 as template and the SrUGT85C2 set, UGT91D2 or UGT91D2L #16 as template and the SrUGT91D2 set, UGT74G1 as template and the SrUGT74G1 set, UGT76G1 as template and the SrUGT76G1 set, and AtRHM2 as template and the AtRHM2 set, and heat-resistant KOD DNA polymerase (Toyobo), PCR amplification was conducted to add restriction enzyme sites to the both ends of each ORF. The obtained DNA fragments were subcloned using the zero Blunt-TOPO PCR cloning kit (Invitrogen) and the sequencing was carried out by primer walking with the synthesized oligonucleotide primers with DNA Sequencer model 3100 (Applied Biosystems) to confirm that each of the intended UGT genes was cloned.

To express the genes in yeast, the following expression vectors were constructed using the pESC yeast expression system (Stratagene).

(1) Construction of Plasmid pESC-URA-UGT56 or pESC-URA-UGT56R

The plasmid pESC-URA-UGT-1 was obtained by cutting out UGT85C2 with the restriction enzyme BglII and the restriction enzyme SalI and ligating the UGT85C2 into the vector pESC-URA (Stratagene) cut with the restriction enzyme BamHI and the restriction enzyme SalI. This plasmid pESC-URA-UGT-1 cut with the restriction enzyme NotI and the restriction enzyme PacI and UGT91D2 or UGT91D2L#16 cut with the restriction enzyme NotI and the restriction enzyme PacI were ligated to obtain pESC-URA-UGT56 or pESC-URA-UGT56R.

(2) Construction of Plasmid pESC-HIS-UGT78

The plasmid pESC-HIS-UGT-8 was obtained by cutting out UGT76G1 with the restriction enzyme BamHI and the restriction enzyme SalI and ligating the UGT76G1 with the vector pESC-HIS (Stratagene) cut with the same restriction enzymes. This plasmid pESC-HIS-UGT-8 cut with the restriction enzyme NotI and the restriction enzyme PacI and UGT74G1 cut with NotI and PacI were ligated to obtain pESC-HIS-UGT78.

(3) Construction of Plasmid pESC-TRP-AtRHM2

The plasmid pESC-TRP-AtRHM2 was obtained by cutting out AtRHM2 with the restriction enzyme BamHI and the restriction enzyme XhoI and ligating the AtRHM2 with the vector pESC-TRP (Stratagene) cut with the same restriction enzymes.

Transformation of yeast The plasmids set forth in Table 1 were introduced into the *Saccharomyces cerevisiae* strain YPH499 (ura3-52 lys2-801$^{amber}$ ade2-101$^{ochre}$ trp1-Δ63 his3-Δ200 leu2-Δ1 a) as a host by the lithium acetate method. Those that grew on SC-Trp&Ura&His agar medium (6.7 g of Yeast nitrogen base without amino acids, 20 g of glucose, 1.3 g of amino acid mixture powder Trp&Ura&His, 20 g of Bacto agar, per 1 L) were selected as transformant strains.

TABLE 1

| Transformant strain | Introduced plasmid | Introduced gene |
| --- | --- | --- |
| A-5678 | pESC-URA-UGT56 | SrUGT85C2, SrUGT91D2 |
| | pESC-HIS-UGT78 | SrUGT74G1, SrUGT76G1 |
| | pESC-TRP-AtRHM2 | AtPHM2 |
| A-56R78 | pESC-URA-UGT56R | SrUGT85C2, UGT91D2L#16 |
| | pESC-HIS-UGT78 | SrUGT74G1, SrUGT76G1 |
| | pESC-TRP-AtARM2 | AtRHM2 |
| C-5678 | pESC-URA-UGT56 | SrUGT85C2, SrUGT91D2 |
| | pESC-HIS-UGT78 | SrUGT74G1, SrUGT76G1 |
| | pESC-TRP | |
| C-56R78 | pESC-URA-UGT56R | SrUGT85C2, UGT91D2L#16 |
| | pESC-HIS-UGT78 | SrUGT74G1, SrUGT76G1 |
| | pESC-TRP | |

The amino acid mixture powder Trp&Ura&His was prepared by mixing 2.5 g of adenine sulfate, 1.2 g of L-arginine hydrochloride, 6.0 g of L-aspartic acid, 6.0 g of L-glutamic acid, 3.6 g of L-leucine, 1.8 g of L-lysine, 1.2 g of L-methionine, 3.0 g of L-phenylalanine, 22.5 g of L-serine, 12 g of L-threonine, 1.8 g of L-tyrosine, and 9.0 g of L-valine.

Induction and Analysis of Expression of Transgene

The obtained transformant strain was cultured as follows.

First, 10 ml of SC-Trp&Ura&His liquid medium (SC-Trp&Ura&His agar medium without Bacto agar) was inoculated each transformant strain as a preculture and cultured with shaking at 30° C. for 1 day. Then, 10 ml of SG-Trp&Ura&His liquid medium (6.7 g of Yeast nitrogen base without amino acids, 20 g of galactose, 1.3 g of amino acid mixture powder Trp&Ura&His, per 1 L) was inoculated with 1 ml of the liquid preculture as a main culture and cultured with shaking at 30° C. for 2 days.

To confirm whether the gene introduced in the transformant strain is expressed, bacterial cells were collected from the liquid culture and total RNA was purified with RNeasy Mini Kit.

cDNA was synthesized by taking 1 μg of the total RNA and using Super script II reverse transcriptase (Thermo Fisher Scientific) and random hexamers as primers.

To confirm the expression of the transgenes, the following primers were prepared.

For confirmation of expression of UGT85C2
UGT85C2-r1:
(SEQ ID NO: 30)
5 -CAAGTCCCCAACCAAATTCCGT-3

For confirmation of expression of UGT91D2 and UGT91D2L3#16
UGT91D1L3-r1:
(SEQ ID NO: 31)
5 -CACGAACCCGTCTGGCAACTC-3

For confirmation of expression of UGT74G1
UGT74Gi-r1:
(SEQ ID NO: 32)
5 -CCCGTGTGATTTCTTCCACTTGTTC-3

For confirmation of expression of UGT76G1
UGT76G1-r1:
(SEQ ID NO: 33)
5 -CAAGAACCCATCTGGCAACGG-3

For confirmation of expression of AtAHM2
AtAHM2-r1
(SEQ ID NO: 34)
5 -GCTTTGTCACCAGAATCACCATT-3

GAL10p region (Promoter region)
PGAL10-f3:
(SEQ ID NO: 35)
5 -GATTATTAAACTTCTTTGCGTCCATCCA-3

GAL1p region (Promoter region
PGAL1-f3:
(SEQ ID NO: 36)
5 -CCTCTATACTTTAACGTCAAGGAGAAAAAACC-3

Expression of each transgene was confirmed by performing PCR using the following combinations of primers, the previously synthesized cDNA as template, and ExTaq (Takara Bio) and agarose gel electrophoresis of the products.
UGT85C2:UGT85C2-r1(SEQ ID NO: 30) and PGAL1-f3 (SEQ ID NO: 36)
UGT91D2 or UGT91D2L3:UGT91D1L3-r1(SEQ ID NO: 31) and PGAL10-f3(SEQ ID NO: 35)
UGT74G1:UGT74G1-r1(SEQ ID NO: 32) and PGAL1-f3 (SEQ ID NO: 36)
UGT76G1:UGT76G1-r1(SEQ ID NO: 33) and PGAL10-f3 (SEQ ID NO: 35)
AtRHM2:AtAHM2-r1(SEQ ID NO: 34) and PGAL10-f3 (SEQ ID NO: 35)

This confirmed that the introduced genes were expressed in the transformant strains.

Production of Reb.C

The culture was conducted under the same conditions as Example 3 above, except that 0.5 μg or 2 μg of steviol (ChromaDex Inc.) per 1 ml of medium was added to the liquid medium for the main culture. After completing the culture, the supernatant and bacterial cells were separated by centrifugation of the liquid culture. The culture supernatant was washed with acetonitrile and then loaded on the Sep-Pak C18 column equilibrated with water, washed with 20% acetonitrile and then eluted with 80% acetonitrile, dried, and then dissolved in a little amount of 80% acetonitrile to prepare a glycoside sample. This glycoside sample was subjected to the following analyses.

Analysis by HPLC

The obtained glycoside sample was analyzed with high performance liquid chromatography (HPLC). The HPLC conditions are as follows.

Column: COSMOSIL 5C$_{18}$-AR-II 4.6 mm I.D.×250 mm (Nacalai Tesque, Inc.)

Mobile phase: A; Acetonitrile, B; 10 mM sodium phosphate buffer (pH 2.6), Gradient: 40 min, B conc 70%→30%, linear gradient Flow rate: 1 ml/min
Temperature: 40° C.
Detection: UV 210 nm Analysis by LC-MS The analysis by LC-MS was conducted under the following conditions.

LC Conditions
Column: Imtakt SM-C18 3.0 um 4.6 mm I.D.×250 mm
Mobile phase: A: MilliQ Water (+0.2% acetic acid), B: Methanol
Gradient: 0 to 5 min (B conc 10% constant), 5 to 20 min (B conc 10%→70%), 20 to 25 min (B conc 70%→100%), 25 to 35 min (B conc 100% constant), 35 to 36 min (B conc 100%→10%), 45 min end of analysis
Flow rate: 0.4 mL/min
Column oven: 40° C.

MS Conditions
ESI (negative mode)
Selected ion monitoring: m/z 641.3, 787.3, 803.3, 935.4, 949.4, 965.4, 1111.4, 1127.4, 1259.5, 1273.5, 1289.5, 1435.5

The results are shown in FIGS. 9 to 11. Reb.C was produced in the strains A-5678 and A-56R78 coexpressing the UDP-rhamnose synthase gene and the steviol glycosylation enzyme gene. The amount of Reb.C produced in the strain A-56R78 expressing UGT91D2L#16 was higher than that in the strain A-5678 expressing UGT91D2.

[Example 6] Analysis of SrUGT91D2L #16

Homology Structure Analysis

The amino acid residue that contributes to a striking rhamnose transfer activity in UGT91D2L#16 was estimated. Homology structure analysis was performed to estimate which residue of the 7 residues different between UGT91D2L#16 and UGT91D2 is related to the activity. A homology model of UGT91D2 in an existing method (Noguchi et al (2009) Plant Cell. 21 (5): 1556-152) was produced by using the structural information (RCSB Protein Data Bank (PDB), PDB ID:2PQ6) of UGT85H2 from Medicago in the family Fabaceae, of which crystal structure has been already solved, as the protein structure template, with the sugar donor UDP-glucose (PDB ID:2C1Z) docked as a substrate.

The determination of the locations of the 7 residues that are different from UGT91D2L #16 in a constructed UGT91D2 homology model revealed that the 156th Thr residue is in the vicinity of UDP-glucose, suggesting its contribution to the selectivity of UDP-sugar. The 233rd Ser residue was also found in the vicinity of the Thr residue, suggesting its contribution to the UDP-sugar selectivity (FIGS. 12 to 13).

Generation of Mutants

The mutants in which the amino acids estimated by the homology model are substituted in UGT91D2 and UGT91D2L#16 were generated. Mutants 1 and 2 were used in the in vitro assay with the *Escherichia coli*-expressed protein and Mutants 1 to 6 were used in the in vivo assay in yeast.

Mutant 1: UGT91D2-T156V (with substitution of the 156th Thr residue in UGT91D2 with a Val residue)
Mutant 2: UGT91D2L#16-V156T (with substitution of the 156th Val residue in UGT91D2L#16 with a Thr residue)
Mutant 3: UGT91D2-S233F (with substitution of the 233rd Ser residue in UGT91D2 with a Phe residue)
Mutant 4: UGT91D2L#16-F233S (with substitution of the 233rd Phe residue in UGT91D2L#16 with a Ser residue)
Mutant 5: UGT91D2-T156V/S233F (with substitution of the 156th Thr residue and the 233rd Ser residue in UGT91D2 with a Val residue and a Phe residue, respectively)
Mutant 6: UGT91D2L#16-V156T/F233 (with substitution of the 156th Val residue and the 233rd Phe residue in UGT91D2L#16 with a Thr residue and a Ser residue, respectively)

The plasmids containing DNA encoding the mutants were prepared as follows. For Mutant 1 as an example, an amplified fragment in which two fragments were ligated was obtained by mixing a DNA fragment obtained by the PCR with cDNA of UGT91D2 as a template and a primer set of the following SrUGT91D2-T156V-FW and SrUGT91D2-pET15b-RV (SEQ ID NO: 39 and SEQ ID NO: 38) and a DNA fragment obtained by the PCR with cDNA of UGT91D2 as a template and a primer set of SrUGT91D2-T156V-RV and SrUGT91D2-pET15b-FW (SEQ ID NO: 40 and SEQ ID NO: 37) and performing PCR again with a primer set of SrUGT91D2-pET15b-FW and SrUGT91D2-pET15b-RV (SEQ ID NO: 37 and SEQ ID NO: 38). By inserting this ligated fragment into the *Escherichia coli* expression vector pET15b (Novagen) digested with NdeI and BamHI using GeneArt Seamless Cloning and Assembly (Thermo Fisher Scientific Inc.), a plasmid for expression in *Escherichia coli* containing DNA encoding the UGT91D2-T156V mutant was obtained. The DNA encoding the UGT91D2-T156V mutant was sequenced with DNA Sequencer model 3100 (Applied Biosystems) by primer walking with synthesized oligonucleotide primers to confirm that there was no mutation other than the intended mutation. The plasmids containing DNA encoding other mutants were similarly prepared.

```
SrUGT91D2-pET15b-FW:
                                    (SEQ ID NO: 37)
5-TGCCGCGCGGCAGCCATATGTACAACGTTACTTATCATC-3

SrUGT91D2-JET15b-RV:
                                    (SEQ ID NO: 38)
5-GTTAGCAGCCGGATCCTTAACTCTCATGATCGATGGCAA-3

SrUGT91D2-T156V-FW:
                                    (SEQ ID NO: 39)
5-CACTTCTCCGTCGTCACTCCATG-3

SrUGT91D2-T156V-RV:
                                    (SEQ ID NO: 40)
5-CATGGAGTGACGACGGAGAAGTG-3

SrUGT91D2-Like-V156T-FW
                                    (SEQ ID NO: 41)
5-CACTTCTCCGTCACCACTCCATG-3

SrUGT91D2-Like-V156T-RV
                                    (SEQ ID NO: 42)
5-CATGGAGTGGTGACGGAGAAGTG-3

SrUGT91D2-S233T-FW
                                    (SEQ ID NO: 43)
5-CTGATTGTTTGCTTTTCAAATGTTACCATGAG-3

SrUGT91D2-5233F-RV
                                    (SEQ ID NO: 44)
5-CTCATGGTAACATTTGAAAAGCAAACAATCAG-3

SrUGT91D2L-F233S-FW
                                    (SEQ ID NO: 45)
5-CTGATTGTTTGCTTTCCAAATGTTACCATGAG-3

SrUGT91D2L-F233S-RV
                                    (SEQ ID NO: 46)
5-CTCATGGTAACATTTGGAAAGCAAACAATCA
```

Evaluation in *Escherichia coli*

Any of the 6 mutant proteins expressed in *Escherichia coli* using the same method as Examples 3 and 4 was confirmed by CBB staining and Western blot analysis to have a band in the vicinity of the estimated size of 55 kDa.

Evaluation of Mutants 1 and 2 was then made using the protein expressed in *Escherichia coli* in the same manner as in Example 4. The glucosylation activity (GlcT) and the rhamnosylation activity (RhaT) were evaluated using UDP-glucose and UDP-rhamnose, respectively, as the sugar donor and using rubusoside as the substrate, which is a sugar receptor. Stevioside and dulcoside A were produced as the reaction products in the former and in the latter, respectively.

In Mutant 1, the relative GlcT activity decreased to 5.5% based on the GlcT activity of the wildtype UGT91D2 of 100% (FIG. 14A) and the relative RhaT activity was a high activity of about 4.4 times based on the RhaT activity of the wildtype UGT91D2 of 100% (FIG. 14B). Meanwhile, in Mutant 2, the relative GlcT activity increased to a high activity of 3.7 times based on the GlcT activity of the wildtype UGT91D2L#16 of 100% (FIG. 14C) and the relative RhaT activity was a low activity of 35% based on the RhaT activity of the wildtype UGT91D2L#16 of 100% (FIG. 14D). From the foregoing results, it was found that the sugar donor selectivity mainly shifts to UDP-glucose when the amino acid at the 156th position in UGT91D2 is a Thr residue and to UDP-rhamnose when the position is a Val residue.

Evaluation in Yeast

To confirm the specificity of the mutants in yeast, the enzyme activities of Mutants 1 to 6 were then compared with UGT91D2 and UGT91D2L#16 and evaluated. The genes to be introduced and expressed in the yeast transformants were 4 genes: any one of the UGT91 genes, UGT85C2, UGT74G1, and AtRHM2.

(1) Construction of Plasmid pESC-URA-UGT56M

The mutant vector for yeast expression was constructed as follows. DNA was amplified by PCR using a plasmid containing DNA encoding one of the mutants produced as described above as a template and the SrUGT91D2 set of primers (SEQ ID NO: 22, 23). The plasmids pESC-URA-UGT56M1 to pESC-URA-UGT56M6, which can coexpress UGT85C2 and one of the UGT91D2 mutants, were constructed by incorporating a DNA fragment cut with restriction enzymes into the plasmid pESC-URA-UGT-1 in a similar way to that in Example 5.

(2) Construction of Plasmid pESC-HIS-UGT7

The plasmid pESC-HIS-UGT7 was obtained by cutting out UGT74G1 with the restriction enzymes NotI and PacI and ligating the UGT74G1 with the vector pESC-HIS cut with the same restriction enzymes.

pESC-URA-UGT56, pESC-URA-UGT56R, or pESC-TRP-AtRHM2 used in Example 5 was used as the vector for UGT91D2, UGT91D2L #16, or AtRHM2.

Transformation of Yeast

A combination of the plasmids pESC-TRP-AtRHM2 and pESC-HIS-UGT7 and any one of ESC-URA-UGT56M1 to pESC-URA-UGT56M6, pESC-URA-UGT56, and pESC-URA-UGT56R was introduced into the *Saccharomyces cerevisiae* strain YPH499 as a host by the lithium acetate method and transformant strains were selected in a similar way to that in Example 5. In this way, 8 transformant strains, different in UGT91D2, were obtained. It was confirmed in a similar way to Example 5 that the transgenes are expressed in the obtained transformant strains. The analysis of steviol glycosides in the culture and culture supernatant for each transformant strain was carried out in a similar way to that in Example 5, except that 2 µg steviol per 1 ml medium was added.

The results of analysis of steviol glycosides in the culture supernatant of yeast indicated a decreasing tendency of the amount of the GlcT activity product stevioside produced in the yeast in which UGT91D2-based mutants (Mutants 1, 3, 5) were expressed. For example, in the yeast in which Mutant 5 was expressed, the amount of stevioside was decreased to 37.5% with the amount of stevioside produced in the yeast in which wildtype UGT91D2 was expressed being 100%, and the activity was equivalent to the wildtype UGT91D2L#16 (FIG. 15A). Meanwhile, the GlcT activity in any of the UGT91D2L#16-based mutants (Mutants 2, 4, 6) was higher than that in the wildtype UGT91D2L#16. The activity in Mutant 6 was increased to about 2.7 times of the wildtype UGT91D2L#16 and equivalent to that in the wildtype UGT91D2 (FIG. 15A).

The amount of the RhaT activity product dulcoside A produced in the yeast in which Mutants 1, 3, and 5 was expressed was found to be increased to about 1.5 times or more in comparison with the amount of dulcoside A produced in the yeast in which the wildtype UGT91D2 was expressed (FIG. 15B). Meanwhile, the RhaT activity in the UGT91D2L#16-based mutants was found to be decreased by 30% or more in any of the mutants in comparison with that in the wildtype UGT91D2L#16.

Furthermore, the product behaviors of the two steviol rhamnosides (steviol position 13-Glc-Rha($\alpha$1,2), position 19-Glc-Rha($\alpha$1,2) and steviol position 13-Glc-Rha($\alpha$1,2), position 19-H) other than dulcoside A similar to those of dulcoside A were found (FIGS. 15C to D).

The forgoing results confirmed that the sugar in the steviol glycoside shifts to rhamnose when the 156th residue of UGT91D2 is Val and to glucose when the residue is Thr in de novo expression in yeast, similar to the results of the *Escherichia coli* recombinant protein. Furthermore, it was also indicated that the sugar shifts to rhamnose when the 233rd residue is Phe and to glucose when the residue is Ser.

INDUSTRIAL AVAILABILITY

According to the present invention, it is possible to rhamnosylate position 2 of glucose at position 13 in steviol and control the sweetness and taste quality of the steviol glycoside using the SrUGT91D2L#16 gene. Using these genes as markers, it is possible to select plant bodies different in the Reb.C content. Moreover, the present invention provides a molecule tool for producing rhamnose-containing steviol glycosides represented by Reb.C not only in plants but also in microorganisms.

SEQUENCE LISTING FREE TEXT

In SEQ ID NO: 2, the amino acid residue $X_1$ represents the 42nd amino acid residue Phe, the amino acid residue $X_2$ represents the 156th amino acid residue Val, the amino acid residue $X_3$ represents the 233rd amino acid residue Phe, the amino acid residue $X_4$ represents the 298th amino acid residue Ala, the amino acid residue $X_5$ represents the 394th amino acid residue Leu, the amino acid residue $X_6$ represents the 439th amino acid residue Asn, and the amino acid residue $X_7$ represents the 471st amino acid residue Phe.

The invention claimed is:

1. A protein consisting of an amino acid sequence wherein 1 to 48 amino acids other than the amino acid residue $X_7$ are deleted, substituted, inserted, and/or added in the amino acid sequence of SEQ ID NO: 2 and having an activity to add hexose at position 2 of glucose at position 13 in a compound represented by the following formula (I):

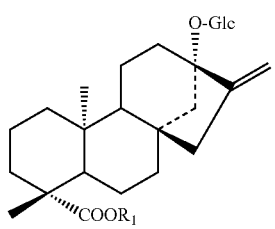

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a (C3-$C_{10}$ cycloalkyl)$C_1$-$C_{10}$ alkyl group or a sugar residue.

2. The protein according to claim 1, wherein the protein is
a protein consisting of an amino acid sequence wherein 1 to 48 amino acids other than the amino acid residues $X_1$ to $X_7$ are deleted, substituted, inserted, and/or added in the amino acid sequence of SEQ ID NO: 2 and having an activity to add hexose at position 2 of glucose at position 13 in a compound represented by the formula (I).

3. A protein according to any one selected from the group consisting of the following (a) to (c):
(a) a protein consisting of an amino acid sequence wherein 1 to 48 amino acids other than the amino acid residues $X_2$ and/or $X_3$ are deleted, substituted, inserted, and/or added in the amino acid sequence of SEQ ID NO: 2 and having an activity to add hexose at position 2 of glucose at position 13 in a compound represented by the following formula (I):

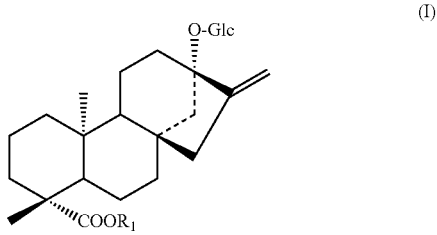

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a ($C_3$-$C_{10}$ cycloalkyl)$C_1$-$C_{10}$ alkyl group or a sugar residue;

(b) a protein consisting of an amino acid sequence wherein the 156th amino acid residue is Val and/or the 233rd amino acid residue is Phe in the amino acid sequence of SEQ ID NO: 4;

(c) a protein wherein the amino acid residue $X_2$ is Thr and/or the amino acid residue $X_3$ is Ser in the amino acid sequence of SEQ ID NO: 2.

4. The protein according to claim 1, wherein the hexose is selected from the group consisting of glucose or rhamnose.

5. The protein according to claim 1, wherein the $R_1$ is H or a sugar residue of a glucose monomer or a glucose dimer.

6. The protein according to claim 1, wherein the compound is steviolmonoside or rubusoside.

7. A polynucleotide encoding a protein consisting of an amino acid sequence wherein 1 to 48 amino acids other than the amino acid residue $X_7$ are deleted, substituted, inserted, and/or added in the amino acid sequence of SEQ ID NO: 2 and having an activity to add hexose at position 2 of glucose at position 13 in a compound represented by the following formula (I):

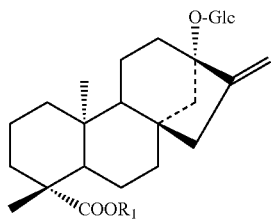

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a $(C_3$-$C_{10}$ cycloalkyl$)C_1$-$C_{10}$ alkyl group or a sugar residue.

8. The polynucleotide according to claim 7, wherein the polynucleotide is
a polynucleotide encoding a protein consisting of an amino acid sequence wherein 1 to 48 amino acids other than the amino acid residues $X_1$ to $X_7$ are deleted, substituted, inserted, and/or added in the amino acid sequence of SEQ ID NO: 2 and having an activity to add hexose at position 2 of glucose at position 13 in a compound represented by the formula (I).

9. A polynucleotide selected from the group consisting of the following (a) to (c):
(a) a polynucleotide encoding a protein consisting of an amino acid sequence wherein 1 to 48 amino acids other than the amino acid residues $X_2$ and/or $X_3$ are deleted, substituted, inserted, and/or added in the amino acid sequence of SEQ ID NO: 2 and having an activity to add hexose at position 2 of glucose at position 13 in a compound represented by the following formula (I):

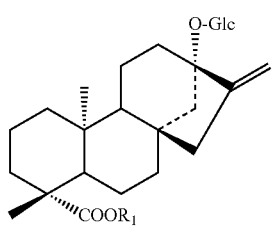

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a $(C_3$-$C_{10}$ cycloalkyl$)C_1$-$C_{10}$ alkyl group or a sugar residue;

(b) a polynucleotide encoding a protein wherein the 156th amino acid residue is Val and/or the 233rd amino acid residue is Phe in the amino acid sequence of SEQ ID NO: 4;

(c) a polynucleotide encoding a protein wherein the amino acid residue $X_2$ is Thr and/or the amino acid residue $X_3$ is Ser in the amino acid sequence of SEQ ID NO: 2.

10. The polynucleotide according to claim 7, wherein the hexose is selected from the group consisting of glucose or rhamnose.

11. The polynucleotide according to claim 7, wherein the $R_1$ is H or a sugar residue of a glucose monomer or a glucose dimer.

12. The polynucleotide according to claim 7, wherein the compound is steviolmonoside or rubusoside.

13. A non-human transformant in which the polynucleotide according to claim 7 is introduced.

14. The transformant according to claim 13, wherein the polynucleotide is inserted into an expression vector.

15. The transformant according to claim 13, wherein the transformant is a plant.

16. A method of producing a protein, comprising culturing the non-human transformant according to claim 13 under conditions to produce said protein, wherein the protein has an activity to add hexose at position 2 of glucose at position 13 in a compound represented by the following formula (I);

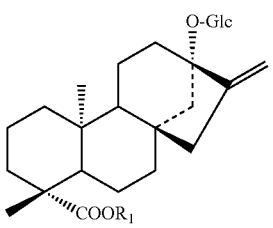

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a $(C_3$-$C_{10}$ cycloalkyl$)C_1$-$C_{10}$ alkyl group or a sugar residue.

17. A method of producing a steviol glycoside, comprising culturing the non-human transformant according to claim 13 under conditions to produce the steviol glycoside.

18. The method according to claim 17, wherein the steviol glycoside is steviolbioside, stevioside, dulcoside A, Reb.E or Reb.C, or a combination thereof.

19. A method of producing a steviol glycoside, comprising reacting the protein according to claim 1, a UDP-sugar, and a compound represented by the following formula (I):

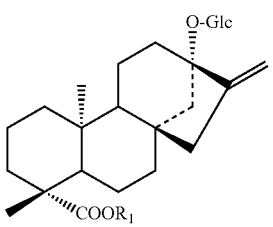

(I)

wherein $R_1$ represents H, a $C_1$-$C_{20}$ alkyl group, a $C_2$-$C_{20}$ alkenyl group, a $C_2$-$C_{20}$ alkynyl group, a $C_4$-$C_{20}$ alkyldienyl group, a $C_6$-$C_{18}$ aryl group, a $C_6$-$C_{20}$ alkylaryl group, a $C_6$-$C_{20}$ arylalkyl group, a $C_4$-$C_{20}$ cycloalkyl group, a $C_4$-$C_{20}$ cycloalkenyl group, a $(C_3$-$C_{10}$ cycloalkyl$)C_1$-$C_{10}$ alkyl group or a sugar residue.

20. The method according to claim 19, wherein the sugar in the UDP-sugar is glucose or rhamnose.

21. The method according to claim 19, wherein the steviol glycoside is steviolbioside, stevioside, dulcoside A, Reb.E or Reb.C, or a combination thereof.

22. A method of estimating the kind of sugar attached to position 2 of glucose at position 13 in a steviol glycoside accumulated in a plant, comprising:

(1) determining the amino acid sequence of a UDP sugar-dependent glycosyltransferase (UGT) expressed in a plant;
(2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of the UGT identified in the above (1); and
(3) estimating that a proportion of glucose in the sugar attached to position 2 of glucose at position 13 in the steviol glycoside accumulated in the plant is high compared to a plant that expresses UGT having an amino acid sequence in which the amino acid residue corresponding to the amino acid residue $X_2$ in SEQ ID NO: 2 or the 156th amino acid residue in SEQ ID NO: 4 is Val and/or the amino acid residue corresponding to the amino acid residue $X_3$ in SEQ ID NO: 2 or the 233rd amino acid residue in SEQ ID NO: 4 is Phe, if the amino acid residue corresponding to the amino acid residue $X_2$ in SEQ ID NO: 2 or the 156th amino acid residue in SEQ ID NO: 4 is Thr or Ser and/or if the amino acid residue corresponding to the amino acid residue $X_3$ in SEQ ID NO: 2 or the 233rd amino acid residue in SEQ ID NO: 4 is Ser or Thr, and estimating that a proportion of rhamnose in the sugar attached to position 2 of glucose at position 13 in the steviol glycoside accumulated in the plant is high compared to a plant that expresses UGT having an amino acid sequence in which the amino acid residue corresponding to the amino acid residue $X_2$ in SEQ ID NO: 2 or the 156th amino acid residue in SEQ ID NO: 4 is Thr and/or the amino acid residue corresponding to the amino acid residue $X_3$ in SEQ ID NO: 2 or the 233rd amino acid residue in SEQ ID NO: 4 is Ser, if the amino acid residue corresponding to the amino acid residue $X_2$ in SEQ ID NO: 2 or the 156th amino acid residue in SEQ ID NO: 4 is Val, Leu, Ile, Ala, or Met and/or if the amino acid residue corresponding to the amino acid residue $X_3$ in SEQ ID NO: 2 or the 233rd amino acid residue in SEQ ID NO: 4 is Phe or Tyr.

23. A method of screening for a plant accumulating glycoside comprising glucose or rhamnose at position 2 of glucose at position 13 as a steviol glycoside, comprising:
(1) determining the amino acid sequence of UGT expressed in a plant;
(2) identifying an amino acid residue corresponding to an amino acid residue selected from the amino acid residue $X_2$ in SEQ ID NO: 2, the amino acid residue $X_3$ in SEQ ID NO: 2, the 156th amino acid residue in SEQ ID NO: 4, and/or the 233rd amino acid residue in SEQ ID NO: 4 in the amino acid sequence of the UGT identified in the above (1); and
(3) determining that the plant may have accumulated glycoside comprising glucose at position 2 of glucose at position 13 as a steviol glycoside, if the amino acid residue corresponding to the amino acid residue $X_2$ in SEQ ID NO: 2 or the 156th amino acid residue in SEQ ID NO: 4 is Thr or Ser and/or if the amino acid residue corresponding to the amino acid residue $X_3$ in SEQ ID NO: 2 or the 233rd amino acid residue in SEQ ID NO: 4 is Ser or Thr, and determining that the plant may have accumulated glycoside comprising rhamnose at position 2 of glucose at position 13 as a steviol glycoside, if the amino acid residue corresponding to the amino acid residue $X_2$ in SEQ ID NO: 2 or the 156th amino acid residue in SEQ ID NO: 4 is Val, Leu, Ile, Ala, or Met and/or if the amino acid residue corresponding to the amino acid residue $X_3$ in SEQ ID NO: 2 or the 233rd amino acid residue in SEQ ID NO: 4 is Phe or Tyr.

\* \* \* \* \*